United States Patent
Kroczek

(10) Patent No.: US 10,688,165 B2
(45) Date of Patent: *Jun. 23, 2020

(54) MEDICAMENT FOR USE IN A METHOD OF INDUCING OR EXTENDING A CELLULAR CYTOTOXIC IMMUNE RESPONSE

(71) Applicant: Bundesrepublik Deutschland letztvertreten durch das Robert Koch-Institut vertreten durch seinen Präsidenten, Berlin (DE)

(72) Inventor: Richard Kroczek, Berlin (DE)

(73) Assignee: Bundesrepublik Deutschland letztvertreten durch das Robert-Koch-Institut vertreten durch seinen Präsidenten, Berlin (DE)

( * ) Notice: Subject to any disclaimer, the term of this patent is extended or adjusted under 35 U.S.C. 154(b) by 94 days.

This patent is subject to a terminal disclaimer.

(21) Appl. No.: 15/126,487

(22) PCT Filed: Mar. 17, 2015

(86) PCT No.: PCT/EP2015/055568
§ 371 (c)(1),
(2) Date: Sep. 15, 2016

(87) PCT Pub. No.: WO2015/140172
PCT Pub. Date: Sep. 24, 2015

(65) Prior Publication Data
US 2017/0087232 A1 Mar. 30, 2017

(30) Foreign Application Priority Data
Mar. 17, 2014 (EP) .................................... 14000971

(51) Int. Cl.
C12N 5/00 (2006.01)
C12N 5/02 (2006.01)
A61K 39/00 (2006.01)

(52) U.S. Cl.
CPC .. *A61K 39/0011* (2013.01); *A61K 2039/5154* (2013.01); *A61K 2039/5158* (2013.01); *A61K 2039/545* (2013.01); *A61K 2039/55533* (2013.01); *A61K 2039/55561* (2013.01); *A61K 2039/572* (2013.01)

(58) Field of Classification Search
None
See application file for complete search history.

(56) References Cited

U.S. PATENT DOCUMENTS

| 4,946,778 | A | 8/1990 | Ladner et al. |
| 5,643,565 | A | 7/1997 | Doyle et al. |
| 2010/0310501 | A1 | 12/2010 | Boyman et al. |
| 2017/0080067 | A1 | 3/2017 | Kroczek |

FOREIGN PATENT DOCUMENTS

| EP | 2505206 A2 | 10/2012 |
| EP | 2641915 A1 | 9/2013 |
| WO | WO-02/053176 A2 | 7/2002 |
| WO | WO-2007/095643 A2 | 8/2007 |
| WO | WO-2007/103009 A2 | 9/2007 |
| WO | WO-2009/061853 A2 | 5/2009 |
| WO | WO-2009/065561 A2 | 5/2009 |
| WO | WO-2009/155332 A1 | 12/2009 |
| WO | WO-2010/104836 A1 | 9/2010 |
| WO | WO-2014/028748 A1 | 2/2014 |
| WO | WO-2014/201378 A1 | 12/2014 |

OTHER PUBLICATIONS

Moron et al., 2004, Trends Immunology, Voi. 25: 92-97.*
Mostbock et al., 2008, J. Immunol. Volo. 180: 5118-5129.*
Okada et al., 2011, J. Clin. Oncol. vol. 29: 330-336.*
Nestle et al., "Vaccination of melanoma patients with peptide- or tumor lysate-pulsed dendritic cells," Nat Med. 4(3):328-32 (1998).
Boyman et al., "Selective stimulation of T cell subsets with antibody-cytokine immune complexes," Science. 311(5769):1924-7 (2006).
Verdeil et al., "Adjuvants targeting innate and adaptive immunity synergize to enhance tumor immunotherapy," Proc Natl Acad Sci USA. 105(43):16683-88 (2008).
Carmenate et al., "Human IL-2 mutein with higher antitumor efficacy than wild type IL-2," J Immunol. 190(12):6230-8 (2013).
Bachem et al., "Superior antigen cross-presentation and XCR1 expression define human CD11c+CD141+ cells as homologues of mouse CD8+ dendritic cells," J Exp Med. 207(6):1273-81 (2010).
Song et al., "Significant anti-tumour activity of adoptively transferred T cells elicited by intratumoral dendritic cell vaccine injection through enhancing the ratio of CD8(+) T cell/regulatory T cells in tumour," Clin Exp Immunol. 162(1):75-83 (2010).
Lou et al. "Dendritic cells strongly boost the antitumor activity of adoptively transferred T cells in vivo," available in OMC Feb. 13, 2008, published in final edited form as: Cancer Res. 64(18):6783-90 (2004) (22 pages).
Kondo et al., "Adoptive immunotherapy for pancreatic cancer using MUC1 peptide-pulsed dendritic cells and activated T lymphocytes," Anticancer Res. 28(1B):379-87 (2008).
Opel et al., "Combined treatment using adoptive cell therapy, extended pharmacokinetic IL-2, and tumor-specific antibodies leads to cures of established B16F10 tumors and extended in vivo T cell survival," J Immunother Cancer. 1(Suppl 1):P26 (2013).

(Continued)

*Primary Examiner* — Michail A Belyavskyi
(74) *Attorney, Agent, or Firm* — Clark & Elbing LLP

(57) ABSTRACT

The present invention relates to a medicament for use in a method of extending a cellular cytotoxic immune response against an antigen-comprising protein, the method comprising the step of: i) administering to a patient having T cells activated against an antigen a peptide-loaded major histocompatibility complex class I (MHC-I) presenting cell and an adjuvant which supports a Th-1-mediated response, wherein the peptide is derived from the antigen-comprising protein, thereby re-activating the activated T cell, wherein the peptide-loaded major histocompatibility complex class I (MHC-I) presenting cell of step i) is administered in a time frame of from 0 h to 14 days after the T cells were activated against an antigen.

17 Claims, 10 Drawing Sheets

Specification includes a Sequence Listing.

(56) References Cited

OTHER PUBLICATIONS

Kim et al., "DNA vaccine with alpha-galactosylceramide at prime phase enhances anti-tumor immunity after boosting with antigen-expressing dendritic cells," available in PMC Aug. 4, 2011, published in final edited form as: Vaccine. 28(45):7297-7305 (2010) (19 pages).
Bachem et al., "Expression of XCR1 Characterizes the Batf3-Dependent Lineage of Dendritic Cells Capable of Antigen Cross-Presentation," Front Immunol. 3(Article 214): 1-12 (2012).
International Preliminary Report on Patentability for International Patent Application No. PCT/EP2015/055574, dated Mar. 1, 2017 (27 pages).
Altschul et al., "Basic Local Alignment Search Tool", J Mol Biol. 215: 403-410 (1990).
Aranda et al., "Trial watch: peptide vaccines in cancer therapy," Oncoimmunology. 2(12):e26621 (2013).
Caminschi et al., "The denderitic cell subype-restricted C-type lectin Clec9A is a target for vaccine enhancement," Blood. 112(8):3264-3273 (2008) (19 pages).
Caminschi et al., "Targeting dendritic cells in vivo for cancer therapy," Front Immunol. 3(Article 13):1-13 (2012).
Cui et al., "Generation of effector CD8+ T cells and their conversion to memory T cells," available in PMC Mar. 31, 2015, published in final edited form as: Immunol Rev. 236:151-166 (2010) (27 pages).
Kreutz et al., "Targeting dendritic cells—why bother?," Blood. 121(15):2836-2844 (2013).
Pearson et al., "Improved tools for biological sequence comparison," Proc Natl Acad Sci U S A. 85:2444-2448 (1988).
Radford et al., "New generation of dendritic cell vaccines," Hum Vaccin Immunother. 9(2):259-264 (2013).
Tacken et al., "Targeted antigen delivery and activation of dendritic cells in vivo: steps towards cost effective vaccines," Semin Immunol. 23(1): 12-20 (2011).
Takai et al., "Nectins and nectin-like molecules: roles in cell adhesion, migration, and polarization," Cancer Sci. 94(8):655-667 (2003).
Wu et al., "Systematic identification of immunodominant CD8+ T-cell responses to influenza A virus in HLA-A2 individuals," Proc Natl Acad Sci U S A. 108(22):9178-9183 (2011).
Yamada et al., "Next-generation peptide vaccines for advanced cancer," Cancer Sci. 104(1):15-21 (2013).
Yoshida et al., "Molecular cloning of a novel C or gamma type chemokine, SCM-1," FEBS Lett. 360(2):155-159 (1995).
Yoshida et al., "Structure and expression of two highly related genes encoding SCM-1/human lymphotactin," FEBS Lett. 395(1):82-88 (1996).
Backer et al., "Effective collaboration between marginal metallophilic macrophages and CD8+ dendritic cells in the generation of cytotoxic T cells," Proc Natl Acad Sci U S A. 107(1):216-221 (2010).
Barnes et al., "Novel adenovirus-based vaccines induce broad and sustaine T cell responses to HCV in man," available in PMC Apr. 16, 2013, published in final edited form as: Sci Transl Med. 4(115) (2012) (22 pages).
Bechara et al., "Cell-penetrating peptides: 20 years later, where do we stand?," FEBS Lett. 587(12):1693-1702 (2013) (11 pages).
Cohn et al., "Dendritic cell-targeted vaccines," Front Immunol. 5 (Article 255):1-11 (2014).
De Gruijl et al., "Whole-cell cancer vaccination: from autologous to allogeneic tumor- and dendritic cell-based vaccines," Cancer Immunol Immunother. 57(10):1569-1577 (2008).
Dorner et al., "Plasma cell toll-like receptor (TLR) expression differs from that of B cells, and plasma cell TLR triggering enhances immunoglobulin production," Immunology. 128(4):573-579 (2009).
Koup et al., "Vaccine design for CD8 T lymphocyte responses," Cold Spring Harb Perspect Med. 1(1):a007252 (2011) (15 pages).
Kraal et al., "Langerhans' cells, veiled cells, and interdigitating cells in the mouse recognized by a monoclonal antibody," J Exp Med. 163(4):981-997 (1986).
Kramps et al., "Messenger RNA-based vaccines: progress, challenges, applications," Wiley Interdiscip Rev RNA. 4(6):737-749 (2013).
Lischke et al., "Comprehensive analysis of CD4+ T cells in the decision between tolerance and immunity in vivo reveals a pivotal role for ICOS," J Immunol. 189(1):234-244 (2012).
Merad et al., "The dendritic cell lineage: ontogeny and function of dendritic cells and their subsets in the steady state and the inflamed setting," available in PMC Dec. 6, 2013, published in final edited form as: Annu Rev Immunol. 31:563-604 (2013) (48 pages).
Milletti, "Cell-penetrating peptides: classes, origin, and current landscape," Drug Discov Today. 17(15-16):850-860 (2012).
Nussenzweig et al., "A monoclonal antibody specific for mouse dendritic cells," Proc Natl Acad Sci U S A. 79(1):161-165 (1982).
Palucka et al., "Dendritic-cell-based therapeutic cancer vaccines," Immunity. 39(1):38-48 (2013).
Paul et al., Section V:The Intersection of Innate and Adaptive Immunity. Fundamental Immunology, 7th Edition. Lippincott Williams & Wilkins, 390 (2013) (3 pages).
Porgador et al., "Localization, quantitation, and in situ detection of specific peptide-MHC class I complexes using a monoclonal antibody," Immunity. 6(6):715-726 (1997).
Probst et al., "Resting dendritic cells induce peripheral CD8+ T cell tolerance through PD-1 and CTLA-4," Nat Immunol. 6(3):280-286 (2005).
Ring et al., "Mechanistic and structural insight into the functional dichotomy between interleukin-2 and interleukin-15," available in OMC Jun. 1, 2013, published in final edited form as: Nat Immunol. 13(12):1187-1195 (2012) (16 pages).
Robert-Guroff, "Replicating and non-replicating viral vectors for vaccine development," available in PMC Dec. 1, 2008, published in final edited form as: Curr Opin Biotechnol. 18(6):546-556 (2007) (16 pages).
Saroja et al., "Recent trends in vaccine delivery systems: A review," Int J Pharm Investig. 1(2):64-74 (2011) (19 pages).
Peterson et al., "Immunization with Melan—A peptide-pulsed peripheral blood mononuclear cells plus recombinant human interleukin-12 induces clinical activity and T-cell responses in advanced melanoma," J Clin Oncol. 21(12):2342-2348 (2003).
Van Montfoort et al., "Understanding MHC class I presentation of viral antigens by human dendritic cells as a basis for rational design of therapeutic vaccines," Front Immunol. 5(Article 182):1-14 (2014).
Mostböck, "Cytokine/Antibody complexes: an emerging class of immunostimulants," Curr Pharm Des. 15(7):809-825 (2009).
Shanafelt et al., "A T-cell-selective interleukin 2 mutein exhibits potent antitumor activity and is well tolerated in vivo," Nat Biotechnol. 18(11):1197-1202 (2000).
Barr et al., Host-derived molecules as adjuvants. *Immunopotentiators in Modern Vaccines*. Elsevier Academic Press Inc., 35-55 (2006).
Boyman et al., "The role of interleukin-2 during homeostasis and activation of the immune system," Nat Rev Immunol. 12(3):180-190 (2012).
Brewer et al., Adjuvant-induced Th2- and Th1-dominated Immune Responses in Vaccination. Novel Vaccination Strategies. Wiley-VCH, 51-72 (2004).
Nair et al., "Isolation and generation of human dendritic cells," Curr Protoc Immunol. Suppl 99 (7.32.1) (2012) 23 pages).
Netea et al., "From the Th1/Th2 paradigm towards a Toll-like receptor/T-helper bias," Antimicrob Agents Chemother. 49(10):3991-3996 (2005).
Ohradanova-Repic et al., "Differentiation of human monocytes and drived subsets of macrophages and dendritic cells by the HLDA10 monoclonal antibody panel," Clin Trans Immunology. 5(1):e55 (2016) (9 pages).
Robbins et al., "Novel insights into the relationships between dendritic cell subsets in human and mouse revelaed by genome-wide expression profiling," Genome Biol. 9(1):R17 (2008) (27 pages).
Skoberne et al., "Danger signals: a time and space continuum," Trends Mol Med. 10(6):251-257 (2004).

(56) References Cited

OTHER PUBLICATIONS

Foulds et al., "Cutting Edge: CD4 and CD8 T Cells are intrinsically different in their proliferative responses," J Immunol. 168:1528-1532 (2002).
Gorak-Stolinska et al., "Activation-induced cell death of human T-cell subsets is mediated by Fas and granzyme B but is independent of TNF-alpha," J Leukoc Biol. 70:756-766 (2001).
Allan et al., "Migratory dendritic cells transfer antigen to a lymph node-resident dendritic cell population for efficient CTL priming," Immunity. 25:153-162 (2006).
Gurka et al., "Mouse conventional dendritic cells can be universally classified based on the mutually exclusive expression of XCR1 and SIRPalpha," Front Immunol. 6(Article 35):1-6 (2015).
Hartung et al., "Induction of potent CD8 T cell cytotoxicity by specific targeting of antigen to cross-presenting dendritic cells in vivo via murine or human XCR1," J Immunol. 194:1069-1079 (2015).
Hildner et al., "Batf3 deficiency reveals a critical role for CD8alpha+ dendritic cells in cytotoxic t cell immunity," Science. 322(5904):1097-1100 (2008) (9 pages).
Mitsui et al., "Polyarginin-mediated protein delivery to dendritic cells presents antigen more efficiently onto MHC class I and class II and elicits superior antitumor immunity," J Invest Dermatol. 126:1804-1812 (2006).
Bayer et al., "The IL-2/IL-2R system: from basic science to therapeutic applications to enhance immune regulation," Immunol Res. 57:197-209 (2013).
Dowling et al., "Toll-like receptors: the swiss army knife of immunity and vaccine development," Clin Transl Immunol. 5:e85 (2016).
Dubensky et al., "Adjuvants for cancer vaccines," Semin Immunol. 22(3):155-161 (2010).
Draper et al., "Viruses as vaccine vectors for infectious diseases and cancer," Nat Rev Microbiol. 8(1):62-73 (2010).
Klein, "S41. Novel CEA-targeted IL2 variant immunocytokine for immunotherapy of cancer," Journal for ImmunoTherapy of Cancer. 2(Suppl 2):18 (2014).
Kastenmüller et al., "Dendritic cell-targeted vaccines—hope or hype?," Nat Rev Immunol. 14(10):705-711 (2014).
Hennessy et al., "Targeting Toll-like receptors: emerging therapeutics?," Nat Rev Drug Discov. 9(4):293-307 (2010).
Kapsenberg, "Dendritic-cell control of pathogen-driven T-cell polarization," Nat Rev Immunol. 3(12):984-993 (2003).
Müller et al., "Cloning of ATAC, an activation-induced, chemokine-related molecule exclusively expressed in CD8+ T lymphocytes," Eur J Immunol. 25(6):1744-1748 (1995).
Moore et al., "Introduction of soluble protein into the class I pathway of antigen processing and presentation," Cell. 54(6):777-785 (1988).
Kelner et al., "Lymphotactin: a cytokine that represents a new class of chemokine," Science. 266(5189):1395-1399 (1994).
Hartung et al., "Targeting of antigen via XCR1, the lineage marker for cross-presenting dendritic cells, elicits potent CD8 cytotoxicity in vivo," Immunology. 137(Suppl 1):22 (2012).
Zhang et al., "Th1/Th2 cell differentiation and molecular signals," Adv Exp Med Biol. 841:15-44 (2014).
Speiser et al., "Molecularly defined vaccines for cancer immunotherapy, and protective T cell immunity," Semin Immunol. 22(3):144-154 (2010).
Steinman et al., "Taking dendritic cells into medicine," Nature. 449(7161):419-426 (2007).
Sander et al., "Similar frequencies and kinetics of cytokine producing cells in murine peripheral blood and spleen," Journal of Immunological Methods. 166(2):201-214 (1993).
Krop et al., "Self-renewal of B-1 lymphocytes is dependent on CD19," Eur J Immunol. 26(1):238-242 (1996).
Ulmer et al., "RNA-based vaccines," Vaccine. 30(30):4414-4418 (2012).
Smith et al., "Comparison of biosequences," Adv Appl Math. 2:482-489 (1981).
Potter et al., "Myeloma globulins of plasma-cell neoplasms in inbred mice. I. Immunoelectrophoresis of serum, with rabbit antibodies prepared against microsome fractions of the neoplasms," J Natl Cancer Inst. 26(5):1109-1137 (1961).
Higgins et al., "Clustal V: improved software for multiple sequence alignment," Comput Appl Biosci. 8(2):189-191 (1992).
De Rose et al., "Safety, immunogenicity and efficacy of peptide-pulsed cellular immunotherapy in macaques," J Med Primatol. 37(Suppl 2):69-78 (2008).
Zhang et al., "Optimizing DC vaccination by combination with oncolytic adenovirus coexpressing IL-12 and GM-CSF," Mol Ther. 19(8):1558-68 (2011).
Liang et al., "Beta-catenin mediates tumor-induced immunosuppression by inhibiting cross-priming of $CD8^+$ T cells," J Leukoc Biol. 95(1):179-90 (2014).
Notice of Reasons for Rejection for Japanese Patent Application No. 2016-558098, dated Feb. 6, 2019 (5 pages).
Durward et al., "Antigen specific in vivo killing assay using CFSE labeled target cells," J Vis Exp. 45:2250 (2010) (4 pages).
Noto et al., "Cell-based flow cytometry assay to measure cytotoxic activity," J Vis Exp. 17(82):e51105 (2013) (6 pages).
Toussi et al., "Immune Adjuvant Effect of Molecularly-defined Toll-Like Receptor Ligands," Vaccines. 2(2):323-53 (2014).
European Patent Office Communication Pursuant to Article 94(3) EPC for European Patent Application No. 15711125.3, dated Dec. 18, 2018 (9 pages).
Response to European Patent Office Communication Pursuant to Article 94(3) EPC for European Patent Application No. 15711125.3, dated Jul. 25, 2018 (10 pages).
Galibert et al., "Nectin-like Protein 2 Defines a Subset of T-cell Zone Dendritic Cells and Is a Ligand for Class-I-restricted T-cell-associated Molecule," J Biol Chem. 280(23):21955-21964 (2005).
Kroczek et al., "The role of XCR1 and its ligand XCL1 in antigen cross-presentation by murine and human dendritic cells," Front Immunol. 3:14 (2012) (5 pages).
Ohno et al., "Phase I Trial of Wilms' Tumor 1 (WT1) Peptide Vaccine with GM-CSF or CpG in Patients with Solid Malignancy," Anticancer Res. 32(6):2263-9 (2012).
Notice of Reasons for Rejection and English Translation for Japanese Patent Application No. 2016-558098, dated Nov. 28, 2019 (27 pages).

* cited by examiner

A

B

SEQUENCE LISTING

<160> NUMBER OF SEQ ID NOS: 13

<210> SEQ ID NO 1
<211> LENGTH: 114
<212> TYPE: PRT
<213> ORGANISM: Homo sapiens

<400> SEQUENCE: 1

Met Arg Leu Leu Ile Leu Ala Leu Leu Gly Ile Cys Ser Leu Thr Ala
1               5                   10                  15

Tyr Ile Val Glu Gly Val Gly Ser Glu Val Ser Asp Lys Arg Thr Cys
                20                  25                  30

Val Ser Leu Thr Thr Gln Arg Leu Pro Val Ser Arg Ile Lys Thr Tyr
            35                  40                  45

Thr Ile Thr Glu Gly Ser Leu Arg Ala Val Ile Phe Ile Thr Lys Arg
        50                  55                  60

Gly Leu Lys Val Cys Ala Asp Pro Gln Ala Thr Trp Val Arg Asp Val
65                  70                  75                  80

Val Arg Ser Met Asp Arg Lys Ser Asn Thr Arg Asn Asn Met Ile Gln
                85                  90                  95

Thr Lys Pro Thr Gly Thr Gln Gln Ser Thr Asn Thr Ala Val Thr Leu

Thr Gly

<210> SEQ ID NO 2
<211> LENGTH: 114
<212> TYPE: PRT
<213> ORGANISM: Mus musculus

<400> SEQUENCE: 2

```
Met Arg Leu Leu Leu Leu Thr Phe Leu Gly Val Cys Cys Leu Thr Pro
1               5                   10                  15
Trp Val Val Glu Gly Val Gly Thr Glu Val Leu Glu Glu Ser Ser Cys
            20                  25                  30
Val Asn Leu Gln Thr Gln Arg Leu Pro Val Gln Lys Ile Lys Thr Tyr
        35                  40                  45
Ile Ile Trp Glu Gly Ala Met Arg Ala Val Ile Phe Val Thr Lys Arg
    50                  55                  60
Gly Leu Lys Ile Cys Ala Asp Pro Glu Ala Lys Trp Val Lys Ala Ala
65                  70                  75                  80
Ile Lys Thr Val Asp Gly Arg Ala Ser Thr Arg Lys Asn Met Ala Glu
                85                  90                  95
Thr Val Pro Thr Gly Ala Gln Arg Ser Thr Ser Thr Ala Ile Thr Leu
            100                 105                 110
Thr Gly
```

<210> SEQ ID NO 3
<211> LENGTH: 114
<212> TYPE: PRT
<213> ORGANISM: Rattus norvegicus

<400> SEQUENCE: 3

```
Met Arg Leu Leu Leu Leu Thr Phe Leu Gly Val Cys Cys Phe Ala Ala
1               5                   10                  15
Trp Val Val Glu Gly Val Gly Thr Glu Val Leu Gln Glu Ser Ile Cys
            20                  25                  30
Val Ser Leu Arg Thr Gln Arg Leu Pro Val Gln Lys Ile Lys Thr Tyr
        35                  40                  45
Thr Ile Lys Glu Gly Ala Met Arg Ala Val Ile Phe Val Thr Lys Arg
    50                  55                  60
Gly Leu Arg Ile Cys Ala Asp Pro Gln Ala Lys Trp Val Lys Thr Ala
65                  70                  75                  80
Ile Lys Thr Val Asp Gly Arg Ala Ser Ala Ser Lys Ser Lys Ala Glu
                85                  90                  95
Thr Ile Pro Thr Gln Ala Gln Arg Ser Ala Ser Thr Ala Val Thr Leu
            100                 105                 110
Thr Gly
```

<210> SEQ ID NO 4
<211> LENGTH: 114
<212> TYPE: PRT
<213> ORGANISM: Human herpesvirus 8

<400> SEQUENCE: 4

```
Met Trp Ser Met Cys Trp Val Leu Arg Ala His Leu Gly Leu Leu Phe
1               5                   10                  15
Trp Val Ala Val Ile Glu Leu Cys Ala Ala Ser Gly Pro Ala Thr Ile
            20                  25                  30
```

```
Met Ala Ser Asp Cys Cys Glu Asn Ser Leu Ser Ser Ala Arg Leu Pro
         35                  40                  45

Pro Asp Lys Leu Ile Cys Gly Trp Tyr Trp Thr Ser Thr Val Tyr Cys
 50                  55                  60

Arg Gln Lys Ala Val Ile Phe Val Thr His Ser Gly Arg Lys Val Cys
 65                  70                  75                  80

Gly Ser Pro Ala Lys Arg Arg Thr Arg Leu Leu Met Glu Lys His Thr
                 85                  90                  95

Glu Ile Pro Leu Ala Lys Arg Val Ala Leu Arg Ala Gly Lys Gly Leu
                100                 105                 110

Cys Pro

<210> SEQ ID NO 5
<211> LENGTH: 17
<212> TYPE: PRT
<213> ORGANISM: Artificial
<220> FEATURE:
<223> OTHER INFORMATION: Consensus sequence
<220> FEATURE:
<221> NAME/KEY: Xaa
<222> LOCATION: (1)..(1)
<223> OTHER INFORMATION: Xaa = S or N
<220> FEATURE:
<221> NAME/KEY: Xaa
<222> LOCATION: (3)..(3)
<223> OTHER INFORMATION: Xaa = any or no amino acid
<220> FEATURE:
<221> NAME/KEY: Xaa
<222> LOCATION: (4)..(4)
<223> OTHER INFORMATION: Xaa = T or S
<220> FEATURE:
<221> NAME/KEY: Xaa
<222> LOCATION: (5)..(5)
<223> OTHER INFORMATION: Xaa = Q or A
<220> FEATURE:
<221> NAME/KEY: Xaa
<222> LOCATION: (9)..(9)
<223> OTHER INFORMATION: Xaa = V or P
<220> FEATURE:
<221> NAME/KEY: Xaa
<222> LOCATION: (10)..(10)
<223> OTHER INFORMATION: Xaa = any amino acid
<220> FEATURE:
<221> NAME/KEY: Xaa
<222> LOCATION: (11)..(11)
<223> OTHER INFORMATION: Xaa = K or R
<220> FEATURE:
<221> NAME/KEY: Xaa
<222> LOCATION: (12)..(12)
<223> OTHER INFORMATION: Xaa = I or L
<220> FEATURE:
<221> NAME/KEY: Xaa
<222> LOCATION: (13)..(13)
<223> OTHER INFORMATION: Xaa = K or I
<220> FEATURE:
<221> NAME/KEY: Xaa
<222> LOCATION: (14)..(14)
<223> OTHER INFORMATION: Xaa = any or no amino acid
<220> FEATURE:
<221> NAME/KEY: Xaa
<222> LOCATION: (15)..(15)
<223> OTHER INFORMATION: Xaa = T or G
<220> FEATURE:
<221> NAME/KEY: Xaa
<222> LOCATION: (16)..(16)
<223> OTHER INFORMATION: Xaa = any or no amino acid

<400> SEQUENCE: 5

Xaa Leu Xaa Xaa Xaa Arg Leu Pro Xaa Xaa Xaa Xaa Xaa Xaa Xaa Xaa
 1               5                  10                  15
```

Tyr

```
<210> SEQ ID NO 6
<211> LENGTH: 17
<212> TYPE: PRT
<213> ORGANISM: Artificial
<220> FEATURE:
<223> OTHER INFORMATION: consensus domain
<220> FEATURE:
<221> NAME/KEY: Xaa
<222> LOCATION: (1)..(1)
<223> OTHER INFORMATION: Xaa = R or K
<220> FEATURE:
<221> NAME/KEY: Xaa
<222> LOCATION: (6)..(6)
<223> OTHER INFORMATION: Xaa = I or V
<220> FEATURE:
<221> NAME/KEY: Xaa
<222> LOCATION: (8)..(8)
<223> OTHER INFORMATION: Xaa = K or H
<220> FEATURE:
<221> NAME/KEY: Xaa
<222> LOCATION: (9)..(9)
<223> OTHER INFORMATION: Xaa = R or S
<220> FEATURE:
<221> NAME/KEY: Xaa
<222> LOCATION: (11)..(11)
<223> OTHER INFORMATION: Xaa = L or R
<220> FEATURE:
<221> NAME/KEY: Xaa
<222> LOCATION: (12)..(12)
<223> OTHER INFORMATION: Xaa = K or R
<220> FEATURE:
<221> NAME/KEY: Xaa
<222> LOCATION: (13)..(13)
<223> OTHER INFORMATION: Xaa = I or V
<220> FEATURE:
<221> NAME/KEY: Xaa
<222> LOCATION: (15)..(15)
<223> OTHER INFORMATION: Xaa =  A or G
<220> FEATURE:
<221> NAME/KEY: Xaa
<222> LOCATION: (16)..(16)
<223> OTHER INFORMATION: Xaa =  D or S

<400> SEQUENCE: 6

Xaa Ala Val Ile Phe Xaa Thr Xaa Xaa Gly Xaa Xaa Xaa Cys Xaa Xaa
1               5                   10                  15

Pro

<210> SEQ ID NO 7
<211> LENGTH: 58
<212> TYPE: PRT
<213> ORGANISM: Artificial
<220> FEATURE:
<223> OTHER INFORMATION: consensus sequence
<220> FEATURE:
<221> NAME/KEY: Xaa
<222> LOCATION: (1)..(57)
<223> OTHER INFORMATION: Xaa = any or no amino acid

<400> SEQUENCE: 7

Xaa Gly Xaa Xaa Xaa Xaa Xaa Xaa Xaa Xaa Xaa Cys Xaa Xaa Xaa
1               5                   10                  15

Leu Xaa Xaa Xaa Arg Leu Pro Xaa Xaa Xaa Xaa Xaa Xaa Xaa Tyr
            20                  25                  30

Xaa Xaa Xaa Xaa Xaa Xaa Xaa Xaa Xaa Ala Val Ile Phe Xaa Thr
        35                  40                  45

Xaa Xaa Gly Xaa Xaa Xaa Cys Xaa Xaa Pro
    50                  55
```

```
<210> SEQ ID NO 8
<211> LENGTH: 58
<212> TYPE: PRT
<213> ORGANISM: Artificial
<220> FEATURE:
<223> OTHER INFORMATION: consensus sequence
<220> FEATURE:
<221> NAME/KEY: Xaa
<222> LOCATION: (1)..(1)
<223> OTHER INFORMATION: Xaa = V or S
<220> FEATURE:
<221> NAME/KEY: Xaa
<222> LOCATION: (3)..(3)
<223> OTHER INFORMATION: Xaa = any or no amino acid
<220> FEATURE:
<221> NAME/KEY: Xaa
<222> LOCATION: (4)..(4)
<223> OTHER INFORMATION: Xaa = E or A
<220> FEATURE:
<221> NAME/KEY: Xaa
<222> LOCATION: (5)..(5)
<223> OTHER INFORMATION: Xaa = V or T
<220> FEATURE:
<221> NAME/KEY: Xaa
<222> LOCATION: (6)..(12)
<223> OTHER INFORMATION: Xaa = any or no amino acid
<220> FEATURE:
<221> NAME/KEY: Xaa
<222> LOCATION: (14)..(14)
<223> OTHER INFORMATION: Xaa = V or E
<220> FEATURE:
<221> NAME/KEY: Xaa
<222> LOCATION: (15)..(15)
<223> OTHER INFORMATION: Xaa = any or no amino acid
<220> FEATURE:
<221> NAME/KEY: Xaa
<222> LOCATION: (16)..(16)
<223> OTHER INFORMATION: Xaa = S or N
<220> FEATURE:
<221> NAME/KEY: Xaa
<222> LOCATION: (18)..(18)
<223> OTHER INFORMATION: Xaa = any or no amino acid
<220> FEATURE:
<221> NAME/KEY: Xaa
<222> LOCATION: (19)..(19)
<223> OTHER INFORMATION: Xaa = T or S
<220> FEATURE:
<221> NAME/KEY: Xaa
<222> LOCATION: (20)..(20)
<223> OTHER INFORMATION: Xaa = Q or A
<220> FEATURE:
<221> NAME/KEY: Xaa
<222> LOCATION: (24)..(24)
<223> OTHER INFORMATION: Xaa = V or P
<220> FEATURE:
<221> NAME/KEY: Xaa
<222> LOCATION: (25)..(25)
<223> OTHER INFORMATION: Xaa = any or no amino acid
<220> FEATURE:
<221> NAME/KEY: Xaa
<222> LOCATION: (26)..(26)
<223> OTHER INFORMATION: Xaa = K or R
<220> FEATURE:
<221> NAME/KEY: Xaa
<222> LOCATION: (27)..(27)
<223> OTHER INFORMATION: Xaa = I or L
<220> FEATURE:
<221> NAME/KEY: Xaa
<222> LOCATION: (28)..(28)
<223> OTHER INFORMATION: Xaa = K or I
<220> FEATURE:
<221> NAME/KEY: Xaa
<222> LOCATION: (29)..(29)
<223> OTHER INFORMATION: Xaa = any or no amino acid
<220> FEATURE:
<221> NAME/KEY: Xaa
<222> LOCATION: (30)..(30)
<223> OTHER INFORMATION: Xaa = T or G
```

```
<220> FEATURE:
<221> NAME/KEY: Xaa
<222> LOCATION: (31)..(31)
<223> OTHER INFORMATION: Xaa = any or no amino acid
<220> FEATURE:
<221> NAME/KEY: Xaa
<222> LOCATION: (33)..(33)
<223> OTHER INFORMATION: Xaa = any or no amino acid
<220> FEATURE:
<221> NAME/KEY: Xaa
<222> LOCATION: (34)..(34)
<223> OTHER INFORMATION: Xaa = I or T
<220> FEATURE:
<221> NAME/KEY: Xaa
<222> LOCATION: (35)..(35)
<223> OTHER INFORMATION: Xaa = any or no amino acid
<220> FEATURE:
<221> NAME/KEY: Xaa
<222> LOCATION: (36)..(36)
<223> OTHER INFORMATION: Xaa = E or T
<220> FEATURE:
<221> NAME/KEY: Xaa
<222> LOCATION: (37)..(37)
<223> OTHER INFORMATION: Xaa = G or V
<220> FEATURE:
<221> NAME/KEY: Xaa
<222> LOCATION: (38)..(41)
<223> OTHER INFORMATION: Xaa = any or no amino acid
<220> FEATURE:
<221> NAME/KEY: Xaa
<222> LOCATION: (42)..(42)
<223> OTHER INFORMATION: Xaa = R or K
<220> FEATURE:
<221> NAME/KEY: Xaa
<222> LOCATION: (47)..(47)
<223> OTHER INFORMATION: Xaa = V or I
<220> FEATURE:
<221> NAME/KEY: Xaa
<222> LOCATION: (49)..(49)
<223> OTHER INFORMATION: Xaa = K or H
<220> FEATURE:
<221> NAME/KEY: Xaa
<222> LOCATION: (50)..(50)
<223> OTHER INFORMATION: Xaa = R or S
<220> FEATURE:
<221> NAME/KEY: Xaa
<222> LOCATION: (52)..(52)
<223> OTHER INFORMATION: Xaa = L or R
<220> FEATURE:
<221> NAME/KEY: Xaa
<222> LOCATION: (53)..(53)
<223> OTHER INFORMATION: Xaa = K or R
<220> FEATURE:
<221> NAME/KEY: Xaa
<222> LOCATION: (54)..(54)
<223> OTHER INFORMATION: Xaa = any or no amino acid
<220> FEATURE:
<221> NAME/KEY: Xaa
<222> LOCATION: (56)..(56)
<223> OTHER INFORMATION: Xaa = A or G
<220> FEATURE:
<221> NAME/KEY: Xaa
<222> LOCATION: (57)..(57)
<223> OTHER INFORMATION: Xaa = D or S

<400> SEQUENCE: 8

Xaa Gly Xaa Xaa Xaa Xaa Xaa Xaa Xaa Xaa Xaa Cys Xaa Xaa Xaa
 1               5                  10                  15

Leu Xaa Xaa Xaa Arg Leu Pro Xaa Xaa Xaa Xaa Xaa Xaa Xaa Tyr
            20                  25                  30

Xaa Xaa Xaa Xaa Xaa Xaa Xaa Xaa Xaa Ala Val Ile Phe Xaa Thr
        35                  40                  45

Xaa Xaa Gly Xaa Xaa Xaa Cys Xaa Xaa Pro
    50                  55
```

```
<210> SEQ ID NO 9
<211> LENGTH: 93
<212> TYPE: PRT
<213> ORGANISM: Artificial
<220> FEATURE:
<223> OTHER INFORMATION: consensus sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (22)..(23)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (33)..(34)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (46)..(47)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (57)..(63)
<223> OTHER INFORMATION: Xaa can be any naturally occurring amino acid
<220> FEATURE:
<221> NAME/KEY: misc_feature
<222> LOCATION: (65)..(75)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (80)..(81)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (85)..(86)
<223> OTHER INFORMATION: Xaa can be any naturally occurring amino acid
```

```
<220> FEATURE:
<221> NAME/KEY: misc_feature
<222> LOCATION: (89)..(89)
<223> OTHER INFORMATION: Xaa can be any naturally occurring amino acid

<400> SEQUENCE: 9

Val Gly Xaa Glu Val Xaa Xaa Xaa Xaa Cys Val Xaa Leu Xaa Thr
 1               5                  10                  15

Gln Arg Leu Pro Val Xaa Xaa Ile Lys Thr Tyr Xaa Ile Xaa Glu Gly
            20                  25                  30

Xaa Xaa Arg Ala Val Ile Phe Xaa Thr Lys Arg Gly Leu Xaa Xaa Cys
        35                  40                  45

Ala Asp Pro Xaa Ala Xaa Trp Val Xaa Xaa Xaa Xaa Xaa Xaa Asp
    50                  55                  60

Xaa Xaa Xaa Xaa Xaa Xaa Xaa Xaa Xaa Xaa Thr Xaa Pro Thr Xaa
65                  70                  75                  80

Xaa Gln Xaa Ser Xaa Xaa Thr Ala Xaa Thr Leu Thr Gly
                85                  90

<210> SEQ ID NO 10
<211> LENGTH: 93
<212> TYPE: PRT
<213> ORGANISM: Artificial
<220> FEATURE:
<223> OTHER INFORMATION: consensus sequence
<220> FEATURE:
<221> NAME/KEY: Xaa
<222> LOCATION: (3)..(3)
<223> OTHER INFORMATION: Xaa = T or S
<220> FEATURE:
<221> NAME/KEY: Xaa
<222> LOCATION: (6)..(6)
<223> OTHER INFORMATION: Xaa = L or S
<220> FEATURE:
<221> NAME/KEY: Xaa
<222> LOCATION: (7)..(7)
<223> OTHER INFORMATION: Xaa = any or no amino acid
<220> FEATURE:
<221> NAME/KEY: Xaa
<222> LOCATION: (8)..(8)
<223> OTHER INFORMATION: Xaa = E or K
<220> FEATURE:
<221> NAME/KEY: Xaa
<222> LOCATION: (9)..(9)
<223> OTHER INFORMATION: Xaa = S or R
<220> FEATURE:
<221> NAME/KEY: Xaa
<222> LOCATION: (10)..(10)
<223> OTHER INFORMATION: Xaa = any or no amino acid
<220> FEATURE:
<221> NAME/KEY: Xaa
<222> LOCATION: (13)..(13)
<223> OTHER INFORMATION: Xaa = S or N
<220> FEATURE:
<221> NAME/KEY: Xaa
<222> LOCATION: (15)..(15)
<223> OTHER INFORMATION: Xaa = any or no amino acid
<220> FEATURE:
<221> NAME/KEY: Xaa
<222> LOCATION: (22)..(22)
<223> OTHER INFORMATION: Xaa = Q or S
<220> FEATURE:
<221> NAME/KEY: Xaa
<222> LOCATION: (23)..(23)
<223> OTHER INFORMATION: Xaa = K or R
<220> FEATURE:
<221> NAME/KEY: Xaa
<222> LOCATION: (28)..(28)
<223> OTHER INFORMATION: Xaa = T or I
<220> FEATURE:
<221> NAME/KEY: Xaa
<222> LOCATION: (30)..(30)
```

```
<223> OTHER INFORMATION: Xaa = any or no amino acid
<220> FEATURE:
<221> NAME/KEY: Xaa
<222> LOCATION: (33)..(33)
<223> OTHER INFORMATION: Xaa = A or S
<220> FEATURE:
<221> NAME/KEY: Xaa
<222> LOCATION: (34)..(34)
<223> OTHER INFORMATION: Xaa = M or L
<220> FEATURE:
<221> NAME/KEY: Xaa
<222> LOCATION: (40)..(40)
<223> OTHER INFORMATION: Xaa = V or I
<220> FEATURE:
<221> NAME/KEY: Xaa
<222> LOCATION: (46)..(46)
<223> OTHER INFORMATION: Xaa = K or R
<220> FEATURE:
<221> NAME/KEY: Xaa
<222> LOCATION: (47)..(47)
<223> OTHER INFORMATION: Xaa = I or V
<220> FEATURE:
<221> NAME/KEY: Xaa
<222> LOCATION: (52)..(52)
<223> OTHER INFORMATION: Xaa = Q or E
<220> FEATURE:
<221> NAME/KEY: Xaa
<222> LOCATION: (54)..(54)
<223> OTHER INFORMATION: Xaa = K or T
<220> FEATURE:
<221> NAME/KEY: Xaa
<222> LOCATION: (57)..(57)
<223> OTHER INFORMATION: Xaa = K or R
<220> FEATURE:
<221> NAME/KEY: Xaa
<222> LOCATION: (58)..(58)
<223> OTHER INFORMATION: Xaa = any or no amino acid
<220> FEATURE:
<221> NAME/KEY: Xaa
<222> LOCATION: (59)..(59)
<223> OTHER INFORMATION: Xaa = A or V
<220> FEATURE:
<221> NAME/KEY: Xaa
<222> LOCATION: (60)..(60)
<223> OTHER INFORMATION: Xaa = I or V
<220> FEATURE:
<221> NAME/KEY: Xaa
<222> LOCATION: (61)..(61)
<223> OTHER INFORMATION: Xaa = K or R
<220> FEATURE:
<221> NAME/KEY: Xaa
<222> LOCATION: (62)..(62)
<223> OTHER INFORMATION: Xaa = T or S
<220> FEATURE:
<221> NAME/KEY: Xaa
<222> LOCATION: (63)..(63)
<223> OTHER INFORMATION: Xaa = V or M
<220> FEATURE:
<221> NAME/KEY: Xaa
<222> LOCATION: (65)..(65)
<223> OTHER INFORMATION: Xaa = G or R
<220> FEATURE:
<221> NAME/KEY: Xaa
<222> LOCATION: (66)..(66)
<223> OTHER INFORMATION: Xaa = R or K
<220> FEATURE:
<221> NAME/KEY: Xaa
<222> LOCATION: (67)..(67)
<223> OTHER INFORMATION: Xaa = A or S
<220> FEATURE:
<221> NAME/KEY: Xaa
<222> LOCATION: (68)..(68)
<223> OTHER INFORMATION: Xaa = S or N
<220> FEATURE:
<221> NAME/KEY: Xaa
<222> LOCATION: (69)..(69)
<223> OTHER INFORMATION: Xaa = T or A
<220> FEATURE:
<221> NAME/KEY: Xaa
```

```
<222> LOCATION: (70)..(70)
<223> OTHER INFORMATION: Xaa = R or S
<220> FEATURE:
<221> NAME/KEY: Xaa
<222> LOCATION: (71)..(71)
<223> OTHER INFORMATION: Xaa = K or N
<220> FEATURE:
<221> NAME/KEY: Xaa
<222> LOCATION: (72)..(72)
<223> OTHER INFORMATION: Xaa = N or S
<220> FEATURE:
<221> NAME/KEY: Xaa
<222> LOCATION: (73)..(73)
<223> OTHER INFORMATION: Xaa = M or K
<220> FEATURE:
<221> NAME/KEY: Xaa
<222> LOCATION: (74)..(74)
<223> OTHER INFORMATION: Xaa = A or I
<220> FEATURE:
<221> NAME/KEY: Xaa
<222> LOCATION: (75)..(75)
<223> OTHER INFORMATION: Xaa = E or Q
<220> FEATURE:
<221> NAME/KEY: Xaa
<222> LOCATION: (77)..(77)
<223> OTHER INFORMATION: Xaa = any or no amino acid
<220> FEATURE:
<221> NAME/KEY: Xaa
<222> LOCATION: (80)..(80)
<223> OTHER INFORMATION: Xaa = G or Q
<220> FEATURE:
<221> NAME/KEY: Xaa
<222> LOCATION: (81)..(81)
<223> OTHER INFORMATION: Xaa = A or T
<220> FEATURE:
<221> NAME/KEY: Xaa
<222> LOCATION: (83)..(83)
<223> OTHER INFORMATION: Xaa = R or Q
<220> FEATURE:
<221> NAME/KEY: Xaa
<222> LOCATION: (85)..(85)
<223> OTHER INFORMATION: Xaa = T or A
<220> FEATURE:
<221> NAME/KEY: Xaa
<222> LOCATION: (86)..(86)
<223> OTHER INFORMATION: Xaa = S or N
<220> FEATURE:
<221> NAME/KEY: Xaa
<222> LOCATION: (89)..(89)
<223> OTHER INFORMATION: Xaa = V or I

<400> SEQUENCE: 10

Val Gly Xaa Glu Val Xaa Xaa Xaa Xaa Cys Val Xaa Leu Xaa Thr
1               5                   10                  15

Gln Arg Leu Pro Val Xaa Xaa Ile Lys Thr Tyr Xaa Ile Xaa Glu Gly
            20                  25                  30

Xaa Xaa Arg Ala Val Ile Phe Xaa Thr Lys Arg Gly Leu Xaa Xaa Cys
        35                  40                  45

Ala Asp Pro Xaa Ala Xaa Trp Val Xaa Xaa Xaa Xaa Xaa Xaa Asp
    50                  55                  60

Xaa Xaa Xaa Xaa Xaa Xaa Xaa Xaa Xaa Thr Xaa Pro Thr Xaa
65                  70                  75                  80

Xaa Gln Xaa Ser Xaa Xaa Thr Ala Xaa Thr Leu Thr Gly
            85                  90

<210> SEQ ID NO 11
<211> LENGTH: 8
<212> TYPE: PRT
<213> ORGANISM: Artificial
<220> FEATURE:
<223> OTHER INFORMATION: OVA peptide
```

```
<400> SEQUENCE: 11

Ser Ile Ile Asn Phe Glu Lys Leu
1               5

<210> SEQ ID NO 12
<211> LENGTH: 333
<212> TYPE: PRT
<213> ORGANISM: Homo sapiens

<400> SEQUENCE: 12

Met Glu Ser Ser Gly Asn Pro Glu Ser Thr Thr Phe Phe Tyr Tyr Asp
1               5                   10                  15

Leu Gln Ser Gln Pro Cys Glu Asn Gln Ala Trp Val Phe Ala Thr Leu
            20                  25                  30

Ala Thr Thr Val Leu Tyr Cys Leu Val Phe Leu Leu Ser Leu Val Gly
        35                  40                  45

Asn Ser Leu Val Leu Trp Val Leu Val Lys Tyr Glu Ser Leu Glu Ser
    50                  55                  60

Leu Thr Asn Ile Phe Ile Leu Asn Leu Cys Leu Ser Asp Leu Val Phe
65                  70                  75                  80

Ala Cys Leu Leu Pro Val Trp Ile Ser Pro Tyr His Trp Gly Trp Val
                85                  90                  95

Leu Gly Asp Phe Leu Cys Lys Leu Leu Asn Met Ile Phe Ser Ile Ser
            100                 105                 110

Leu Tyr Ser Ser Ile Phe Phe Leu Thr Ile Met Thr Ile His Arg Tyr
        115                 120                 125

Leu Ser Val Val Ser Pro Leu Ser Thr Leu Arg Val Pro Thr Leu Arg
    130                 135                 140

Cys Arg Val Leu Val Thr Met Ala Val Trp Val Ala Ser Ile Leu Ser
145                 150                 155                 160

Ser Ile Leu Asp Thr Ile Phe His Lys Val Leu Ser Ser Gly Cys Asp
                165                 170                 175

Tyr Ser Glu Leu Thr Trp Tyr Leu Thr Ser Val Tyr Gln His Asn Leu
            180                 185                 190

Phe Phe Leu Leu Ser Leu Gly Ile Ile Leu Phe Cys Tyr Val Glu Ile
        195                 200                 205

Leu Arg Thr Leu Phe Arg Ser Arg Ser Lys Arg Arg His Arg Thr Val
    210                 215                 220

Lys Leu Ile Phe Ala Ile Val Val Ala Tyr Phe Leu Ser Trp Gly Pro
225                 230                 235                 240

Tyr Asn Phe Thr Leu Phe Leu Gln Thr Leu Phe Arg Thr Gln Ile Ile
                245                 250                 255

Arg Ser Cys Glu Ala Lys Gln Gln Leu Glu Tyr Ala Leu Leu Ile Cys
            260                 265                 270

Arg Asn Leu Ala Phe Ser His Cys Cys Phe Asn Pro Val Leu Tyr Val
        275                 280                 285

Phe Val Gly Val Lys Phe Arg Thr His Leu Lys His Val Leu Arg Gln
    290                 295                 300

Phe Trp Phe Cys Arg Leu Gln Ala Pro Ser Pro Ala Ser Ile Pro His
305                 310                 315                 320

Ser Pro Gly Ala Phe Ala Tyr Glu Gly Ala Ser Phe Tyr
                325                 330

<210> SEQ ID NO 13
<211> LENGTH: 37
```

```
<212> TYPE: PRT
<213> ORGANISM: Artificial Sequence
<220> FEATURE:
<223> OTHER INFORMATION: R9-SIINFEKL

<400> SEQUENCE: 13

Arg Arg Arg Arg Arg Arg Arg Arg Gly Tyr Pro Tyr Asp Val Pro
1               5                   10                  15

Asp Tyr Ala Leu Glu Gln Leu Glu Ser Ile Ile Asn Phe Glu Lys Leu
            20                  25                  30

Thr Glu Trp Thr Ser
        35
```

MEDICAMENT FOR USE IN A METHOD OF INDUCING OR EXTENDING A CELLULAR CYTOTOXIC IMMUNE RESPONSE

The present invention relates to a medicament for use in a method of extending a cellular cytotoxic immune response against an antigen-comprising protein, the method comprising the step of:

i) administering to a patient having T cells activated against an antigen a peptide-loaded major histocompatibility complex class I (MHC-I) presenting cell and an adjuvant which supports a Th-1-mediated response, wherein the peptide is derived from the antigen-comprising protein, thereby re-activating the activated T cell, wherein the peptide-loaded major histocompatibility complex class I (MHC-I) presenting cell of step i) is administered in a time frame of from 0 h to 14 days after the T cells were activated against an antigen.

The immune system protects the body against pathogens and tumor cells. To function properly, it has to discriminate between "self" and "foreign" (pathogens/tumors). The immune system detects and fights pathogens, including bacteria, viruses, parasites, fungi, and toxins. In order to allow discrimination between "self" and "foreign", all self proteins and foreign proteins (and their components) have to be "screened" by dendritic cells (DC). Some pathogens infect DC directly and can then be screened for their nature (harmless or dangerous). If pathogens invade other tissues (e.g. endothelial cells, B cells, macrophages, etc.), but not DC, these tissues undergo programmed cell death and the dead cell material is taken up by dendritic cells ("antigen transfer") and can then be screened for its nature.

Dendritic cells (and other cells) contain sensors for pathogen-associated molecular patterns (PAMP). PAMPs are components which are characteristic of pathogens (e.g. cell wall components of bacteria, or double-stranded RNA with some viruses). Once a self or foreign protein, directly or indirectly, enters the DC, it is broken down into fragments (peptides), which are then presented on the surface of DC in the context of MHC-I and MHC-II. Peptides in the context of MHC-I are recognized by $CD8^+$ T cells, peptides in the context of MHC-II by $CD4^+$ T cells, both of which activated through this process. If no additional signals are provided, this T cell activation is self-limiting and leads to T cell tolerance.

If the protein and the resulting peptides are derived from a pathogen, the DC recognizes the PAMPs of the pathogen as "dangerous" and generates a variety of additional signals. These additional signals lead to DC "maturation" (e.g. upregulation of the surface molecules CD80, CD86, CD40, CD83) and the DC can now provide to T cells strong inflammatory co-signals (Paul W. E. 2012). With certain pathogens (e.g. parasites) Th2 signals (e.g. IL-4, IL-5) are generated, with other pathogens (viruses, intracellular bacteria) Th1 signals are generated (e.g. IL-2, IL-12). The T cell response to peptides ("antigens") recognized in the context of MHC-I or MHC-II on DC is strongly shaped by these additional signals: Th2 signals lead to the generation of Th2 $CD4^+$ T cells, which mainly help B cells to produce antibodies. Th1 signals (e.g. LPS, double-stranded RNA, CpG DNA) lead to the generation of cytotoxic $CD8^+$ T cells, but also induce a Th1 $CD4^+$ (cytotoxic) T cell response. It is generally accepted that only DC are capable to instruct naïve T cells to become effector T cells (primary reaction, "priming") (Paul W. E. 2012). Therefore, only DC are capable to prime $CD8^+$ T cells to become cytotoxic cells or $CD4^+$ T cells to become helper cells or cytotoxic cells. It is generally assumed that whatever the type and route of infection, priming of T cells, and in particular CD8 T cells, has to occur by DC (Paul W. E. 2012).

There are several subpopulations of DC. In the mouse, $XCR1^+$ DC are specialized on the uptake of dead cell material and its presentation in the context of MHC-I to $CD8^+$ T cells, in the human these are the ($XCR1^+$) $CD141^+$ ($BDCA3^+$) DC (van Montfoor et al. 2014, Gurka et al. 2015). $SIRP\alpha^+$ DC in the mouse and the human are specialized on the uptake of soluble material and its presentation in the context of MHC-II to $CD4^+$ T cells (Gurka et al. 2015). In addition to these "conventional DC", there exist skin DC such as Langerhans' cells, monocyte-derived DC, and plasmacytoid DC (Merad et al. 2013). None of the functions of DC subpopulations appear to be unique and exclusive, e.g. also $SIRP\alpha^+$ DC can present antigen to $CD8^+$ T cells (Bachem et al. 2012), albeit suboptimally. Moreover, other cell types (e.g. macrophages) can transfer proteins to $XCR1^+$ DC, which then degrade the proteins and present the derived peptides to $CD8^+$ T cells (Backer et al. 2010). Although $XCR1^+$ DC are specialized on the priming of CD8 T cells, any material degraded by $XCR1^+$ DC will also be presented in the context of MHC-II and thus also prime $CD4^+$ T cells (e.g. Hartung et al. 2015). The eminent role of $XCR1^+$ DC in the priming of $CD8^+$ T cells became apparent in Batf3-KO mice, an animal model, which genetically lacks $XCR1^+$ DC (Hildner et al. 2008).

Modern protein-based vaccines designed to induce a prophylactic or therapeutic $CD8^+$ T cell immune response exploit the biology of antigen processing and presentation. Since soluble proteins are not efficiently taken up by $XCR1^+$ DC, protein antigens are being targeted to molecules expressed on the surface of DC using either monoclonal antibodies or surface receptor ligands (Tacken et al. 2011, Caminschi et al. 2012, Hartung et al. 2015). The targeted proteins are internalized into DC, degraded, and presented in the context of MCH-I and MHC-II. Since these proteinacious vaccines do not generate additional signals required for induction of $CD8^+$ effector T cells, the application of the (targeted) proteins is complemented by the addition of Th1 "adjuvants" (Dubensky et al. 2010). These adjuvants are purified PAMPs of pathogens (e.g. LPS) or compounds which mimic PAMPs, such as Polyinosinic: polycytidylic acid (poly I:C), which mimics the double-stranded RNA of certain viruses. There are a variety of PAMPS and their analogues, which induce a Th1 response of DC: e.g. LPS, CpG, or poly I:C in mice, or poly I:C, RIG-I agonists, TLR8 agonists, and others in the human. Common to all Th1 adjuvants is their capacity to effectively induce a potent Th1 response in vivo, and in particular a potent $CD8^+$ cytotoxic response, when applied together with a proteinaceous antigen.

Other vaccine approaches for induction of $CD8^+$ effector T cells, such as DNA- or RNA-based vaccines or viral or bacterial vaccination systems do not necessarily require the addition of adjuvants, since they contain PAMPs required to induce Th1 signals in DC. These vaccination systems are regarded as "self-adjuvanted".

Current knowledge indicates that vaccination antigens should be applied together with adjuvants in the same solution, ideally even physically linked, to induce an effective Th1 response in $CD4^+$ and $CD8^+$ T cells (Cohn et al. 2014). This assumption is based on the observation that protein antigen applied without adjuvant will lead to T cell tolerance (Probst et al. 2005, Lischke et al. 2012).

Certain infections, in particular viral infections, induce a strong acute $CD8^+$ T cell response in the host. In the past, it has been difficult to induce a similar response using non-life vaccines. Any type of peptide/protein-based or nucleic acid-based vaccination, adjuvanted or self-adjuvanted, only induces a rather low primary CD8 T cell response, raising the frequency of antigen-specific $CD8^+$ T cells maximally to few percent of all $CD8^+$ T cells. This is also true for DC based-vaccines, in which in vitro-generated DC were loaded in vitro with antigen in a variety of ways and then injected, often repeatedly, into the host (Palucka et al. 2013). This approach was based on the correct assumption that matured, activated DC are required to prime naïve $CD8^+$ T cells, and on the wrong assumption that matured, activated DC are required to further expand and to differentiate the primed CD8 T cells to cytotoxic cells. We have shown that, surprisingly, for this expansion phase DC are not required (see Examples 3, and 7 to 10).

A limited $CD8^+$ primary T cell response can also be observed with non-replicating viral vaccination systems based e.g. on adenoviruses, alpha-viruses or others (Robert-Guroff 2007). A limited primary $CD8^+$ T cell response is even observed with life vaccination systems, such as adenovirus-based vaccines (Barnes et al. 2012). Only if a heterologous boost is applied following these types of vaccination, this low frequency is increased.

Also the priming and boosting regimes used in therapeutic vaccines to treat cancer were rather ineffective in the past (Kastenmüller et al. 2014). Therefore, there is a need to strongly amplify any initial $CD8^+$ T cell response to overcome these limitations in order to develop effective prophylactic vaccines or to develop therapeutic vaccines against a variety of infections, or therapeutic vaccines against cancer and tumors.

The problem is solved by the present invention.

In one embodiment, the present invention relates to a medicament for use in a method of extending a cellular cytotoxic immune response against an antigen-comprising protein, the method comprising the step of:

i) administering to a patient having T cells activated against an antigen a peptide-loaded major histocompatibility complex class I (MHC-I) presenting cell and an adjuvant which supports a Th-1-mediated response, wherein the peptide is derived from the antigen-comprising protein, thereby re-activating the activated T cell, wherein the peptide-loaded major histocompatibility complex class I (MHC-I) presenting cell of step i) is administered in a time frame of from 0 h to 14 days after the T cells were activated against an antigen.

"Cellular cytotoxic immune response" is understood as Th1-type cellular cytotoxic immune reaction that can be elicited to a given antigen. This is in contrast to the response to classical vaccines which mainly address the Th2 antigen presentation pathway and mainly lead to the generation of Th2-type (neutralizing) antibodies and immune reactions.

An "Extended" cellular cytotoxic immune response is understood as a cellular cytotoxic immune response which occurs for a longer time compared to the cellular cytotoxic immune response obtained by priming with an antigen, such as by a delivery system as described for the methods of inducing a cellular cytotoxic immune response against an antigen-comprising protein as described below. For example, the response may be extended by 1, 2, 3, 4, 5, 6, 7, 8, 9, 10, 11, 12, 13, 14, or more days.

In a preferred embodiment, an extended cellular cytotoxic immune response is understood as a cellular cytotoxic immune response which is in addition amplified compared to the cellular cytotoxic immune response obtained by a "priming" with an antigen, such as by a delivery system as described for the methods of inducing a cellular cytotoxic immune response against an antigen-comprising protein as described below. For example, the response may be characterized by 2-fold or more, 3-fold or more, 5-fold or more, 10-fold or more, or 20-fold or more amplification of $CD8^+$ T cells specific for the antigen as compared to $CD8^+$ T cells specific for the antigen present after priming the patient with the antigen. Further, the response may be characterized by 100-fold or more, 1000-fold or more, 100,000-fold or more, or $10^6$-fold or more amplification of $CD8^+$ T cells specific for the antigen as compared to naïve $CD8^+$ T cells specific for the antigen. Methods for determining the $CD8^+$ T cells specific for the antigen are known to a skilled person and are for example described in the Examples.

In one preferred embodiment of the present invention, the method further comprises administering complexed interleukin 2 (IL-2cx), complexed interleukin (IL-15cx), complexed interleukin 4 (IL-4cx), complexed interleukin 7 (IL-7cx), or a IL-2 mutein, more preferably the method further comprises administering interleukin 2 (IL-2cx) or complexed interleukin 15 (IL-15cx), most preferably the method further comprises administering interleukin 2 (IL-2cx), as described below. In such embodiments of combinations of ADAS with complexed interleukin 2 (IL-2cx), complexed interleukin 15 (IL-15cx), complexed interleukin 4 (IL-4cx), complexed interleukin 7 (IL-7cx), or a IL-2 mutein, more preferably interleukin 2 (IL-2cx) or complexed interleukin 15 (IL-15cx), most preferably interleukin 2 (IL-2cx), the response may be characterized by 4-fold or more, 10-fold or more, 20-fold or more, or 100-fold or more amplification of $CD8^+$ T cells specific for the antigen as compared to $CD8^+$ T cells specific for the antigen present after priming the patient with the antigen. Further, the response may be characterized in such embodiments by 400-fold or more, 1000-fold or more, 100,000-fold or more, or $10^6$-fold or more amplification of $CD8^+$ T cells specific for the antigen as compared to naïve $CD8^+$ T cells specific for the antigen.

According to the present invention, "Antigen-Dependent Amplification System" or "ADAS" is understood as step i) of the present invention above relating to administering to the patient having T cells activated against an antigen a peptide-loaded major histocompatibility complex class I (MHC-I) presenting cell and an adjuvant which supports a Th-1-mediated response, wherein the peptide is derived from the antigen-comprising protein, thereby re-activating the activated T cell. In particular, ADAS is performed within the indicated time frame of from 0 h to 14 days after the T cells were activated against an antigen.

As shown in the Examples (see e.g. Example 6), ADAS leads to an amplification of the antigen-specific cytotoxic T cells present after priming in the patient. Therefore, the ADAS system further provides a method of amplifying a cellular cytotoxic immune response.

Therefore, in a further embodiment, the present invention relates to a medicament for use in a method of amplifying a cellular cytotoxic immune response against an antigen-comprising protein, the method comprising the step of:

i) administering to a patient having T cells activated against an antigen a peptide-loaded major histocompatibility complex class I (MHC-I) presenting cell and an adjuvant which supports a Th-1-mediated response, wherein the peptide is derived from the antigen-comprising protein, thereby re-activating the activated T cell, wherein the peptide-loaded major histocompatibility complex class I (MHC-I) presenting cell of step i) is administered in a time frame of from 0 h to 14 days after the T cells were activated against an antigen.

"Priming" according to the invention is understood as inducing a primary cellular cytotoxic immune response to a given antigen. Such priming step is typically induced in vivo in the patient; however, it is also possible to elicit such response in vitro before an adoptive transfer of cells.

We have developed a new system for extension or amplification of $CD8^+$ T cell cytotoxicity specific for a given antigen. In the examples of the present invention, the model antigen ovalbumin (OVA), or an OVA-derived peptide SIINFEKL, were recombinantly fused to the C-terminal portion of either an antibody directed to the chemokine receptor XCR1 on the surface of DC, or to the XCR1-specific chemokine ligand XCL1, and injected into a host. The targeted OVA, when applied together with a Th1 adjuvant, induced a level of 2-5% of antigen-specific, cytotoxic $CD8^+$ T cells (see Examples 1 to 5). When performing in vivo cytotoxicity assays to assess the degree of $CD8^+$ T cell priming in this system, we surprisingly noticed that not only the target cells were killed, but also the primed $CD8^+$ T cells were activated, expanded, and further differentiated into cytotoxic effectors.

From this observation we have further developed the "Antigen-Dependent Amplification System" (ADAS). The MHC-I of a variety of primary cells can be loaded with a relevant antigen by various methods, as described below in detail.

In order to examine the cellular requirements for the effectiveness of ADAS, various lymphocytic populations (splenocytes, B cells, T cells, and DC) were for comparison loaded with SIINFEKL (SEQ ID NO: 11) in vitro and injected within the optimal timeframe in mice (day 5) together with a second adjuvant (poly I:C, LPS, CpG, or equivalent). This experiment determined that all of these lymphocytic populations expressing MHC-I were capable of providing the signals necessary to continue the initial activation, expansion and functional differentiation of $CD8^+$ T cells to cytotoxic effector cells (FIG. 3B). While priming alone resulted on day 10 in 1%-5% of antigen-specific $CD8^+$ T cells within the splenic CD8 T cell population, application ADAS raised this frequency to around 15%-25%.

We further observed that the extension and amplification of the cellular cytotoxic response is surprisingly observed whenever primed antigen-specific $CD8^+$ T cells are present in the patient (see Example 6), though the best results are achieved using targeted approaches (see FIG. 6).

Therefore, any major histocompatibility complex class I (MHC-I) presenting cell is suitable for performing a method of the invention or for a medicament for use of the invention.

We have observed that ADAS is only effective in a certain time period after priming of $CD8^+$ T cells with antigen (see Example 3). When applied several days after priming, ADAS provides another activation/differentiation step to the freshly activated $CD8^+$ T cells. Thus, we have identified ADAS as a way to extend and amplify an ongoing $CD8^+$ T cell activation by administration to the patient within the indicated time scheme.

In order to examine the cellular requirements for the effectiveness of ADAS, various lymphocytic populations (splenocytes, B cells, T cells, and DC) were for comparison loaded with SIINFEKL (SEQ ID NO: 11) in vitro and injected within the optimal time frame in mice (day 5) together with a Th1 adjuvant (poly I:C, LPS, CpG, or equivalent). This experiment determined that all of these lymphocytic populations expressing MHC-I were capable of providing the signals necessary to continue the initial activation, expansion and functional differentiation of $CD8^+$ T cells to cytotoxic effector cells (FIG. 3B). While priming alone resulted on day 10 in 1%-5% of antigen-specific $CD8^+$ T cells within the splenic CD8 T cell population, application ADAS raised this frequency to around 15%-25%.

From the results obtained one can conclude that ADAS will work in vivo with any system capable to provide high enough density of peptide-loaded MHC-I molecules on the surface of lymphocytic cells or even non-lymphocytic cells.

Instead of loading MHC-I molecules with peptides externally in vitro, one could envisage systems in which cells would be fed in vitro with whole antigen-comprising protein, allowing the cells to process the antigen and present the antigenic peptides in the context of MHC-I. One could also envisage systems, in which cells would be in vitro exposed to viral systems capable of infecting the cells resulting in the expression of high amounts of a peptide in the context of MHC-I.

Further, the MHC-I bearing cells could be transfected with expression vectors coding for a given protein or peptide sequence, again resulting in an efficient presentation of peptides in the context of MHC-I.

Since whole antigen delivered to antigen-presenting cells (APC) will not only be presented in the context of MHC-I to $CD8^+$ T cells, but also in the context of MHC-II to $CD4^+$ T cells, ADAS can also be used to amplify $CD4^+$ T cell responses. For this particular amplification, the cells used for ADAS have to also express MHC-II molecules on the cell surface, which would be loaded with appropriate peptides. This loading could be done by external exposure to suitable peptides, or the MHC-II bearing cells could be transfected by expression vectors coding for a given protein or peptide sequence, again resulting in an efficient presentation of peptides in the context of MHC-II.

"The peptide is derived from the antigen-comprising protein" is understood as that the peptide sequence is part of the antigen-comprising protein sequence (i.e. is a subsequence of antigen-comprising protein sequence). In a preferred embodiment, the peptide comprises the antigen(s) or epitope(s) of interest.

A "peptide-loaded major histocompatibility complex class I (MHC-I) presenting cell" is understood as a cell which presents desired peptides on the surface of the cell by binding to MHC-I. An "antigen-comprising protein" is understood as protein which comprises an antigen or epitope of interest.

In a further embodiment, the present invention relates to a method of extending a cellular cytotoxic immune response against an antigen-comprising protein, the method comprising the step of:

i) administering to a patient having T cells activated against an antigen a peptide-loaded major histocompatibility complex class I (MHC-I) presenting cell and an adjuvant which supports a Th-1-mediated response, wherein the peptide is derived from the antigen-comprising protein, thereby re-activating the activated T cell, wherein the peptide-loaded major histocompatibility complex class I (MHC-I) presenting cell of step i) is administered in a time frame of from 0 h to 14 days after the T cells were activated against an antigen.

It was surprisingly found, that a single application of ADAS within the indicated time frame is sufficient to obtain a strong amplification and extension of the cellular cytotoxic response.

Therefore, in a preferred embodiment of the medicament for use or method of the invention, the peptide-loaded major histocompatibility complex class I (MHC-I) presenting cell of step i) is administered only once to said patient.

Therefore, in a preferred embodiment, no further administration of ADAS is performed. Therefore, in a preferred embodiment, a peptide-loaded major histocompatibility complex class I (MHC-I) presenting cell is administered to the patient only once within the indicated time frame and,
- no further administration of the peptide-loaded major histocompatibility complex class I (MHC-I) presenting cell takes place, or
- no further administration of the peptide-loaded major histocompatibility complex class I (MHC-I) presenting cell takes place within the time frame of 0 days to 14 days after the T cells were activated against the antigen.

The number of $CD8^+$ T cells recognizing a given antigenic peptide (e.g. SIINFEKL) in naïve mice is low and can be estimated to be in the order of 200 $CD8^+$ T cells. Priming of these naïve $CD8^+$ T cells by antigen containing such an antigenic peptide (e.g. OVA) in vivo requires DC and a Th1 adjuvant and will, under optimal conditions, i.e. targeting of the antigen to professional APC such as DC and B cells, increase the number of SIINFEKL-specific $CD8^+$ T cells to around 200,000. Any further substantial increase in this $CD8^+$ T cell number (i.e. amplification) necessitates a further stimulus. It is believed, without being bound to the theory, that a clearly greater number of cells which present the antigenic peptide in the context of their MHC-I in a synchronous fashion and in an inflammatory context, which can provided by administering a Th1 adjuvant (alternatively the system is self-adjuvanted) is required for the desired extension and/or amplification of the cellular cytotoxic immune response. It is further believed that these requirements are likely not met by injection of a smaller number of MHC-I bearing cells e.g. less than $1 \times 10^6$ or $1 \times 10^7$ cells in the human, such as DC or other antigen-presenting cells or any other primary cells loaded with peptide and injected locally such as s.c., into the lymph node, or into the tumor, as has been done in the past. This is the reason for the overall failure to achieve high numbers of antigen-specific cytotoxic $CD8^+$ T cells in all tumor vaccination schemes tested clinically to date.

Instead, the further stimulus for the expansion of $CD8^+$ T cells can be preferably effectively provided by a systemic injection, e.g. i.v., i.p., or intrathecally, of a high number of primary cells bearing MHC-I molecules loaded with the antigenic peptide. The high number number of MHC-I bearing primary cells and the broad immunological accessibility of the injected cells through systemic application ensure the required synchronous re-activation of the entire recently primed CD8 T cell population. If locally injected, MHC-I loaded cells are likely entrapped in the tissues and are thus not broadly accessible for the recently primed $CD8^+$ T cells. As a result, the locally injected peptide-bearing cells cannot provide a rapid and synchronous re-activation stimulus to the entire populations of recently primed $CD8^+$ T cells present in the circulation. However, if a synchronous re-activation of the entire population of primed $CD8^+$ T cells is achieved through a systemic application of MHC-I loaded primary cells, this leads to a further massive expansion of the recently primed $CD8^+$ T cells. As shown by our experiments, this type of stimulus (ADAS) can further expand the total number of antigen-specific $CD8^+$ T cells within few days from 200 000 cells to $2 \times 10^6$ and up to $10 \times 10^6$ cells, representing a 10 to 50-fold amplification (see Examples 3, 4, and 9). Similar requirements can be expected in the human immune system.

The administration of the cells may be performed by a method known to a skilled person, in particular using various administration routes. In a preferred embodiment, the cells are living cells. Typically, the cells are prepared as a suspension of cells in an aqueous solution, such as a physiologically acceptable aqueous solution, which is preferably buffered. For example, such solution is a physiologically acceptable buffered solution with physiological saline concentration.

The administration may be performed systemically, in particular intravenously, intraperitoneally, or by intrathecal injection, or alternatively, subcutaneously, or by administration into the tumor. However, as described above, systemic administration, in particular intravenous, intraperitoneal or intrathecal administration of the cells is particularly preferred. In a most preferred embodiment, the administration of the cells is intravenous administration of the cells.

In another embodiment, administration into the tumor, e.g. by injection into tumor tissue may be performed, in order to achieve a high local concentration of cells.

Therefore, in a further preferred embodiment of the medicament for use or method of the invention, the peptide-loaded major histocompatibility complex class I (MHC-I) presenting cell of step i) is administered systemically, in particular intravenously, intraperitoneally, or by intrathecal injection or alternatively, subcutaneously, or by administration into the tumor in case the patient suffers from a tumor, wherein systemic administration, in particular intravenous, intraperitoneal or intrathecal administration of the cells is particularly preferred.

In a particularly preferred embodiment, the peptide-loaded major histocompatibility complex class I (MHC-I) presenting cell of step i) is administered intravenously.

Therefore, in a yet further preferred embodiment of the medicament for use or method of the invention, the peptide-loaded major histocompatibility complex class I (MHC-I) presenting cell of step i) is administered systemically and/or as suspension in physiologically acceptable aqueous solution, which is preferably buffered.

As can be seen from the examples, various MHC-I presenting cells, such as splenocytes are suitable for this purpose. Therefore, it is not required to use a dendritic cell for this purpose.

Therefore, in a further preferred embodiment of the medicament for use or method of the invention, the peptide-loaded major histocompatibility complex class I (MHC-I) presenting cell of step i) is not a dendritic cell.

The cells are preferably from the same species as the patient. Therefore, the donor of the cells is preferably a human in case the patient is a human. The donor may be different from the patient, or may be the patient itself. In order to avoid unwanted immune responses, the donor is the patient itself, i.e. the major histocompatibility complex class I (MHC-I) presenting cell of step i) is obtained from said patient. Hence, the use of autologous cells is preferred.

Therefore, in another preferred embodiment of the medicament for use or method of the invention, the major histocompatibility complex class I (MHC-I) presenting cell of step i) is obtained from said patient.

Blood can be easily obtained from patients by methods known in the art and therefore represents a preferred source of MHC-I presenting cell to be used for generating peptide-loaded cells of the invention. A blood sample may be used directly for loading the cells in one embodiment. However, cells which do not present MHC-I, such as erythrocytes, are preferably removed from the blood sample prior to the loading of cells. In particular, peripheral blood mononucleated cells (PBMC), such as a monocyte or a lymphocytic cell and mixtures thereof are in particular suitable for this purpose.

Therefore, in a further preferred embodiment of the medicament for use or method of the invention, the MHC-I presenting cell is a blood cell, especially a peripheral blood mononucleated cell (PBMC), such as a monocyte or a lymphocytic cell.

Typically, the MHC-I presenting cells are obtained from the donor, which is preferably the patient, and are cultured only between 2 h and 3 days, more preferably between 2 h and 2 days, even more preferably between 2 h and 1 day in vitro, and are subsequently administered to the patient in accordance with the invention.

Said culturing is performed as described below in more detail in order to achieve the loading with peptides derived from the antigen-comprising protein. As described below, both external loading and internal loading methods are possible. For example, external loading may be possible by culturing in the presence of externally added peptide(s). In this embodiment, culturing in the presence of peptides for 2 h to 12 hours may be sufficient. In case of internal loading procedures, such as by using cell-penetrating peptides fused to the antigen-comprising protein, more time is preferably required to allow the cells to process the protein and present the resulting peptides in the context of MHC-I. In such embodiments, a culturing for about 10 hours to 2 days or 3 days is preferred.

Therefore, in a more preferred embodiment, the major histocompatibility complex class I (MHC-I) presenting cell of step i) obtained from said patient is cultured between 2 h and 3 days, more preferably between 2 h and 2 days in vitro. The amount of the cells to be administered may vary depending on various factors such as the antigen and patient. For example, the upper amount of cells to be administered may be limited by the amount of cells which can be obtained initially from the patient for generating the peptide-loaded major histocompatibility complex class I (MHC-I) presenting cells. Typically, between $1\times10^6$ and $4\times10^8$ cells or $5\times10^8$ cells may be administered to humans. For, example, $1\times10^7$, $3\times10^7$, $5\times10^7$, $8\times10^7$, $1\times10^8$, $2\times10^8$, $3\times10^8$, $4\times10^8$ or $5\times10^8$ cells may be administered to a human patient. However, as described above, it is preferred that higher amount of peptide-loaded major histocompatibility complex class I (MHC-I) presenting cells are administered, in particular at least $1\times10^6$, $1\times10^7$, $3\times10^7$, $5\times10^7$, or $8\times10^7$ cells, in particular, wherein the patient is a human.

It is particularly preferred that administration of the peptide-loaded major histocompatibility complex class I (MHC-I) presenting cells is performed systemically, in particular intravenously, intraperitoneally, or by intrathecal injection, and that between $1\times10^6$ and $4\times10^8$, more preferably between $1\times10^7$ and $4\times10^8$ peptide-loaded major histocompatibility complex class I (MHC-I) presenting cells are administered to said patient.

Therefore, in a yet further preferred embodiment of the medicament for use or method of the invention, between $1\times10^6$ and $4\times10^8$, preferably between $1\times10^7$ and $4\times10^8$ peptide-loaded major histocompatibility complex class I (MHC-I) presenting cells are administered to said patient.

As described above and in the examples, the administration of peptide-loaded major histocompatibility complex class I (MHC-I) presenting cell of step i) to the patient in a time frame of from 0 h to 14 days results in amplification and/or extension of the cellular cytotoxic response. Preferably, the cells are administered only once within the time frame.

Surprisingly, a single administration was found to be sufficient and preferred for achieving the desired amplification and/or extension of the cellular cytotoxic response. As could be shown in the Examples, the peptide-loaded major histocompatibility complex class I (MHC-I) presenting cell of step i) is effective when administered in a time frame of from 0 h to 14 days after the T cells were activated against an antigen, and in mice, best results are achieved in a time frame of days 5 to 9 after the initial antigenic stimulation (Example 3).

In humans, the optimal time frame may be expected to be extended, such as to from 5 days to 12 days, more preferably from 5 days to 9 days after the initial antigenic stimulation.

Further, it is preferred that ADAS is performed after some time after priming, i.e. after 48 hours ore more, more preferably 72 h or more after the initial antigenic stimulation (see Examples 3 and 11). Therefore, in a further preferred embodiment of the medicament for use or method of the invention, the time frame is from 72 h to 12 days, preferably from 5 days to 12 days, more preferably from 5 days to 9 days.

In one preferred embodiment, the cell and the second adjuvant are administered only once in a time frame of from 0 h to 14 days after the T cells were activated against the antigen.

In a further preferred embodiment, the time frame is from 48 h to 14 days, or 72 h to 14 days after the T cells were activated against the antigen.

For example, the administration is performed 48 h, 3 days, 4 days, 5 days, 6 days, 7 days, 8 days, 9 days, 10 days, 11 days, 12 days, 13 days or 14 days after the T cells were activated against the antigen. In a preferred embodiment, the time frame is from 3 days to 9 days, even more preferably of from 4 days to 8 days, or 5 days to 9 days, for example 4 days, 5 days, 6 days, 7 days, 8 days or 9 days, after the T cells were activated against the antigen.

In a further preferred embodiment, the peptide-loaded major histocompatibility complex class I (MHC-I) presenting cell of step i) is administered only once in a time frame of from 48 h to 14 days, or 72 h to 14 days after the T cells were activated against the antigen.

For example, the peptide-loaded major histocompatibility complex class I (MHC-I) presenting cell of step i) is administered only once 48 h, 3 days, 4 days, 5 days, 6 days, 7 days, 8 days, 9 days, 10 days, 11 days, 12 days, 13 days or 14 days after the T cells were activated against the antigen.

In a further preferred embodiment, the peptide-loaded major histocompatibility complex class I (MHC-I) presenting cell of step i) is administered only once in a time frame of from 3 days to 9 days, even more preferably of from 4 days to 8 days, 4 days to 9 days, or 5 to 9 days, for example 4 days, 5 days, 6 days, 7 days, 8 days, or 9 days after the T cells were activated against the antigen.

It was further surprisingly found that an amplification and/or extension of cellular cytotoxic response is again possible by performing ADAS again after the activated cytotoxic T cells have returned to the memory state (see Example 10, FIG. 10).

"Activated cytotoxic T cells have returned to the memory state" is understood as that 10% or less of the antigen-specific $CD8^+$ T cells can be detected as compared to 5 days after priming with such antigen in the patient. Memory T cells are known to the skilled person and are understood as T cells that have recognized a specific antigen and have in the past responded to said antigen and that can respond quickly and with greater strength to a re-challenge by the same antigen. The person skilled in the art is able to distinguish naïve T cells from recently activated, "primed" T cells, and recently activated, "primed" T cells from memory T cells using a variety of surface markers. In humans, suitable biomarkers are for example CD25, CD45RA, CD45RO, CD62L, CCR7, ICOS, and XCL1, such as described in Paul W. E. (2012). The skilled person is aware that biomarker pattern differs in various organs. Methods for determining antigen-specific CD8+ T cells are known to a skilled person and are for example described in Example 10.

In general, activated cytotoxic T cells have returned to the memory state after 3 weeks, preferably after 4 weeks, such as after 40 days, after the T cells were activated against the antigen.

In a further preferred embodiment of the medicament for use or method of the invention, the peptide-loaded major histocompatibility complex class I (MHC-I) presenting cell of step i) is administered only once to said patient in a time frame of from 0 h to 14 days after the T cells were activated against an antigen, and is administered one or more further times after the T cells activated against an antigen returned to the memory state. In a more preferred embodiment, the peptide-loaded major histocompatibility complex class I (MHC-I) presenting cell of step i) is administered only one further time, i.e. only once after the T cells activated against an antigen returned to the memory state. In a more preferred embodiment, the peptide-loaded major histocompatibility complex class I (MHC-I) presenting cell of step i) is administered after 3 weeks or more, preferably after 4 weeks or more after the T cells were activated against an antigen. In an even more preferred embodiment, the peptide-loaded major histocompatibility complex class I (MHC-I) presenting cell of step i) is administered only one further time, only once after 3 weeks, preferably after 4 weeks or more after the T cells were activated against an antigen. For example, the peptide-loaded major histocompatibility complex class I (MHC-I) presenting cell of step i) is administered in a time frame of from 3 weeks to 6 months or 1 year or in a time frame of from 4 weeks to 6 months or 1 year after the T cells were activated against an antigen, preferably the peptide-loaded major histocompatibility complex class I (MHC-I) presenting cell of step i) is administered only once in a time frame of from 3 weeks to 6 months or 1 year or in a time frame of from 4 weeks to 6 months or 1 year after the T cells were activated against an antigen. Therefore, also a single administration after the T cells activated against an antigen returned to the memory state is surprisingly sufficient and preferred as shown in Example 10.

Various methods are available to obtain a peptide-loaded major histocompatibility complex class I (MHC-I) presenting cell of step i) of the invention.

In one preferred embodiment, this can be done in vitro by external loading with a peptide (such as SIINFEKL as in the Examples) comprising the antigen of interest, such as in Example 3. Typically, the cells are incubated with the peptides in a suitable fluid such an aqueous solution or medium for a certain time period, such as 10 minutes to 24 hours or 48 hours, in particular 20 minutes to 12 hours.

As peptides presented in the context of MHC-I typically have a length 8, 9 or 10 amino acids, i.e. this length is required for binding of the peptides in the context of MHC-I, the peptides used for external loading preferably have this length.

Therefore, in a further preferred embodiment of the medicament for use or method of the invention, the peptide-loaded major histocompatibility complex class I (MHC-I) presenting cell of step i) is obtained by incubating at least one major histocompatibility complex class I (MHC-I) presenting cell with said peptide(s) in vitro.

In case of externally loading cells in vitro, the peptide sequence may be chosen by methods known in the art. Externally loading cells in vitro can be performed by methods known in the art, e.g. by providing an aqueous solution of the peptides, adding the solution to the cells, which are preferably in a buffered solution or medium, incubating the cells with the peptides as to achieve a high saturation of the MHC-I and/or MHC-II with the respective peptide, and optionally washing the cells, e.g. with an aqueous solution.

In one preferred embodiment, cells are loaded in vitro with one (1) peptide which has a sequence which is a subsequence of the antigen-comprising protein and which comprises the antigen or epitope. For example, an aqueous solution comprising one such peptide may be added in vitro to a cell population, which is preferably a cell population obtained from the patient. Alternatively, a mixture of 2, 3, 4, 5, 6, 7, 8, 9, 10 or more different peptide loaded-cell major histocompatibility complex class I (MHC-I) presenting cell populations may be used, wherein the cells are loaded with different peptides. Preferably, the cells are obtained from the patient.

Such mixture of cells may be obtained by incubating a suitable cell population, like PBMC cells, with a mixture of 2, 3, 4, 5, 6, 7, 8, 9, 10 or more different peptides, thereby obtaining cells loaded with different peptides in the context of MHC-I. Alternatively, separate cell populations, for example 2, 3, 4, 5, 6, 7, 8, 9, 10 or more cell populations, may be incubated in vitro with different peptides, for example 2, 3, 4, 5, 6, 7, 8, 9, 10 or more different peptides. Thereby, separate major histocompatibility complex class I (MHC-I) presenting cell populations each loaded with a different peptide are thereby obtained. The different peptide loaded-cell major histocompatibility complex class I (MHC-I) presenting cell populations may be administered separately, or a mixture of the different peptide loaded-cell major histocompatibility complex class I (MHC-I) presenting cell populations may be prepared, which may then be administered to the patient.

In case different peptides are employed, in particular if 2, 3, 4, 5, 6, 7, 8, 9, 10 or more different peptides are employed, such peptides may be derived from the same or a different antigen-comprising protein. In a preferred embodiment, 2, 3, 4, 5, 6, 7, 8, 9, 10 or more different peptides derived from one tumor antigen may be used. This means, that the sequence of each peptide is a subsequence of the tumor antigen. The sequences of such different peptides may be overlapping or non-overlapping. In a further embodiment, 2, 3, 4, 5, 6, 7, 8, 9, 10 or more different peptides derived from 2, 3, 4, 5, 6, 7, 8, 9, 10 or more different tumor antigen may be used. In such embodiment, the different tumor antigens are related to the same or different tumor, preferably to the same tumor. In a further preferred embodiment, 2, 3, 4, 5, 6, 7, 8, 9, 10 or more different peptides derived from one infectious pathogen antigen may be used. This means, that the sequence of each peptide is a subsequence of the antigen of the pathogen. The sequences of such different peptides may be overlapping or non-overlapping. In a further embodiment, 2, 3, 4, 5, 6, 7, 8, 9, 10 or more different peptides derived from 2, 3, 4, 5, 6, 7, 8, 9, 10 or more different pathogen antigens may be used. In such embodiment, the different pathogen antigens are related to the same or different pathogen, preferably to the same pathogen.

Preferably, a peptide sequence of a length of 8, 9 or 10 amino acids is chosen, as peptides presented by MHC-I are typically of this length.

HLA alleles are extremely polymorphic. Therefore, the peptide loaded is preferably a peptide presented by a frequent HLA allele. Therefore, in humans, a peptide presented by the most frequent allele HLA-A2 is particularly preferred. Alternatively, peptides presented by HLA-A1, -A3, -B7, -B35, which are the alleles relevant for individuals of Caucasian origin may be used. HLA-A24 may be used for Asian individuals and HLA-A30 for African individuals.

Several suitable tumor-related peptides are described in Speiser and Romero (Seminars in Immunology 22 (2010) 144-154) and references therein. Most of them are HLA-A2 restricted, for example peptides derived from Melan-A/MART-1, one of the gp100 epitopes and tyrosinase for the melanocyte differentiation antigens; prostate surface antigen and PSAP for prostate; carcinoembryonic antigen and MUC-1 for mucosal tumors; HER-2/neu for breast carcinoma; G250 for renal cell carcinoma; the PR1 shared by two myeloid leukemia associated antigens, PR3 and neutrophil elastase which are normally expressed in granulocytes and overexpressed in myeloid leukemia cells; the shared tumor-specific antigens MAGE-A and NY-ESO-1 for various tumor types; and the overexpressed proteins survivin and telomerase. Suitable Influenza A-derived peptides are described in Wu et al (supra).

Therefore, in a further embodiment, the peptide derived from the antigen-comprising protein is a peptide presented by a MHC-I, preferably by allele HLA-A2, HLA-A1, HLA-A3, HLA-B7, HLA-B35, HLA-A24, or HLA-A30, more preferably by allele HLA-A2. Methods for identifying such peptides are described and summarized in Wu et al. (PNAS, 2011, 108(22): 9178-9183). For example, the systematic identification approach of Wu et al. (supra) may be used, or suitable algorithms described therein.

Therefore, in another preferred embodiment of the medicament for use or method of the invention, the peptide derived from the antigen-comprising protein has a length of 8, 9 or 10 amino acids and/or is a peptide presented by a MHC-I, preferably by allele HLA-A2, HLA-A1, HLA-A3, HLA-B7, HLA-B35, HLA-A24, or HLA-A30, more preferably by allele HLA-A2.

It is preferred that the peptide loaded onto the major histocompatibility complex class I (MHC-I) presenting cell comprises the antigen or epitope of interest in order to elicit the desired response.

Therefore, in a further preferred embodiment of the medicament for use or method of the invention, the at least one peptide comprises the antigen or epitope.

As an antigen-comprising protein may contain more than one antigen or epitope, the cells may be loaded with two or more different peptides, which may comprise different antigens or epitopes. Also, the two or more peptides may contain the same antigen or epitope, but may have a different length.

Alternatively, the loading can be performed in vitro by "internal" loading of the cells with antigen in a variety of ways, such as, but not limited to electroporation, transfection, or infection in vitro prior to (re-)administration into the primed host together with a Th1 adjuvant (see Examples 1 to 5). This procedure results in a strong amplification and expansion of the primed $CD8^+$ T cells and triggers their further differentiation to cytotoxic cell, as shown in the Examples.

External loading of the MHC-I in ADAS with peptides poses certain limitations in the human due to the heterogeneity of MHC-I molecules in the human population. As a result, different peptides derived from the same antigen (e.g. nucleoprotein of influenza of TRP-1 from melanoma) are preferably to be used in different individuals for ADAS. This problem can be overcome with an "internal" loading of the MHC-I bearing cells used for ADAS which whole protein or a long peptide containing many antigenic epitopes. To this end, the unprocessed antigen-comprising protein or a fragment thereof comprising the antigen(s) or epitope(s) is introduced into the MHC-I bearing cells, whereupon it is enzymatically broken down ("processed") into a plurality of different peptides, which are then presented on the surface in the context of MHC-I (and MHC-II).

The transport of the unprocessed antigen-comprising protein or a fragment thereof comprising the antigen into the cell can be achieved with a variety of physical or chemical methods which are known to a skilled person, such as, but not limited to, electroporation, forced endocytosis, injection, and cell-penetrating peptides.

Another way to internally load MHC-I bearing cells is to load them with nucleic acids, such as DNA or RNA, coding for the antigen-comprising protein or a fragment thereof comprising the antigen. The introduction of nucleic acid into the cells can be by any chemical, physical, or biological means, such as, but not limited to electroporation, injection, transfection, or infection with organisms recombinantly modified to carry the nucleic acid sequence coding for the antigen-comprising protein or a fragment thereof comprising the antigen. Once the coded protein is expressed by the cell machinery, it is processed and presented on the cell surface in the context of MHC-I (and MHC-II) and the cell becomes a peptide-loaded cell in accordance with the present invention. The skilled person is aware of suitable DNA and RNA constructs and DNA- or RNA-based expression systems. For example, suitable RNA constructs or RNA-based expression systems preferably further comprise elements which allow for translation and therefore expression of a protein in the cell of interest. For example, suitable DNA constructs or DNA-based expression systems preferably further comprise elements which allow for transcription and translation and therefore expression of a protein in the cell of interest. Optionally, such systems further comprise suitable elements which allow for replication of the DNA or RNA construct, or DNA- or RNA-based expression system, respectively.

For example viral systems, and non-viral expression systems, which are capable of expressing a protein of interest (in this case the antigen-comprising protein or a fragment thereof comprising the antigen) in the major histocompatibility complex class I (MHC-I) presenting cell, are suitable for this purpose.

Therefore, in a further preferred embodiment of the medicament for use or method of the invention, the peptide-loaded major histocompatibility complex class I (MHC-I) presenting cell of step i) is obtained by:

applying a physical, chemical or biological method for introducing an antigen-comprising protein or a fragment thereof comprising the antigen, or a nucleic acid encoding the antigen-comprising protein or a fragment thereof comprising the antigen into at least one major histocompatibility complex class I (MHC-I) presenting cell, allowing the at least one cell to express the antigen-comprising protein or a fragment thereof comprising the antigen into at least one major histocompatibility complex class I (MHC-I) presenting cell in case of a nucleic acid, and allowing the at least one cell to process the antigen and present the peptides in the context of MHC-I.

In particular, following embodiments are preferred for obtaining such cell:
a. incubating at least one major histocompatibility complex class I (MHC-I) presenting cell with the antigen-comprising protein or a fragment thereof comprising the antigen, and allowing the at least one cell to process the antigen and present the peptides in the context of MHC-I, or b. exposing at least one major histocompatibility complex class I (MHC-I) presenting cell to a viral system which is capable of (i) infecting said cell and (ii) expressing the antigen-comprising protein or a fragment thereof comprising the antigen in the cell, and allowing the at least one cell to process the antigen-comprising protein antigen or fragment thereof comprising the antigen, and allowing the at least one cell to present the peptide(s) in the context of MHC-I, or c. transfecting at least one major histocompatibility complex class I (MHC-I) presenting cell with DNA, or RNA, or a DNA- or RNA-based expression system which is comprising a nucleic acid coding for the antigen-comprising protein or a fragment thereof comprising the antigen, and allowing the at least one cell to express and process the antigen-comprising protein antigen or fragment thereof comprising the antigen, and allowing the at least one cell to present the peptides in the context of MHC-I, or d. incubating at least one major histocompatibility complex class I (MHC-I) presenting cell with a compound comprising a cell-penetrating peptide (CPP) and the antigen-comprising protein or a fragment thereof comprising the antigen, and allowing the at least one cell to process said compound, and allowing the at least one cell to present the peptides in the context of MHC-I.

A compound comprising a cell-penetrating peptide (CPP) and the antigen-comprising protein or a fragment thereof comprising the antigen is understood as a compound wherein a cell-penetrating peptide (CPP) is chemically linked the antigen-comprising protein or a fragment thereof comprising the antigen, optionally by a suitable linker. Such linker may for example be a peptide linker, for example a peptide linker having a length of 1 to 50, preferably 1 to 20, more preferably 1, 2, 3, 4, 5, 6, 7, 8, 9, or 10 amino acids, however, also other linkers can be used. In one preferred embodiment, the compound is a fusion protein comprising a cell-penetrating peptide (CPP) and the antigen-comprising protein or a fragment thereof comprising the antigen, which fusion protein may optionally contain a suitable peptide linker. In one embodiment, the compound is a fusion protein consisting of a cell-penetrating peptide (CPP) and the antigen-comprising protein or a fragment thereof comprising the antigen, wherein the cell-penetrating peptide (CPP) and the antigen-comprising protein or a fragment thereof comprising the antigen are linked via a peptide bond. In a preferred embodiment, the cell-penetrating peptide (CPP) is located N-terminally or C-terminally to the antigen-comprising protein or a fragment thereof comprising the antigen in the compound.

In case of embodiment c., nucleic acids are employed. Nucleic acids represent in many cases self-adjuvanted systems. Therefore, no additional administration of an adjuvant which supports a Th-1-mediated response is obligatory in such embodiment.

A "cell-penetrating peptide" (CPP), also known as protein transduction domain (PTD), membrane translocating sequence (MTS), is understood as a peptide of 3 to 40 amino acids, which is able to penetrate into almost any cell. Preferably, the cell-penetrating peptide is highly cationic and/or contains a high content of arginine and/or lysine amino acids. A preferred cell-penetrating peptide is R9, which is a peptide consisting of 9 Arginine residues. Such peptide was successfully used for internally loading splenocytes with long OVA peptides (Example 7, FIG. 7).

In a further preferred embodiment of the medicament for use or method of the invention, the patient is a human.

In a further preferred embodiment of the medicament for use or method of the invention, the method of extending a cellular cytotoxic immune response is for prophylactically treating or treating a tumor and/or an infection, and/or wherein the patient is immunocompromised or immunosuppressed.

The extension and/or amplification of a cellular cytotoxic immune response is in particular for prophylactically treating or treating a tumor. The patient may be suffering from tumor, or, in case of prophylactic treatment, is not suffering from a tumor, but is to be protected from a respective infection or tumor disease. Therefore, the prophylactic treatment preferably relates to an immunization against said tumor.

In one preferred embodiment, the tumor is selected from a virally induced cancer, in particular hepatitis B- or hepatitis C-induced hepatocellular carcinoma, a human papillomavirus-induced cancer, e.g. cervical, vaginal, vulvar, oropharyngeal cancer, an Epstein-Barr virus induced cancer, Kaposi sarcoma, and adult T-cell leukemia (HTLV1).

For virally induced cancers, the antigen-comprising protein is preferably a protein of the virus.

In a further preferred embodiment, the tumor is a leukemia, in particular selected from AML, CML, CMML, and MDS.

In a yet further preferred embodiment, the tumor is a solid cancer which expresses one or more cancer-specific antigens, such as breast cancer, prostate cancer, lung cancers, including lung squamous cell cancer and non-small cell lung cancer, skin cancers, such as melanoma, bladder cancer, oesophageal adenocarcinoma and squamous cell cancer, colorectal cancer, intestinal adenocarcinoma, kidney cancers, including renal cell carcinoma, ovarian cancers, neuroblastoma, glioma, multiple myeloma, pancreatic cancer, and sarcoma.

The use for the prophylactic treatment of a tumor, in particular immunization against a tumor, of a human is particularly preferred.

In a further embodiment, the extension and/or amplification of a cellular cytotoxic immune response is in particular for prophylactically treating or treating an infection. The patient may be suffering from an infection, or, in case of prophylactic treatment, is not suffering from an infection, but is to be protected from a respective infection. Therefore, the prophylactic treatment preferably relates to an immunization against said infection.

In a further preferred embodiment, the infection is an infection by a pathogen, in particular by an infectious pathogen selected from bacteria, viruses, parasites and fungi. Preferably, an infectious pathogen is selected from malaria, tuberculosis, *leishmania* and a virus, in particular a virus selected from an orthomyxovirus, influenza virus, hepatitis A virus, hepatitis B virus, hepatitis C virus, a lentivirus, in particular HI-Virus, cytomegalovirus, a herpes virus, a papillomavirus, a bunyavirus, a calicivirus, a filovirus, a flavivirus, and a respiratory virus, more preferably the infectious pathogen is a virus selected from a hepatitis C virus, hepatitic B virus, a papillomavirus, a paramyxovirus, and a respiratory virus. For viral infections, the antigen-comprising protein is preferably a protein of the virus.

Suitable antigen-comprising proteins are known to the skilled person. The choice of an antigen-comprising protein depends on the medical indication to be considered. For the prophylactic treatment or treatment of a non-virally induced tumor, the antigen-comprising protein is a suitable tumor antigen. For the prophylactic treatment or treatment of an infection by a pathogen, the antigen-comprising protein is a suitable antigen of the pathogen.

For example, numerous suitable antigen-comprising proteins and peptides comprising antigens in the context of tumor diseases are known. Moreover, suitable peptides as vaccines are described, as e.g. summarized in Aranda et al., OncoImmunology 2:12, e26621; December 2013 for solid neoplasms, including glioma, lung carcinoma, sarcoma, melanoma, esophageal squamous cell carcinoma, gastric cancer, hepatocellular carcinoma, pancreatic cancer, colorectal carcinoma, renal cell carcinoma, prostate cancer, ovarian carcinoma, gynecologic malignancies, and various other tumors. The antigen-comprising proteins specifically targeted in these clinical trials encompass cancer-testis antigens such as NY-ESO-1, TTK protein kinase (also known as MOS), lymphocyte antigen 6 complex, locus K (LY6K, best known as URLC10), insulin-like growth factor 2 mRNA binding protein 3 (IGF2BP3, best known as IMP3), ring finger protein (RNF43), and translocase of outer mitochondrial membrane 34 (TOMM34); carcinoembryonic antigens like glypican-3; differentiation antigens such as melan-A (MLANA) and premelanosome protein (PMEL, best known as gp100); tumor-restricted antigens, such as the SYT-SSX fusion (which is selectively expressed by synovial sarcomas as a result of a t(X;18)(p11;q11) chromosomal translocation); as well as so-called "shared tumor-associated antigens" (antigens that are overexpressed by malignant cells but also produced in normal amounts by one or several healthy tissues), including vascular endothelial growth factor receptor 1 (VEGFR1) and VEGFR2, survivin, Wilms tumor 1 (WT1), telomerase reverse transcriptase (TERT), and p53. Such proteins are therefore suitable antigen-comprising proteins in the context of tumor. A further summary on peptide vaccines in cancer is Yamada et al., Cancer Sci, 2013, 104(1):15-21.

Suitable antigen-comprised protein involved in tumor diseases are known in the art. As described e.g. in Tacken and Figdor (Tacken P. J., Figdor C. G.; Targeted antigen delivery and activation of dendritic cells in vivo: Steps towards cost effective vaccines. Semin. Immunol., 2011, 23(1):12-20), ideal tumor antigens are those known as shared tumor-specific antigens because they are selectively expressed in tumor cells, of various histotypes, and not in MHC-expressing normal tissues. Examples of such type of antigens are the MAGE-A or NY-ESO-1 antigens. The various members in this category of antigens are expressed at variable proportions depending on the tumor type and the disease stage. Thus, vaccines based on these antigens require selection of patients bearing tumors that express the target antigen. Another category of tumor antigens that are deemed valuable for vaccine development are those derived from oncogenic proteins which are overexpressed in tumors. Bona fide non-self tumor antigens are derived from two major sources: viral antigens in the case of tumors of oncogenic viral origin such as cervical carcinomas caused by HPV infection, and somatic mutations.

In case of extending or amplifying a cellular cytotoxic immune response in a patient suffering from an infection or a patient to be prophylactically treated regarding an infectious disease (or infection), suitable antigen-comprised proteins of a pathogen may be used, in particular a pathogen selected from malaria, tuberculosis, *leishmania* or a virus, in particular a virus selected from an orthomyxovirus, influenza virus, hepatitis A virus, hepatitis B virus, chronic hepatitis C virus, a lentivirus, in particular HI-Virus, cytomegalovirus, a herpes virus, a papillomavirus, a bunyavirus, a calicivirus, a filovirus, a flavivirus, or a respiratory virus. In an even more preferred embodiment, antigen-comprising protein is a protein of a virus selected from a hepatitis C virus, a papillomavirus, a paramyxovirus, or a respiratory virus.

Viruses, in particular RNA viruses, typically exhibit a high mutation rate. However, there are typically conserved regions found in particular in genomic segments encoding non-structural and/or internal proteins, such regions encoding a viral polymerase or a nucleoprotein. Such regions are unsuitable for classical vaccination technologies, as such conserved proteins are not exposed on the viral coat surface. In contrast, such antigen-comprised proteins and/or antigen comprised in the protein may be used in the medicament for use according to the invention.

In a preferred embodiment, the antigen-comprising protein and/or antigen comprised in the protein of a virus is conserved.

In a further preferred embodiment, the antigen-comprising protein is a non-structural protein and/or the antigen is comprised in a non-structural and/or internal protein.

In a yet further preferred embodiment, the antigen-comprising protein is a protein of an RNA virus.

A "non-structural" or "internal" protein is a protein which is not part of the coat or envelope of a virus particle.

In a further embodiment, the antigen is comprised in the protein in step i) is immunodominant. Immunodominant means that, although many pMHC complexes are available for a certain pathogen, T-cell responses are reproducibly focused on one or few key antigens, and such the antigen is one such key antigens.

Suitable antigen-comprising proteins and antigens of influenza A virus are for example described in Wu et al. (PNAS, 2011, 108(22): 9178-9183), and encompass NP (nucleoprotein), basic polymerase 1 and M1.

Further, the present method is in particular beneficial for prophylactically treating, such as immunizing, or treating a tumor and/or an infection, wherein the patient is immunocompromised or immunosuppressed.

Patients may be immunocompromised or immunosuppressed due to transplantation, such as bone marrow transplantation, a chemotherapy, such as cancer chemotherapy, aglucocorticoid therapy, leukemia, AIDS, a glucocorticoid therapy, or an immunesuppressive therapy, for example for treating an autoimmune disease. Such patients will in particular benefit from the medicaments for use and methods of the present invention.

As shown in Example 6, the method of the invention or medicament for use of the invention successfully extends and amplifies the cellular cytotoxic response for a variety of different "priming" steps, which initially activate T cells against a given antigen.

In particular, methods employing a delivery system comprising
(a) a molecule binding to a receptor on the surface of an antigen-presenting cell,
(b) said antigen-comprising protein bound to molecule of (a) and
wherein upon binding of the molecule of (a) to the receptor, the protein of (b) is internalized and processed in the antigen-presenting cell and the antigen comprised in the protein is presented on the surface of the antigen-presenting cell, are suitable for activating a T cell specific for the antigen in the patient. For example, the antigen-presenting cell (APC) being a dendritic cell turned out to be particularly useful. However, a B cell was also successfully used as antigen-presenting cell.

Also, a plurality of receptors on the surface of an antigen-presenting cell were successfully used in Example 6. In particular, successful priming was achieved by using XCR1 as receptor on the surface of dendritic cell, DCIR2 on the surface of a dendritic cell, and CD19 on the surface of a B cell (see FIG. 6), followed by amplification and/or extension of the cellular cytotoxic response according to the present invention.

Therefore, in a further preferred embodiment of the medicament for use or method of the invention, said T cells were activated against said antigen by:
(1) administering to said patient a delivery system comprising
   (a) a molecule binding to a receptor on the surface of an antigen-presenting cell,
   (b) said antigen-comprising protein bound to molecule of (a) and wherein upon binding of the molecule of (a) to the receptor, the protein of (b) is internalized and processed in the antigen-presenting cell and the antigen comprised in the protein is presented on the surface of the antigen-presenting cell, thereby activating a T cell in the patient, and
(2) administering a further adjuvant which supports a Th-1-mediated response.

Also further methods for "priming" or initial activation of T cells are possible and were successfully used.

For example, T cell activation by adoptive transfer of T cells is possible and was successfully used. Adoptive transfer of cells is known to a skilled person and is understood as transfer of cells, back into the same patient or into a new recipient host with the goal of transferring the immunologic functionality and characteristics into the new host.

Therefore, the T cells are activated against said antigen in such embodiment by:
(1) activating one or more T cells obtained from said patient in vitro with an antigen-comprising protein or a fragment thereof comprising the antigen, and
(2) re-transferring one or more T cells obtained in step (1) to said patient, and
(3) optionally administering a further adjuvant which supports a Th-1-mediated response.

In case of adoptive transfer, the peptide-loaded major histocompatibility complex class I (MHC-I) presenting cell of step i) is administered in a time frame of from 0 h to 14 days after the T cells were activated against an antigen by re-transferring one or more T cells obtained in step (1) to said patient; i.e. the time frame is calculated from adoptive transfer of the one or more T cells obtained in step (1) to said patient.

In adoptive T cell therapy, antigen-specific $CD8^+$ T cells, e.g. T cells directed to CMV antigens or any other pathogenic antigens or T cells directed to defined tumor antigens, are enriched in vitro from the PBMC of a patient. This is done, for example, using IFN-γ secretion capture after in vitro stimulation of the PBMC with an antigenic peptide or protein from this pathogen (e.g. CMV) or tumor, combined with magnetic cell sorting. The enriched antigen-specific $CD8^+$ T cells are then further stimulated by addition of whole antigen or, more often, peptide antigen, and then expanded in vitro. After expansion, the activated $CD8^+$ T cells are then re-injected into the patient in order to achieve the desired effect, such as treating the patient by e.g. elimination of the pathogen or tumor. Currently, the re-injected $CD8^+$ T cells have a short life span in vivo, their capacity to secrete IFN-γ is limited, and their cytotoxic potential is suboptimal. We have surprisingly found that this shortcoming of the adoptive T cell therapy can be very substantially improved using the ADAS procedure, as shown in Example 11.

Therefore, adoptive transfer of cells is a method known to a skilled person. For example, PBMC cells from a blood sample obtained from the patient may be incubated in vitro with a peptide comprising the antigen of interest. Activation of one or more $CD8^+$ T cells within the PBMC cells is then detected by detecting IFN-gamma secretion/production. Preferably, such IFN-γ-producing/secreting cells are further enriched, and/or cultivated and/or expanded by methods known in the art. A cell probe comprising one or more activated T cells is subsequently re-transferred to said patient, for example by injection.

For activating a T cell against an antigen in vitro before adoptive transfer, a further adjuvant which supports a Th-1-mediated response may either be administered or not be administered to the patient, preferably a further adjuvant which supports a Th-1-mediated response is administered to the patient.

T cell activation in vitro before adoptive transfer of T cells is in particular useful for prophylactically treating or treating an immunocompromised or immunosuppressed patient.

Alternatively, the T cells were activated against said antigen in one embodiment by a non-targeted approach and/or an approach employing nucleic acids. For example, it could be shown that even with high amounts of non-target antigen-comprising proteins, a sufficient priming of antigen-specific T cells was obtained, which could then be amplified and extended according to the present invention (Example 6, FIG. 6).

In case of antigen-comprising protein administered in a non-targeted approach, the antigen-comprising protein may be administered as a suitable formulation optionally further containing pharmaceutically acceptable excipients, such as a optionally buffered aqueous saline solution. Such formulation may contain suitable carriers such as a liposome or nanoparticle.

Therefore, the T cells are activated against said antigen in such embodiment by:
(1) administering to said patient a delivery system selected from:
(a) a pharmaceutical composition comprising the antigen-comprising protein or a fragment thereof comprising the antigen, preferably a pharmaceutical composition comprising a carrier, in particular nanoparticle or liposome, bound to the antigen-comprising protein or a fragment thereof comprising the antigen,
and
(b) a nucleic acid
   which comprises a nucleic acid sequence encoding said antigen-comprising protein or a fragment thereof comprising the antigen, and which is capable of expressing said antigen-comprising protein or a fragment thereof comprising the antigen in said patient,
preferably wherein
the nucleic acid is DNA or RNA, and/or
the nucleic acid is a viral system, such as an attenuated virus, non-replicating viral system, targeted viral vaccine system or non-targeted viral vaccine system, or
the nucleic acid is a non-viral expression system,
thereby activating at least one T cell,
and
(2) administering a further adjuvant which supports a Th-1-mediated response.

Delivery systems relating to nucleic acids are described above. Suitable viral systems, such as an attenuated virus, non-replicating viral system, targeted viral vaccine system or non-targeted viral vaccine system, and non-viral expression systems are known to a skilled person and are for example disclosed in Robert-Guroff et al. 2007, Barnes et al. 2012). Nucleic acids represent in many cases self-adjuvanted systems. Therefore, no additional administration of an adjuvant which supports a Th-1-mediated response is required in such embodiment. Rather, the delivery system itself represents both an adjuvant which supports a Th-1-mediated response and a delivery system for activating a T cell.

In a further preferred embodiment of the medicament for use or method of the invention, the antigen-presenting cell is selected from a dendritic cell, a macrophage, and a B cell. For example, efficient priming was observed for targeting dendritic cells, in particular a XCR1$^+$ (CD141+) dendritic cell, and a SIRPα$^+$ dendritic cell, and B cell (see Example 6). In a more preferred embodiment of the medicament for use or method of the invention, the antigen-presenting cell is a dendritic cell (DC), preferably selected from a XCR1$^+$ (CD141+) dendritic cell, a SIRPα$^+$ dendritic cell, a monocyte-derived dendritic cell, a skin dendritic cell, such as a Langerhans' cell, and a plasmacytoid dendritic cell (pDC). For example, efficient priming was observed for dendritic cells, in particular a XCR1$^+$ (CD141+) dendritic cell, and a SIRPα$^+$ dendritic cell (Example 6).

For preferred embodiments of delivery systems, it is referred to the method of inducing a cellular cytotoxic response described in detail below.

In the method of extending a cellular cytotoxic immune response against an antigen-comprising protein, an adjuvant which supports a Th-1-mediated response is administered in step i).

An adjuvant is an agent which modifies the effect of other agents while having few if any direct effects when given by itself. In pharmacology, adjuvants are drugs that have few or no pharmacological effects by themselves, but may increase the efficacy or potency of other drugs when given at the same time. In immunology an adjuvant is an agent which, while not having any specific antigenic effect in itself, may stimulate the immune system, increasing the response to a vaccine. The adjuvants used in the present invention are supporting a Th1 response. An "adjuvant which supports a Th-1-mediated response" or "Th1 adjuvant" is understood as an adjuvant which is capable to induce IL-12 in DC, and leads to the secretion of IL-2, IFN-γ and TNF-α by responsive antigen-reactive CD8$^+$ and CD4$^+$ T cells, as well as production of the cytotoxic molecules granzyme B and perforin by antigen-reactive cytotoxic CD8$^+$ and CD4$^+$ T cells. Suitable preferred adjuvants which support a Th1 response are known in the art and are for example described in Tacken and Figdor, and in Speiser and Romero. (Tacken P. J., Figdor C. G.; Targeted antigen delivery and activation of dendritic cells in vivo: Steps towards cost effective vaccines. Semin. Immunol. (2011), doi:10.1016/j.smim.2011.01.001; Speiser D. E. and Romero P., Seminars in Immunology 22 (2010) 144-154).

The dendritic cell (DC) is capable of sensing through a large set of "danger signal" recognition receptors (e.g. toll-like receptors, NOD-like receptors), whether the antigen is of dangerous nature or whether it is harmless. The patterns recognized by the "danger signal" recognition receptors (also designated "pattern recognition receptors") are usually molecular structures that are unique to microorganisms. These can be cell wall components (e.g. lipopolysaccharide, peptidoglycan) or nucleic acid modifications (e.g. unmethylated CpG motifs) in case of microbes, or structural features and modifications that are unique to viral DNA or viral RNA (e.g. double-stranded RNA). Also cells dying from apoptosis in the body release molecules which are capable of triggering "danger signal" recognition receptors (e.g. High Mobility Group Protein B1, heat-shock proteins). Such danger signals are preferred Th1 adjuvants of the present invention.

For Example, adjuvant Poly I:C was successfully used in the Examples as Th1 adjuvant.

Therefore, in a further preferred embodiment of the medicament for use or method of the invention, the adjuvant which supports a Th-1-mediated response is selected from the group consisting of RIG-I-agonists, synthetic or recombinant TLR ligands, in particular TLR8 agonists, such as resiquimod (R848), or TLR3 agonists, such as poly ICLC and polyinosinic:polycytidylic acid (poly I:C), Montanides, like ISA51, ISA720, saponins like Quil-A, ISCOM, QS-21, AS02 and AS01, polyinosinic:polycytidylic acid (poly I:C), a lipopolysaccharide (LPS), and a CpG oligodeoxynucleotide, more preferably the adjuvant which supports a Th-1-mediated response is selected from an RIG-I-agonist, a TLR8 agonist, such as resiquimod (R848), and a TLR3 agonist, such as poly ICLC and polyinosinic:polycytidylic acid (poly I:C).

Poly-ICLC consists of poly-IC stabilized with poly-L-lysine and carboxymethylcellulose and is potent in supporting a Th1 response.

R848 is a selective ligand for TLR7 in mice and for TLR7 and TLR8 in humans and activates the NLR pyrin domain containing 3 (NLRP3) inflammasome.

For Poly-ICLC and R848, it is referred to Tacken and Figdor (supra) and references cited therein.

Montanides like ISA51 and ISA720 are water-in-oil emulsions containing squalene and mannide-monooleate as an emulsifier, as disclosed in Speiser and Romero and references cited therein.

Saponins like Quil-A, ISCOM, QS-21, AS02 and AS01 are triterpene glycosides isolated from plants, as disclosed in Speiser and Romero and references cited therein.

The administration of the adjuvant which supports a Th-1-mediated response and the administration of the peptide-loaded major histocompatibility complex class I (MHC-I) presenting cell can be separated both spatially and temporally.

In a further preferred embodiment of the medicament for use or method of the invention, the adjuvant which supports a Th-1-mediated response is administered before, simultaneously with or after the administration of the peptide-loaded major histocompatibility complex class I (MHC-I) presenting cell, preferably the adjuvant which supports a Th-1-mediated response is administered within a time frame of 1 day before and 3 days after the administration of the peptide-loaded major histocompatibility complex class I (MHC-I) presenting cell, more preferably the adjuvant which supports a Th-1-mediated response is administered (a) at the same day or (b) within a time frame of 1 day to 3 days after the administration of the peptide-loaded major histocompatibility complex class I (MHC-I) presenting cell, in particular within 1 day after the administration of the peptide-loaded major histocompatibility complex class I (MHC-I) presenting cell.

In a preferred embodiment, the adjuvant which supports a Th-1-mediated response is administered at the same day as the administration of the peptide-loaded major histocompatibility complex class I (MHC-I) presenting cell (see Example 8).

In a further preferred embodiment of the medicament for use or method of the invention, the adjuvant which supports a Th-1-mediated response is administered with the peptide-loaded major histocompatibility complex class I (MHC-I) presenting cell as a single pharmaceutical composition, or is administered spatially separated from the peptide-loaded major histocompatibility complex class I (MHC-I) presenting cell.

For example, the adjuvant which supports a Th-1-mediated response is administered with the peptide-loaded major histocompatibility complex class I (MHC-I) presenting cell as a single pharmaceutical composition, such as a suspension of the cells in aqueous solution, which optionally contains pharmaceutically acceptable excipients. In Example 8, a solution containing ADAS cells and poly I:C were administered i.v.

For activation of T cells against a given antigen, a further adjuvant which supports a Th-1-mediated response is used or optionally used, as described above.

Such further adjuvant which supports a Th-1-mediated response may be the same or a different adjuvant as the adjuvant used in step i) of medicament for use or method of the invention.

Therefore, in a further preferred embodiment of the medicament for use or method of the invention, the further adjuvant which supports a Th-1-mediated response is selected from the group consisting of RIG-I-agonists, synthetic or recombinant TLR ligands, in particular TLR8 agonists, such as resiquimod (R848), or TLR3 agonists, such as poly ICLC and polyinosinic:polycytidylic acid (poly I:C), Montanides, like ISA51, ISA720, saponins like Quil-A, ISCOM, QS-21, AS02 and AS01, polyinosinic:polycytidylic acid (poly I:C), a lipopolysaccharide (LPS), and a CpG oligodeoxynucleotide, preferably the adjuvant which supports a Th-1-mediated response is selected from an RIG-I-agonist, a TLR8 agonist, such as resiquimod (R848), and a TLR3 agonist, such as poly ICLC and polyinosinic:polycytidylic acid (poly I:C).

As shown in Example 8, the administration of the further adjuvant which supports a Th-1-mediated response and the administration of the delivery system can surprisingly be separated both spatially and temporally. Surprisingly, the best results were achieved when the adjuvant Poly I:C was applied one day after the administration of the delivery system.

For example, the further adjuvant which supports a Th-1-mediated response is administered with the delivery system as a single pharmaceutical composition, such as an aqueous solution, which optionally contains pharmaceutically acceptable excipients. In Example 8, a solution containing MARX10-OVA and poly I:C were administered i.v.

Alternatively, further adjuvant which supports a Th-1-mediated response may be administered spatially separated from the delivery system. For example, a pharmaceutical composition, such as an aqueous solution, which optionally contains pharmaceutically acceptable excipients, comprising the delivery system may be administered and a further pharmaceutical composition, such as an aqueous solution, which optionally contains pharmaceutically acceptable excipients, comprising the further adjuvant which supports a Th-1-mediated response may be administered. Such compositions may be administered at the same time or at different time points, as described above.

In a further preferred embodiment of the medicament for use or method of the invention, the further adjuvant which supports a Th-1-mediated response is administered with the delivery system as a single pharmaceutical composition, or is administered spatially separated from the delivery system.

In a further preferred embodiment of the medicament for use or method of the invention, the further adjuvant which supports a Th-1-mediated response is administered before, simultaneously with or after the administration of the delivery system, preferably the further adjuvant which supports a Th-1-mediated response is administered within a time frame of 1 day before and 3 days after the administration of the delivery system, more preferably the further adjuvant which supports a Th-1-mediated response is administered (a) at the same day or (b) within a time frame of 1 day to 3 days after the administration of the delivery system.

In our experiments with ADAS, we also found that the change of the activation status of $CD8^+$ T cells brought about by ADAS also makes these $CD8^+$ T cells sensitive for the action of complexed IL-2 (IL-2cx), and thus further strongly amplifies the cytotoxic $CD8^+$ T cells and further increases their biological potency (see Example 4).

Therefore, we surprisingly observed a strong and unexpected synergistic effect in amplifying and extending the cellular cytotoxic response by the application of a combination of ADAS and complexed IL-2 (IL-2cx). In particular, it was surprisingly found in our experiments, that the combination of ADAS and complexed IL-2 lead to a further, about 100-fold amplification in the number of T cells activated against the OVA-antigen as compared to ADAS alone.

Therefore, the combination of ADAS according to the present invention with complexed IL-2 is particularly preferred.

According to the present invention, "complexed IL-2" or "IL-2cx" is understood as IL-2 protein which is non-covalently bound to a binding molecule, in particular antibody or antibody fragment which is blocking its binding to the high affinity IL-2 receptor chain (CD25). In a preferred embodiment, the antibody is humanized or human. In a preferred embodiment, IL-2 is human IL-2, more preferably human wt IL-2. IL-2 may be synthesized synthetically or recombinantly, using an adequate host, more preferably IL-2 is prepared recombinantly. In a preferred embodiment, binding of complexed IL-2 to CD25 is reduced by at least 35%, more preferably at least 50%, even more preferably at least 75%, most preferably at least 90% or 95%, such as 100%, as compared to binding of uncomplexed IL-2 to CD25.

Binding to CD25 may be determined as Kd value using surface plasmon resonance spectroscopy, which is known to a person skilled in the art. For its proper action on preactivated $CD8^+$ T cells, IL-2 must be complexed with an antibody blocking the binding of IL-2 to the high-affinity receptor chain CD25, which is mainly expressed on regulatory T cells ($T_{reg}$). Without such blocking, the IL-2 would mainly act on $T_{reg}$, which then would suppress the activation and differentiation of $CD8^+$ T cells to cytotoxic cells. We have indeed observed either no beneficial effect of non-complexed IL-2 or even a detrimental effect (not shown). Therefore, a complexed IL-2, or mutated IL-2 capable of binding to CD122, wherein binding to CD25 is reduced, in particular reduced by at least 35%, more preferably at least 50%, even more preferably at least 75%, most preferably at least 90% or 95%, such as 100%, as compared to binding of uncomplexed IL-2 to CD25, or wildtype (wt) IL-2 to CD25, respectively, will achieve the observed amplification of the ADAS response. Binding to the receptors may be determined as Kd value using surface plasmon resonance spectroscopy, which is known to persons skilled in the art.

Complexed or mutated IL-2 may still have certain shortcomings, such as a residual activity on $T_{reg}$ or a residual toxicity on the vasculature. Since IL-15 shares many biological functions with IL-2, we reasoned that it might be used in further amplifying ADAS instead of IL-2cx, in particular since it does not act on $T_{reg}$. It is known that IL-15 needs to be complexed with its receptor to exert biological activity. However, since IL-15 has only a low structural similarity to IL-2, is differently regulated, and has overall a different biological role in vivo (Ring et al. 2012), it was not clear whether complexed IL-15 (IL-15cx) would be able to further amplify the CD8$^+$ T cell response in ADAS-treated individuals.

It was surprisingly found that a synergistic effect was also observed in amplifying and extending the cellular cytotoxic response by the application of a combination of ADAS and complexed IL-15 (IL-15cx) (Example 9). The receptors for IL-2 and IL-15 share with the receptors of IL-4 and IL-7 the "common gamma-chain" and act on same cell types (NK cells, activated and memory CD8$^+$ T cells). Accordingly, a synergistic effect may be achieved by using complexed interleukin 4 (IL-4cx) or complexed interleukin 7 (IL-7cx).

According to the present invention, "complexed IL-15" or "IL-15cx" is understood as a complex comprising, preferably consisting of, IL-15 and the soluble form of its receptor IL-15R (sIL-15R), wherein sIL1-5R is optionally comprised in a fusion protein, such as a fusion protein of sIL-15R with an antibody or a fragment thereof, such as an Fc or an antibody or antibody fragment comprising an Fc. For example, sIL-15R-Fc was successfully used in Example 9. IL-15 is preferably bound non-covalently to the soluble form of its receptor IL-15R (sIL-15R) in the complex. sIL-15R is known to a skilled person and is described in the prior art. The use of such fusion protein of sIL-15R with an antibody or a fragment thereof, such as an Fc or an antibody or antibody fragment comprising an Fc, is preferred, as the fusion protein may allow for further activation of pre-activated CD8 T cells in vivo. IL-15 is preferably human IL-15. In a further preferred embodiment, IL-15R is human IL-15R. In a further preferred embodiment, IL-15 is preferably wt IL-15, more preferably human wt IL-15.

According to the present invention, "complexed IL-4" or "IL-4cx" is understood as a complex comprising, preferably consisting of, IL-4 and an antibody or a fragment thereof specifically binding to IL-4. IL-4 is preferably human IL-4. In a further preferred embodiment, IL-4 is preferably wt IL-4, more preferably human wt IL-4. The antibody or a fragment thereof specifically binding to IL-4 is preferably a monoclonal antibody, human antibody, humanized antibody or chimeric antibody or a fragment thereof, such as an scFv, a multimers of an scFv, such as a diabody, triabody or tetrabody, a Fab, a tandab, or a flexibody. IL-4 is preferably bound non-covalently to the antibody or a fragment thereof specifically binding to IL-4 in the complex.

According to the present invention, "complexed IL-7" or "IL-7cx" is understood as a complex comprising, preferably consisting of, IL-7 and an antibody or a fragment thereof specifically binding to IL-7. IL-7 is preferably human IL-7. In a further preferred embodiment, IL-7 is preferably wt IL-7, more preferably human wt IL-7. The antibody or a fragment thereof specifically binding to IL-7 is preferably a monoclonal antibody, human antibody, humanized antibody or chimeric antibody or a fragment thereof, such as an scFv, a multimers of an scFv, such as a diabody, triabody or tetrabody, a Fab, a tandab, or a flexibody. IL-7 is preferably bound non-covalently to the antibody or a fragment thereof specifically binding to IL-7 in the complex.

In a further preferred embodiment of the medicament for use or method of the invention, the method further comprises administering complexed interleukin 2 (IL-2cx), complexed interleukin 15 (IL-15cx), complexed interleukin 4 (IL-4cx), complexed interleukin 7 (IL-7cx), or a IL-2 mutein. In a more preferred embodiment, the administering of such agent is performed after administering to said patient said peptide-loaded major histocompatibility complex class I (MHC-I) presenting cell.

A strong synergistic effect was observed in the Examples when either complexed interleukin 2 (IL-2cx) or complexed interleukin 15 (IL-15cx) was further administered. Therefore, the further administration of complexed interleukin 2 (IL-2cx) or complexed interleukin 15 (IL-15cx) is particularly preferred.

A surprisingly strong and beneficial synergistic effect was observed when complexed IL-2 was used in the Examples. Therefore, in a most preferred embodiment of the present invention, the method further comprises administering complexed interleukin 2 (IL-2cx) to the patient.

An IL-2 mutein is understood as IL-2 protein, in particular human IL-2 protein, which is mutated as compared to the wt IL-2 protein, and which binds to CD122, but exhibits reduced binding to CD25 as compared to the wt IL-2 protein. In a preferred embodiment, binding to CD25 is reduced by at least 35%, more preferably by at least 50%, even more preferably by at least 75%, most preferably by at least 90% or 95%, such as by 100%, as compared to binding of wt IL-2 protein to CD25. Binding to CD25 may be determined as determining affinity, expressed as Kd value, in particular using surface plasmon resonance spectroscopy, which is known to persons skilled in the art. Moreover, binding to CD122 may be determined using surface plasmon resonance spectroscopy. In a preferred embodiment, binding of the IL-2 mutein to CD122 is at least 10%, preferably at least 35%, more preferably at least 50%, even more preferably at least 90% or 95%, such as 100% or more, of the binding of the wt IL-2 protein to CD122. A particularly preferred IL-2 mutein for use in the present invention is disclosed in Carmenate, Journal of Immunology 2013. In particular, a R38, F42, Y45, E62 mutein of wt IL-2, preferably R38A, F42A, Y45A, E62A mutein of wt IL-2 may be used, which mutein may further comprise a C125 mutation, such as a C125S mutation. Another particularly preferred IL-2 mutein which may be used according to the present invention is described in Klein et al. 2014.

In a more preferred embodiment of the medicament for use or method of the invention, the complexed interleukin 2 (IL-2cx), complexed interleukin 15 (IL-15cx), complexed interleukin 4 (IL-4cx), complexed interleukin 7 (IL-7cx), or IL-2 mutein is administered repeatedly, in particular 1, 2, 3, 4, 5, 6, 7, 8, 9, 10, 11, 12, 13 or 14 times, even more preferably wherein the complexed interleukin 2 (IL-2cx), complexed interleukin 15 (IL-15cx), complexed interleukin 4 (IL-4cx), complexed interleukin 7 (IL-7cx), or IL-2 mutein is administered every 1 or 2 days, and/or is administered repeatedly during 5 days to 1 month, even more preferably during 1 to 2 weeks.

As described above, complexed interleukin 2 (IL-2cx), complexed interleukin 15 (IL-15cx), complexed interleukin 4 (IL-4cx), complexed interleukin 7 (IL-7cx), or IL-2 mutein, preferably complexed interleukin 2 (IL-2cx) or complexed interleukin 15 (IL-15cx), is administered repeatedly after the T cells were activated against an antigen in a time frame of from 0 h to 14 days after the T cells were activated against an antigen. It is further possible, that one or more further administration(s) of complexed IL-2 interleukin 2 (IL-2cx), complexed interleukin 15 (IL-15cx), complexed interleukin 4 (IL-4cx), complexed interleukin 7 (IL-7cx), or IL-2 mutein take(s) place after 14 days after the T cells were activated against an antigen; however, at least one administration is in a time frame of from 0 h to 14 days.

In a further preferred embodiment, complexed interleukin 2 (IL-2cx), complexed interleukin 15 (IL-15cx), complexed interleukin 4 (IL-4cx), complexed interleukin 7 (IL-7cx), or IL-2 mutein is preferably administered in a time frame of from 48 h to 14 days, even more preferably of from 3 days to 12 days, 5 days to 12 days or 5 days to 9 days, or 3 days to 8 days, for example 3 days, 4 days, 5 days, 6 days, 7 days, 8 days, 9 days, 10 days, 11 days, 12 days, 13 days or 14 days after the T cells were activated against an antigen.

In a yet further preferred embodiment, in case of the combination, complexed interleukin 2 (IL-2cx), complexed interleukin 15 (IL-15cx), complexed interleukin 4 (IL-4cx), complexed interleukin 7 (IL-7cx), or IL-2 mutein is preferably administered repeatedly in a time frame of from 48 h to 9, 10, 11, 12, 13 or 14 days, even more preferably of from 3 days to 8 or 9 days, for example 3 days, 4 days, 5 days, 6 days, 7 days, 8 days or 9 days after the T cells were activated against an antigen. Thus, complexed interleukin 2 (IL-2cx), complexed interleukin 15 (IL-15cx), complexed interleukin 4 (IL-4cx), complexed interleukin 7 (IL-7cx), or IL-2 mutein is preferably administered 1, 2, 3, 4, 5, 6, 7, 8, 9 or 10 times in a time frame of from 48 h to 14 days or 48 h to 9 days, even more preferably of from 3 days to 8 or 9 days, for example 3 days, 4 days, 5 days, 6 days, 7 days, 8 days or 9 days after the T cells were activated against an antigen. For example, complexed interleukin 2 (IL-2cx) or complexed interleukin 15 (IL-15cx) may be administered daily or every two days. For example, complexed interleukin 2 (IL-2cx) or complexed interleukin 15 (IL-15cx) may be administered 48 h, 3 days, 4 days, 5 days, 6 days, 7 days and 8 days after the T cells were activated against an antigen. In another example, complexed interleukin 2 (IL-2cx) or complexed interleukin 15 (IL-15cx) may be administered 48 h, 4 days, 6 days, and 8 days after the T cells were activated against an antigen.

It is further possible, that one or more further administration(s) of complexed IL-2, complexed interleukin 15 (IL-15cx), complexed interleukin 4 (IL-4cx), complexed interleukin 7 (IL-7cx), or IL-2 mutein, preferably complexed IL-2 or complexed interleukin 15 (IL-15cx), is performed after the indicated time frame of, e.g. 14 days, preferably 9 or 8 days, after the administration of step i); however, at least one administration is preferably within the indicated time frame.

The administration of complexed IL-2, complexed interleukin 15 (IL-15cx), complexed interleukin 4 (IL-4cx), complexed interleukin 7 (IL-7cx), or IL-2 mutein may be performed by various routes of administrations and using a suitable formulation. For example, an aqueous solution of complexed IL-2, complexed interleukin 15 (IL-15cx), complexed interleukin 4 (IL-4cx), complexed interleukin 7 (IL-7cx), or IL-2 mutein, optionally further comprising pharmaceutically acceptable excipients, such as a pharmaceutically acceptable buffering compound, may be used.

In another more preferred embodiment of the medicament for use or method of the invention, the complexed interleukin 2 (IL-2cx), complexed interleukin 15 (IL-15cx), complexed interleukin 4 (IL-4cx), complexed interleukin 7 (IL-7cx), or IL-2 mutein is administered intravenously, subcutaneously, intraperitoneally, intradermally, or intrathecally, or is administered into the tumor, preferably by injection. Complexed interleukin 2 (IL-2cx), complexed interleukin 15 (IL-15cx), complexed interleukin 4 (IL-4cx), complexed interleukin 7 (IL-7cx), or IL-2 mutein is preferably administered as a solution and/or at a dosage in the range of from 1 µg/kg body weight to 200 µg/kg body weight, more preferably of from 1 µg/kg body weight to 50 µg/kg body weight, even more preferably of from 1 µg/kg body weight to 20 µg/kg body weight.

In a yet further embodiment, the present invention relates to a medicament for use in a method of extending and/or amplifying a cellular cytotoxic immune response against an antigen-comprising protein, the method comprising the step of:
i) administering to a patient having T cells activated against an antigen a peptide-loaded major histocompatibility complex class I (MHC-I) presenting cell by intravenous administration and an adjuvant which supports a Th-1-mediated response, wherein the peptide is derived from the antigen-comprising protein, thereby re-activating the activated T cell, and wherein the peptide-loaded major histocompatibility complex class I (MHC-I) presenting cell is not a dendritic cell.

In a further embodiment, the present invention relates to a method of extending and/or amplifying a cellular cytotoxic immune response against an antigen-comprising protein, the method comprising the step of:
i) administering to a patient having T cells activated against an antigen a peptide-loaded major histocompatibility complex class I (MHC-I) presenting cell by systemic administration and an adjuvant which supports a Th-1-mediated response, wherein the peptide is derived from the antigen-comprising protein, thereby re-activating the activated T cell, and wherein the peptide-loaded major histocompatibility complex class I (MHC-I) presenting cell is not a dendritic cell.

As described above, systemic administration is surprisingly effective in extending and/or amplifying the cellular cytotoxic immune response. Preferred routes for systemic administration are intravenous, intraperitoneal, or intrathecal administration, wherein intravenous administration is particularly preferred.

In a yet further preferred embodiment, between $1 \times 10^6$ and $4 \times 10^8$, more preferably between $1 \times 10^7$ and $4 \times 10^8$ peptide-loaded major histocompatibility complex class I (MHC-I) presenting cells are administered to said patient. Thereby, a high amount of cells can be administered.

In a preferred embodiment of the medicament for use or method of the invention, the peptide-loaded major histocompatibility complex class I (MHC-I) presenting cell is a blood cell, especially a peripheral blood mononucleated cell (PBMC).

In a further preferred embodiment of the medicament for use or method of the invention, the peptide-loaded major histocompatibility complex class I (MHC-I) presenting cell of step i) is administered in a time frame of from 0 h to 14 days after the T cells were activated against an antigen.

For such medicament for use and method of the invention, respectively, the same preferred embodiments apply as for the medicaments for use and method of the invention described herein above and below.

In a more preferred embodiment, the present invention relates to a medicament for use in a method of amplifying a cellular cytotoxic immune response against an antigen-comprising protein, and to a method of amplifying a cellular cytotoxic immune response against an antigen-comprising protein.

In a yet further preferred embodiment, the present invention relates to a medicament for use in a method of extending a cellular cytotoxic immune response against an antigen-comprising protein, and to a method of extending a cellular cytotoxic immune response against an antigen-comprising protein.

In a further embodiment, the present invention relates to a method of extending and amplifying a cellular cytotoxic immune response against an antigen-comprising protein, and to a method of extending and amplifying a cellular cytotoxic immune response against an antigen-comprising protein.

In a yet further embodiment, the present invention relates to a kit-of-parts comprising a peptide-loaded major histocompatibility complex class I (MHC-I) presenting cell as defined above, and
(i) at least one agent selected from complexed interleukin 2 (IL-2cx), complexed interleukin 15 (IL-15cx), complexed interleukin 4 (IL-4cx), complexed interleukin 7 (IL-7cx), and a IL-2 mutein, and/or
(ii) a delivery system a defined above,
and optionally further comprising at least one adjuvant which supports a Th-1-mediated response.

For the kit-of-parts of the invention, the same preferred embodiments apply as for the medicaments for use and method of the invention described herein.

The parts of the kits are preferably in separate containers.

In particular, the peptide-loaded major histocompatibility complex class I (MHC-I) presenting cell may be comprised in a suspension, such as cells suspended in an aqueous solution and optionally further containing pharmaceutically acceptable excipients. A container, such as a vial, may contain the pharmaceutical composition comprising the peptide-loaded major histocompatibility complex class I (MHC-I) presenting cell. In a preferred embodiment, the pharmaceutical composition is suitable for systemic administration, in particular for intravenous administration. The pharmaceutical composition may further comprise at least one adjuvant which supports a Th-1-mediated response, or may not comprise at least one adjuvant which supports a Th-1-mediated response.

Further, the at least one agent selected from complexed interleukin 2 (IL-2cx), complexed interleukin 15 (IL-15cx), complexed interleukin 4 (IL-4cx), complexed interleukin 7 (IL-7cx), and an IL-2 mutein may be comprised in a solution, such as an aqueous solution, or dried or freeze-dried, and optionally further containing pharmaceutically acceptable excipients. A container, such as a vial, may contain the pharmaceutical composition comprising complexed interleukin 2 (IL-2cx), complexed interleukin 15 (IL-15cx), complexed interleukin 4 (IL-4cx), complexed interleukin 7 (IL-7cx), and an IL-2 mutein.

Further, the delivery system may be comprised in a solution, such as an aqueous solution, or suspension, or dried or freeze-dried, and optionally further containing pharmaceutically acceptable excipients. A container, such as a vial, may contain the pharmaceutical composition comprising the delivery system. The pharmaceutical composition may further comprise at least one adjuvant which supports a Th-1-mediated response, or may not comprise at least one adjuvant which supports a Th-1-mediated response.

Further, the at least one adjuvant which supports a Th-1-mediated response may be comprised in a solution, such as an aqueous solution, or dried or freeze-dried, and optionally further containing pharmaceutically acceptable excipients. Therefore, the kit-of-parts may further contain a pharmaceutical composition comprising at least one adjuvant which supports a Th-1-mediated response. In one embodiment, the pharmaceutical composition does not contain a delivery system and/or does not contain a peptide-loaded major histocompatibility complex class I (MHC-I) presenting cell of the invention.

In a yet further embodiment, the present invention relates to a medicament for use in a method of inducing a cellular cytotoxic immune response, the method comprising the steps of:
(A) (i)
(1) administering to said patient a delivery system comprising
(a) a molecule binding to a receptor on the surface of an antigen-presenting cell,
(b) an antigen-comprising protein bound to molecule of (a) and wherein upon binding of the molecule of (a) to the receptor, the protein of (b) is internalized and processed in the antigen-presenting cell and the antigen comprised in the protein is presented on the surface of the antigen-presenting cell, thereby activating a T cell in the patient, and (2) administering a further adjuvant which supports a Th-1-mediated response,
or
(ii)
(1) activating one or more T cells obtained from said patient in vitro with an antigen-comprising protein or a fragment thereof comprising the antigen,
(2) re-transferring one or more T cells obtained in step (1) to said patient, and
(3) optionally administering a further adjuvant which supports a Th-1-mediated response,
or
(iii)
(1) administering to said patient
an antigen-comprising protein or a fragment thereof comprising the antigen,
or
a nucleic acid comprising a nucleic acid sequence encoding an antigen-comprising protein or a fragment thereof comprising the antigen, which is capable of expressing the antigen-comprising protein or a fragment thereof comprising the antigen in said patient,
thereby activating at least one T cell,
and
(2) administering a further adjuvant which supports a Th-1-mediated response, and
(B) administering to the patient at least one reactivator selected from:
(a) a peptide-loaded major histocompatibility complex class I (MHC-I) presenting cell and an adjuvant which supports a Th-1-mediated response, wherein the peptide is derived from the antigen-comprising protein, thereby re-activating the activated T cell, and
(b) complexed interleukin 2 (IL-2cx), complexed interleukin 15 (IL-15cx), complexed interleukin 4 (IL-4cx), complexed interleukin 7 (IL-7cx), or a IL-2 mutein, wherein the reactivator is administered in a time frame of from 0 h to 14 days after the T cells were activated against an antigen, preferably wherein the reactivator is administered only once in a time frame of from 0 h to 14 days after the T cells were activated against an antigen.

In a yet further embodiment, the present invention relates to a method of inducing a cellular cytotoxic immune response, the method comprising the steps of:

(A) (i)
- (1) administering to said patient a delivery system comprising
  - (a) a molecule binding to a receptor on the surface of an antigen-presenting cell,
  - (b) an antigen-comprising protein bound to molecule of (a) and
  - wherein upon binding of the molecule of (a) to the receptor, the protein of (b) is internalized and processed in the antigen-presenting cell and the antigen comprised in the protein is presented on the surface of the antigen-presenting cell, thereby activating a T cell in the patient, and
- (2) administering a further adjuvant which supports a Th-1-mediated response, or (ii)
- (1) activating one or more T cells obtained from said patient in vitro with an antigen-comprising protein or a fragment thereof comprising the antigen,
- (2) re-transferring one or more T cells obtained in step (1) to said patient, and
- (3) optionally administering a further adjuvant which supports a Th-1-mediated response, or (iii)
- (1) administering to said patient
  - an antigen-comprising protein or a fragment thereof comprising the antigen,
  or
  - a nucleic acid comprising a nucleic acid sequence encoding an antigen-comprising protein or a fragment thereof comprising the antigen, which is capable of expressing the antigen-comprising protein or a fragment thereof comprising the antigen in said patient,
  - thereby activating at least one T cell,
  and
- (2) administering a further adjuvant which supports a Th-1-mediated response, and (B) administering to the patient at least one reactivator selected from:
- (a) a peptide-loaded major histocompatibility complex class I (MHC-I) presenting cell and an adjuvant which supports a Th-1-mediated response, wherein the peptide is derived from the antigen-comprising protein, thereby re-activating the activated T cell, and
- (b) complexed interleukin 2 (IL-2cx), complexed interleukin 15 (IL-15cx), complexed interleukin 4 (IL-4cx), complexed interleukin 7 (IL-7cx), or a IL-2 mutein, wherein the reactivator is administered in a time frame of from 0 h to 14 days after the T cells were activated against an antigen, preferably wherein the reactivator is administered only once in a time frame of from 0 h to 14 days after the T cells were activated against an antigen.

In a further preferred embodiment of the medicament for use or method of the invention, the reactivator of (B)(a) is administered only once to the patient.

For the medicament for use in a method of inducing a cellular cytotoxic immune response and the method of inducing a cellular cytotoxic immune response, the same preferred embodiments apply as for the method of extending a cellular cytotoxic immune response and the method of extending a cellular cytotoxic immune response of the invention, described herein.

In another preferred embodiment of the medicament for use or method of the invention, the reactivator, preferably the reactivator of the reactivator of (B)(a), is administered in a time frame from 72 h to 12 days, preferably from 5 h to 12 days, more preferably from 5 days to 9 days after the T cells were activated against an antigen.

In a further preferred embodiment of the medicament for use or method of the invention, the delivery system of (A)(i) above is administered. In this preferred embodiment, the "priming" step (A) is effected by targeted approach which is in particular effective as shown in the examples. In such embodiment, the delivery system comprises (a) a molecule binding to a receptor on the surface of an antigen-presenting cell, and (b) an antigen-comprising protein bound to molecule of (a) and wherein upon binding of the molecule of (a) to the receptor, the protein of (b) is internalized and processed in the antigen-presenting cell and the antigen comprised in the protein is presented on the surface of the antigen-presenting cell, thereby activating a T cell in the patient. In such embodiment, a further adjuvant which supports a Th-1-mediated response is administered to the patient.

In a more preferred embodiment, the antigen-presenting cell is a selected from a dendritic cell, a macrophage and a B cell.

In an even more preferred embodiment the antigen-presenting cell is a dendritic cell.

In a further preferred embodiment of the medicament for use or method of the invention, the receptor on the surface of a dendritic cell is a receptor on the surface of cross-presenting dendritic cells.

In a further preferred embodiment of the medicament for use or method of the invention, the receptor on the surface of a dendritic cell is chemokine (C motif) receptor 1 (XCR1), nectin-like molecule 2, a c-type lectin (CLEC) such as CLEC9A, preferably the receptor on the surface of a dendritic cell is XCR1.

In a further preferred embodiment of the medicament for use or method of the invention, the molecule binding to a receptor on the surface of an antigen-presenting cell of (a) of the delivery system is a ligand to the receptor or an antibody or antibody fragment against the receptor, particularly wherein the receptor is chemokine (C motif) receptor 1 (XCR1) and wherein the molecule of a) is anti-XCR1 antibody or fragment thereof or chemokine (C motif) ligand 1 (XCL1) or a functionally active variant thereof, particularly comprising or consisting of the sequence of any of SEQ ID NOs: 7 to 10, preferably, of SEQ ID NOs: 8 to 10, more preferably of SEQ ID NOs: 9 or 10, especially of SEQ ID NO: 10.

In a further preferred embodiment of the medicament for use or method of the invention, the antigen of antigen-comprising protein is an immunogen, a pathogen-derived antigen, or a tumor antigen. In a further preferred embodiment of the medicament for use or method of the invention, the T cell is a CD8$^+$ T cell or a CD4$^+$ T cell, preferably a CD8$^+$ T cell.

The preferred embodiments applicable to the medicaments for use in a method of extending a cellular cytotoxic immune response and the corresponding methods of the invention also apply to the medicaments for use in a method of inducing a cellular cytotoxic immune response and the corresponding methods of the invention.

It has been found in WO 2009/065561, that cells playing a major role in the induction of the Th1 response can be selectively targeted. It was found that chemokine (C motif) receptor 1 (XCR1) is present on the surface of professional antigen-presenting cell, particularly dendritic cells (DC), and can be used to selectively deliver substance into these cells. Targeted delivery of a substance to XCR1-bearing DC allows induction of a potent Th1 immune reaction in mammals/humans. Current vaccines mainly address the Th2 antigen presentation pathway and mainly lead to the generation of Th2-type (neutralizing) antibodies and immune reactions. In particular, through targeting to XCR1-bearing DC, a Th1-type humoral and cellular (cytotoxic) immune reaction can be elicited to a given immunogen. It can be anticipated that NK cells, CD8$^+$ T cells, and Th1CD4$^+$ T cells participate in this reaction, but other CD4$^+$ T cells may also contribute to this type of reaction. An adjuvant, either alone or in combination with an immunogen or any pharmaceutical compound, can be selectively targeted to XCR1-bearing antigen-presenting cells (APC).

In the periphery, the immune system has to discriminate between harmless foreign or self-antigens on the one hand and dangerous (viral, bacterial, fungal, parasitic, toxin-like) antigens on the other hand. The antigen is taken up by the DC and broken down to peptides ("processed"). The resultant peptides are "presented" to T lymphocytes (T cells) in the context of the MHC class I or MHC class II. The CD4$^+$ subset of T cells recognizes the antigen in the context of MHC class II, the CD8$^+$ subset of T cells recognizes the antigen in the context of MHC class I. Concomitant with the uptake of antigen, the DC is capable of sensing through a large set of "danger signal" recognition receptors (e.g. toll-like receptors, NOD-like receptors), whether the antigen is of dangerous nature or whether it is harmless. The patterns recognized by the "danger signal" recognition receptors (also designated "pattern recognition receptors") are usually molecular structures that are unique to microorganisms. These can be cell wall components (e.g. lipopolysaccharide, peptidoglycan) or nucleic acid modifications (e.g. unmethylated CpG motifs) in case of microbes, or structural features and modifications that are unique to viral DNA or viral RNA (e.g. double-stranded RNA). Also cells dying from apoptosis in the body release molecules which are capable of triggering "danger signal" recognition receptors (e.g. High Mobility Group Protein B1, heat-shock proteins).

In the case of a dangerous antigen, the DC activates a specific response program ("maturation"). The antigen is presented to CD4$^+$ and CD8$^+$ T cells, which simultaneously receive from the DC additional signals indicating the dangerous nature of the antigen. As a result, both T cell subsets become activated, expand extensively with a prolonged life span and develop to "effector T cells". These can be CD4$^+$ T cells providing "help" to other DC or B cells or other cells of the immune system, or can be even CD4+ cytotoxic cells. Within the CD8$^+$ T cell subset, again T helper cells develop, but a large proportion of CD8$^+$ T cells become effector cells capable of eliminating the invading pathogen through secretion of IFN-γ and other soluble factors or through killing of infected body cells. As a result of the T cell help to B cells, antigen-specific B cells differentiate to plasma cells which secrete antibodies directed to the antigen (pathogen). These antibodies help to fight the pathogen through a number of mechanisms (e.g. neutralization, improved antigen uptake, opsonization, complement fixation).

A certain number of effector CD4$^+$ and CD8$^+$ T cells survive the acute phase of an immune response to a pathogen and become long-lived "memory T cells". Memory T cells and long-lived plasma cells orchestrate upon re-exposure to the same pathogen (antigen) a very fast immune response allowing the immune system to eliminate the pathogen (antigen) very effectively. This enhanced capability of the T-cell and B cell immune response upon re-exposure to the same pathogen is termed "immunity" and the antigens which induce immunity are "immunogenic".

In summary, the T cell compartment of the immune system contains CD4$^+$ T cells and CD8$^+$ T cells. In the naïve organism, only a few hundred CD4$^+$ or CD8$^+$ T cells recognize a given antigen. As long as they have not encountered antigen, T cells are in a naïve state and cannot exert effector functions. Naïve CD4$^+$ and CD8 T cells can only be activated by APC by soluble protein or polypeptide antigen, which is taken up by the APC, processed, and "presented" on the cell surface in the context of MHC. The source of primary antigen exposure can be a soluble protein or polypeptide or any type of vaccine, such as attenuated infectious agents, viral or bacterial vectors coding for a desired antigenic protein or peptide, or DNA or RNA expression vectors coding for an antigenic protein or peptide. As a result of primary exposure to antigen in the context of danger signals there will exist within days a population of "primed" CD4$^+$ and CD8$^+$ T cells.

When protein antigen is targeted into an APC, it will be degraded ("processed") to peptides and these peptides will be presented on the surface of the APC in the context of MHC-II (classical presentation) and MHC-I ("cross-presentation"). Naïve CD4$^+$ T cells recognize their peptide-antigen in the context of MHC-II, naïve CD8 T cells in the context of MHC-I. They become activated, proliferate, and acquire effector functions. If the peptides are presented by the DC in the context of a "danger signal", the expanded CD8$^+$ T cells will differentiate into cytotoxic T cells. Only professional APC are capable of inducing this cytotoxic function in naïve CD8$^+$ T cells ("priming", "primary immunization"). Once the CD8$^+$ T cells have acquired their cytotoxic potential, they will be able to kill cells in the body which express the same peptides in the context of MHC-I. Thus they will kill cells infected by a given infectious agent or tumor cells.

Antigens which are taken up by cells capable of antigen presentation are not only presented in the context of MHC-I ("cross-presentation"), but also in the context of MHC-II ("classical presentation"). Therefore, any antigen delivery into antigen-presenting cells, together with a danger signal, will not only activate CD8$^+$ T cells, but also CD4$^+$ T cells. The CD4$^+$ T cells will differentiate into Th1 T cells secreting TNF-α and IFN-γ, and some will also develop into cytotoxic T cells.

Primary CD8$^+$ T cell activation can be achieved by providing a soluble antigen, or by direct or indirect targeting of antigen(s) into APC (B cells, macrophages, DC), and in particular into XCR1$^+$ DC of a naïve host. Indirect targeting is achieved by providing the antigen in cells which are not APC, but which can hand over the antigen to APC, in particular to XCR1$^+$ DC in vivo. When the antigen is applied together with a "danger signal" (e.g. LPS, Poly I:C, CpG, etc.), this will induce primary CD8$^+$ T cell cytotoxic immunity.

Similar early T cell activation can be expected by antigenic re-challenge (in the presence of danger signals) of a host, which has been primed with antigen before and whose antigen-specific CD8$^+$ T cells and CD4 T cells are in a non-activated memory state.

Similar T cell activation can be expected in hosts which harbor low grade chronic infections which cannot be cleared by the host (e.g. CMV, HCV, HIV). Antigen can be targeted into APC. This targeting can be mediated by monoclonal antibodies (mAb) or antibody fragments binding to surface structures on APC, or by any ligands binding to receptors on the surface of APC. These ligands can be sugar moieties, chemokines, soluble protein ligands, or any other structures allowing internalization of the antigen into the APC. Antigen taken up by any DC is presented both in the context of MHC-I and MHC-II. Direct or indirect targeting of antigen into dendritic cells (DC) substantially improves cross-presentation over other modes of antigen application. Best cross-presentation and thus priming of $CD8^+$ T cells can be achieved by targeting of antigen into $XCR1^+$ DC (Bachem et al. 2010, J Exp Med 207, 1273-1281, Bachem et al., 2012, Front Immunol 3, 214; Caminschi et al. 2013, Radford et al. 2013, Kreutz et al. 2013).

After an efficient priming of $CD8^+$ T cells in the context of a danger signal (which is also a first adjuvant), these cytotoxic T cells will represent approximately 1% to 5% of the $CD8^+$ T cell repertoire and exhibit significant cytotoxic potential. For example, the achieved cytotoxicity may protect the host against a pathogen, from which the antigen was derived, and this level of protection can also be effective for newly developing cancerous tissue (FIG. 2B).

However, when attempting to establish long-term immunity against a given antigen or to provide high levels of cytotoxic protection against imminent infections, or to provide high levels of cytotoxicity against already established tumors, the cytotoxic potential induced by an initial priming of naïve $CD8^+$ T cells or be re-activation of $CD8^+$ T cells may not suffice. Under these circumstances a further amplification of the activated antigen-specific $CD8^+$ T cells is necessary.

After recognizing antigen expressed in the context of MHC-I, $CD8^+$ T cells become activated, de novo express or strongly upregulate a variety of cell surface molecules, such as CD69, 4-1BB, ICOS, CD25, CD40L, OX40, and proliferate for up to approximately 8 days in the mouse (the timeframe may be somewhat different in the human). Thereafter, the initially activated $CD8^+$ T cells gradually return over approximately 2-3 weeks into a resting "memory" state. At the same time, the expanded antigen-specific T cell population strongly contracts. A proportion of the $CD8^+$ T cells will survive this process of contraction and will become memory T cells (Cui et al., 2010, Immunol. Rev. 236, 151-166). Classical vaccination schemes can be divided into an initial priming step, followed by one or several "boostings". The principle of boosting is based on de novo activation of initially expanded B cells or T cells which have undergone a downmodulation of the initial activation or have already reverted into the resting state.

The further problem underlying the present invention is the provision of an improved medicament for use in a method for inducing a cellular cytotoxic immune response and/or in a method for extending a cellular cytotoxic immune response compared to prior art technologies.

The problem is solved by the present invention.

In a further embodiment, the present invention relates to a medicament for use in a method of inducing a cellular cytotoxic immune response, the method comprising the steps of:
 i) administering to a patient a delivery system comprising
  (a) a molecule binding to a receptor on the surface of a dendritic cell, (b) an antigen-comprising protein bound to molecule of (a) and (c) a first adjuvant,
  wherein upon binding of the molecule of (a) to the receptor, the protein of (b) is internalized and processed in the dendritic cell and the antigen comprised in the protein is presented on the surface of the dendritic cell, thereby activating a T cell in the patient; and
 ii) administering to the patient a re-activator selected from the group consisting of (d) complexed interleukin 2 (IL-2cx), (e) a peptide-loaded major histocompatibility complex class I (MHC-I) presenting cell and a second adjuvant, and (f) a combination of (d) and (e), wherein the peptide is derived from the antigen-comprising protein as defined in step i), thereby re-activating the T cell activated in step i),
 wherein the re-activator of step ii) is administered in a time frame of from 0 h to 14 days after the administration of the delivery system of step i).

In a preferred embodiment, the medicament is for use in a human.

The patient is preferably a mammalian patient, more preferably a human patient.

The patient may be suffering from an infection or tumor, or, in case of prophylactic treatment, is not suffering from an infection or tumor, but is to be protected from a respective infection or tumor disease.

In a further preferred embodiment, the receptor on the surface of a dendritic cell is a human receptor on the surface of a dendritic cell.

One possibility to provide strong T cell cytotoxicity within a short time would be to interfere with the down regulatory mechanism becoming effective within days of the initial activation or re-activation of $CD8^+$ T cells by antigen. To prevent this down modulation of the $CD8^+$ T cell response, we reasoned that we have to provide another stimulus involving the T cell receptor complex on CD8 T cells and/or appropriate growth factors within a short timeframe of the initial activation or re-activation. This concept runs against the current dogma which teaches that repeated activation of T cells via the T cell receptor within a short time will result in "activation-induced cell death" (Gorak-Stolinska et al., 2001, J Leukoc Biol 70, 756-766).

To test our concept, C57BL/6 mice were immunized ("primed") by targeting an antigen into $XCR1^+$ DC in the presence of a first adjuvant which supports a Th-1 response (poly I:C, LPS, CpG, or equivalent). As antigen for this primary immunization we used the model antigen ovalbumin (OVA), or a peptide sequence derived from ovalbumin (SIINFEKL (SEQ ID NO: 11)). This peptide sequence is known to be preferentially presented in the context of the MHC-I of C57BL/6 mice after processing of OVA by the targeted APC. For this initial immunization, the protein OVA or the peptide SIINFEKL (SEQ ID NO: 11) were recombinantly fused either to a monoclonal antibody (mAb) specific for XCR1 or to the chemokine ligand XCL1 binding to XCR1, as described earlier (WO 200/065561). At various time points (3-20 days) after this priming step, mice were re-exposed to antigen. We did not inject protein or peptides into the host, since we anticipated that either procedure would lead to the presentation of antigenic peptides in the context of the MHC-I on host cells, which then would be killed by the already activated antigen-specific $CD8^+$ T cells (compare FIG. 1A), a highly undesired effect. Instead, syngeneic splenic cells were isolated from C57BL/6 mice, incubated with the peptide SIINFEKL (SEQ ID NO: 11) in vitro ("loading" of MHC-I), washed, and injected i.v. into mice which have been primed before.

Unexpectedly, and contrary to current knowledge, we could achieve with this regime an amplification of the number of antigen-specific CD8$^+$ T cells, when the CD8$^+$ T cells were re-exposed to antigen within a narrow timeframe. No amplification was observed, when re-exposure was very early, on day 3, and very limited amplification was observed when re-exposure to antigen was done following day 9 of initial CD8$^+$ T cell activation (FIG. 3). Injection of SIINFEKL-loaded syngeneic splenic cells into primed animals alone did not expand the primed CD8$^+$ T cell population, only when a second adjuvant (poly I:C, LPS, CpG, or equivalent) was co-applied to provide a "danger" signal, the desired effect was achieved. When the injection of peptide-loaded splenocytes was performed at an optimal time point, the antigen-responsive CD8$^+$ T cell population expanded approximately 10-fold, from 0.2×10$^6$ after priming without amplification, to 2×10$^6$ cells with amplification (FIG. 4). These expanded CD8$^+$ T cells expressed high levels of effector molecules such as Granzyme B, perforin, TNF-α and IFN-γ, molecules involved in the CD8$^+$ T cell defense of infectious agents or in the eradication of tumors. In the human, the optimal timeframe for the amplification of the initial T cell activation may differ from the optimal timeframe in the mouse (approximately day 5-8 after initial CD8$^+$ T cell activation).

When comparing various amplification time points, it became apparent that a re-exposure with antigen 5-8 days after the initial priming gives the highest degree of CD8$^+$ T cell expansion and the highest expression of cytotoxic effector molecules (TNF-α, IFN-γ, granzyme B, perforin) in CD8$^+$ T cells. Day 5-8 is an early time point following the recognition of antigen by resting CD8$^+$ T cells and thus a time point at which the T cells are still strongly activated. Therefore, this amplification does not represent a classical boost system. Instead, this type of amplification provides signals allowing T cells to continue their initial activation and expansion phase instead of entering the usual phase of downregulation and contraction. Because of this particular effect, we have termed this amplification, when applied together with an adjuvant, as "Antigen-Dependent Amplification System" (ADAS). Therefore, according to the present invention, "Antigen-Dependent Amplification System" or "ADAS" is understood as the second step ii) of the present invention relating to administering to the patient a re-activator, wherein the reactivator is a peptide-loaded major histocompatibility complex class I (MHC-I) presenting cell and a second adjuvant, and wherein the peptide is derived from the antigen-comprising protein as defined in step i) of the present invention, thereby re-activating the T cell activated in step i). Optionally, the reactivator in ADAS further comprises complexed interleukin 2 (IL-2cx).

In order to examine the cellular requirements for the effectiveness of ADAS, various lymphocytic populations (splenocytes, B cells, T cells, and DC) were for comparison loaded with SIINFEKL (SEQ ID NO: 11) in vitro and injected within the optimal timeframe in mice (day 5) together with a second adjuvant (poly I:C, LPS, CpG, or equivalent). This experiment determined that all of these lymphocytic populations expressing MHC-I were capable of providing the signals necessary to continue the initial activation, expansion and functional differentiation of CD8$^+$ T cells to cytotoxic effector cells (FIG. 3B). While priming alone resulted on day 10 in 1%-5% of antigen-specific CD8$^+$ T cells within the splenic CD8 T cell population, application ADAS raised this frequency to around 15%-25%.

From the results obtained one can conclude that ADAS will work in vivo with any system capable to provide high enough density of peptide-loaded MHC-I molecules on the surface of lymphocytic cells or even non-lymphocytic cells. Instead of loading MHC-I molecules with peptides externally in vitro, one could envisage systems in which cells would be fed in vitro with whole antigen-comprising protein, allowing the cells to process the antigen and present the antigenic peptides in the context of MHC-I. One could also envisage systems, in which cells would be in vitro exposed to viral systems capable of infecting the cells resulting in the expression of high amounts of a peptide in the context of MHC-I. Further, the MHC-I bearing cells could be transfected with expression vectors coding for a given protein or peptide sequence, again resulting in an efficient presentation of peptides in the context of MHC-I.

Since whole antigen delivered to APC will not only be presented in the context of MHC-I to CD8$^+$ T cells, but also in the context of MHC-II to CD4$^+$ T cells, ADAS can also be used to amplify CD4$^+$ T cell responses. For this particular amplification, the cells used for ADAS have to express MHC-II molecules on the cell surface, which would be loaded with appropriate peptides. This loading could be done by external exposure to suitable peptides, or the MHC-II bearing cells could be transfected by expression vectors coding for a given protein or peptide sequence, again resulting in an efficient presentation of peptides in the context of MHC-II.

Although we applied ADAS through i.v. injection, other routes of application of the peptide-loaded cells are possible. This could be done by subcutaneous, intracutaneous, intramuscular injection, intraperitoneal, intrathecal, or by direct injection into tumor tissue.

Therefore, the administration of a reactivator of step ii) of the present invention may be performed by known methods of administration, in particular selected from subcutaneous (s.c.), intracutaneous, i.v., intramuscular injection, intraperitoneal, intrathecal, or by direct injection into tumor tissue, more preferably by i.v. or s.c. injection.

Also, the administration of a delivery system of step i) of the present invention may be performed by known methods of administration, in particular selected from subcutaneous, intracutaneous, i.v., intramuscular injection, intraperitoneal, intrathecal, or by direct injection into tumor tissue, more preferably by i.v. and s.c. injection.

The molecule binding to a receptor on the surface of a dendritic cell, (b) an antigen-comprising protein bound to molecule of (a) and (c) a first adjuvant are preferably administered as a single pharmaceutical preparation or composition. Such pharmaceutical preparation or composition is preferably a liquid which may further contain pharmaceutical acceptable excipients like buffering compounds. Such pharmaceutical preparation is preferably sterilized.

The volume of the dose of the delivery system of step i) for intramuscular administration is preferably up to about 5 mL, for example, between 0.3 mL and 3 mL, between 1 mL and 3 mL, about 0.5 to 1 mL, or about 2 mL. The amount of active ingredient in each dose should be enough to provide for treatment or prevention. In different embodiments, the unit dose of substance to be delivered should be up to about 5 µg substance/kg body weight, between about 0.2 to 3 µg, between about 0.3 to 1.5 µg, between about 0.4 to 0.8 µg, or about 0.6 µg. In alternative embodiments unit doses could be up to about 6 µg substance/kg body weight, between about 0.05 to 5 µg, or between about 0.1 to 4 µg. Representative amounts of protein per dose are from approximately 1 µg to approximately 1 mg, more preferably from approximately 5 µg to approximately 500 µg, still more preferably from approximately 10 µg to approximately 250 µg and most preferably from approximately 25 µg to approximately 100 µg.

The number of cells of a reactivator comprising a peptide-loaded major histocompatibility complex class I (MHC-I) presenting cell and a second adjuvant to be administered in step ii) can vary and is typically in the range of from $1\times10^6$ to $400\times10^6$ cells, preferably is in the range of from $1\times10^6$ to $200\times10^6$ cells.

Complexed IL-2 as reactivator is preferably administered as a solution and/or at a dosage in the range of from 1 µg/kg body weight to 200 µg/kg body weight, more preferably of from 1 µg/kg body weight to 50 µg/kg body weight, even more preferably of from 1 µg/kg body weight to 20 µg/kg body weight wherein the amounts refer to the IL-2 content in the composition.

Although we tested the effect of ADAS after targeting of antigen into XCR1$^+$ DC, one can conclude from our results that any system leading to a significant initial activation ("priming") or re-activation of CD8$^+$ T cells and/or CD4$^+$ T cells by T cell receptor triggering in vivo can be amplified with the ADAS approach.

The lymphokine IL-2 has been used in the past in order to expand T cell and NK cell populations and was shown to be effective, when provided in a "complexed" from, i.e. bound to an antibody blocking its binding to the high affinity IL-2 receptor chain (CD25, Boyman et al., 2006, Science 311, 1924-1927).

We tested complexed IL-2 (IL-2cx) in our system of T cell activation through targeting of antigen into XCR1+DC. Contrary to expectations, priming of the T cell response followed by application of IL-2cx alone did not significantly increase the number of antigen-specific CD8$^+$ T cells (FIG. 4). Application of ADAS alone on day increased the number of antigen-specific CD8$^+$ T cells from around $0.2\times10^6$ after priming alone to around $2\times10^6$ and thus approximately 10-fold, as described above. However, and very surprisingly, when applied in the context of ADAS, IL-2cx very strongly augmented the amplification of antigen-specific CD8$^+$ T cells to approximately $100-200\times10^6$ antigen-specific CD8+, i.e. approximately by a factor of 50-100. This highly synergistic effect indicated that ADAS created favorable conditions for the biological effects of IL-2, when IL-2 was applied in a complexed form. The combination of ADAS and IL-2cx was amplifying the initial priming to such a degree that now the large majority of all splenic immune cells were composed of antigen-specific CD8$^+$ T cells. When further examined, this massively expanded T cell population expressed granzyme B to approximately 60-70% indicating a high cytotoxic potential.

In order to test the cytotoxic capacity of CD8$^+$ T cells amplified under various conditions we chose a tumor model, in which a highly aggressive OVA-transfected tumor line is injected s.c. into syngeneic C57BL/6 mice and allowed to grow for 6 days to a substantial size (around 20 mm$^2$). From day 6, groups of mice were either left untreated, or were treated by different regimes. Priming of the tumor-bearing mice on day 6 alone by targeting of OVA into XCR1$^+$ DC barely had any effect on the growth of the tumor (FIG. 5) and the same was true if the mice were not primed, but treated with IL-2cx alone. Surprisingly, priming of the mice on day 6, followed by a treatment with IL-2cx alone for the consecutive days significantly reduced the growth of the tumor until day 22, indicating induction of substantial killing capacity in vivo. However, the tumor resumed its growth around day 22 indicating that not all of the tumor mass could be removed. Also the application of ADAS on day 6 after priming very substantially reduced the growth of the tumor which, however, re-started to grow around day 18 (FIG. 5). Interestingly, the application of ADAS on day 6 after priming combined with consecutive application of IL-2cx was clearly most effective in reducing the size of the tumor until the end of the experiment (FIG. 5). The obtained results indicated that injection of IL-2cx alone within a given timeframe after targeting of antigen into APC was already very effective in controlling the growth of the tumor. Further, the outcome indicated that ADAS, when applied within a given timeframe after initial activation of CD8 T cells by antigen, also induced strong killing activity against a tumor expressing this antigen. Most effective in controlling the growth of an aggressive tumor was a combination of ADAS and IL-2cx (FIG. 5). Although in this experiment ADAS was applied first and followed by IL-2cx, the treatment sequence could also be reversed. In this case IL-2cx would be applied first, followed at an appropriate time by ADAS.

In preferred embodiment of step i) of the medicament for use in a method of the present invention is disclosed in WO 2009/065561 for XCR1 as receptor on the surface of a dendritic cell. As disclosed in WO 2009/065561, an anti-XCR1 antibody or fragment thereof, or XCL1 or a functionally active fragment thereof can preferably be employed as molecule binding to a receptor on the surface of a dendritic cell. The disclosure of WO 2009/065561 relating to the delivery system wherein XCR1 is receptor on the surface of a dendritic cell is hereby incorporated by reference and the embodiments disclosed therein also apply for step i) of the medicaments for use of the present invention.

Suitable antigen-comprising proteins are known to the skilled person.

For example, numerous suitable antigen-comprising proteins in the context of tumor diseases are known. Moreover, suitable peptides as vaccines are described, as e.g. summarized in Aranda et al., OncoImmunology 2:12, e26621; December 2013 for solid neoplasms, including glioma, lung carcinoma, sarcoma, melanoma, esophageal squamous cell carcinoma, gastric cancer, hepatocellular carcinoma, pancreatic cancer, colorectal carcinoma, renal cell carcinoma, prostate cancer, ovarian carcinoma, gynecologic malignancies, and various other tumors.

The antigen-comprising proteins specifically targeted in these clinical trials encompass cancer-testis antigens such as NY-ESO-1, TTK protein kinase (also known as MOS), lymphocyte antigen 6 complex, locus K (LY6K, best known as URLC10), insulin-like growth factor 2 mRNA binding protein 3 (IGF2BP3, best known as IMP3), ring finger protein (RNF43), and translocase of outer mitochondrial membrane 34 (TOMM34); carcinoembryonic antigens like glypican-3; differentiation antigens such as melan-A (MLANA) and premelanosome protein (PMEL, best known as gp100); tumor-restricted antigens, such as the SYT-SSX fusion (which is selectively expressed by synovial sarcomas as a result of a t(X;18)(p11;q11) chromosomal translocation); as well as so-called "shared tumor-associated antigens" (antigens that are overexpressed by malignant cells but also produced in normal amounts by one or several healthy tissues), including vascular endothelial growth factor receptor 1 (VEGFR1) and VEGFR2, survivin, Wilms tumor 1 (WT1), telomerase reverse transcriptase (TERT), and p53. Such proteins are therefore suitable antigen-comprising proteins in the context of tumor. A further summary on peptide vaccines in cancer is Yamada et al., Cancer Sci, 2013, 104(1):15-21.

In case of inducing a cellular cytotoxic immune response in a tumor patient or a patient to be prophylactically treated regarding a tumor, a suitable antigen-comprised protein involved in tumor disease may be used. Such proteins are known in the art. As described e.g. in Tacken and Figdor (Tacken P. J., Figdor C. G.; Targeted antigen delivery and activation of dendritic cells in vivo: Steps towards cost effective vaccines. Semin. Immunol., 2011, 23(1):12-20), ideal tumor antigens are those known as shared tumor-specific antigens because they are selectively expressed in tumor cells, of various histotypes, and not in MHC-expressing normal tissues. Examples of such type of antigens are the MAGE-A or NY-ESO-1 antigens. The various members in this category of antigens are expressed at variable proportions depending on the tumor type and the disease stage. Thus, vaccines based on these antigens require selection of patients bearing tumors that express the target antigen. Another category of tumor antigens that are deemed valuable for vaccine development are those derived from oncogenic proteins which are overexpressed in tumors. Bona fide non-self tumor antigens are derived from two major sources: viral antigens in the case of tumors of oncogenic viral origin such as cervical carcinomas caused by HPV infection, and somatic mutations.

In case of inducing a cellular cytotoxic immune response in patient suffering from an infection or a patient to be prophylactically treated regarding an infectious disease (or infection), suitable antigen-comprised proteins of a pathogen may be used, in particular a pathogen selected from malaria, tuberculosis, *leishmania* or a virus, in particular a virus selected from an orthomyxovirus, influenza virus, hepatitis A virus, hepatitis B virus, chronic hepatitis C virus, a lentivirus, in particular HI-Virus, cytomegalovirus, a herpes virus, a papillomavirus, a bunyavirus, a calicivirus, a filovirus, a flavivirus, or a respiratory virus. In an even more preferred embodiment, antigen-comprised protein is a protein of a virus selected from a hepatitis C virus, a papillomavirus, a paramyxovirus, or a respiratory virus.

Viruses, in particular RNA viruses, typically exhibit a high mutation rate. However, there are typically conserved regions found in particular in genomic segments encoding non-structural and/or internal proteins, such regions encoding a viral polymerase or a nucleoprotein. Such regions are unsuitable for classical vaccination technologies, as such conserved proteins are not exposed on the viral coat surface. In contrast, such antigen-comprised proteins and/or antigen comprised in the protein may be used in the medicament for use according to the invention.

In a preferred embodiment, the antigen-comprised protein and/or antigen comprised in the protein of a virus is conserved.

In a further preferred embodiment, the antigen-comprised protein is a non-structural protein and/or the antigen is comprised in a non-structural and/or internal protein.

In a yet further preferred embodiment, the antigen-comprised protein is a protein of an RNA virus.

A "non-structural" or "internal" protein is a protein which is not part of the coat or envelope of a virus particle.

In a further embodiment, the antigen is comprised in the protein in step i) is immunodominant. Immunodominant means that, although many pMHC complexes are available for a certain pathogen, T-cell responses are reproducibly focused on one or few key antigens, and such the antigen is one of such key antigens.

Suitable antigen-comprising proteins and antigens of influenza A virus are for example described in Wu et al. (PNAS, 2011, 108(22): 9178-9183), and encompass NP (nucleoprotein), basic polymerase 1 and M1.

Step ii) relates to administering to the patient a re-activator selected from the group consisting of (d) complexed interleukin 2 (IL-2cx), (e) a peptide-loaded major histocompatibility complex class I (MHC-I) presenting cell and a second adjuvant, and (f) a combination of (d) and (e), wherein the peptide is derived from the antigen-comprising protein as defined in step i), thereby re-activating the T cell activated in step i).

In an embodiment, in case of (e), the cell and the second adjuvant are administered in a time frame of from 0 h to 14 days after the administration of the delivery system of step i).

In one preferred embodiment, in case of (e), the cell and the second adjuvant are administered only once in a time frame of from 0 h to 14 days after the administration of the delivery system of step i).

In a preferred embodiment, in case of (e), the cell and the second adjuvant are administered in a time frame of from 48 h to 14 days after the administration of the delivery system of step i).

For example, the cell and the second adjuvant are administered 48 h, 72 h, 3 days, 4 days, 5 days, 6 days, 7 days, 8 days, 9 days, 10 days, 11 days, 12 days, 13 days or 14 days after the administration of the delivery system of step i).

In a more preferred embodiment, in case of (e), the cell and the second adjuvant are administered in a time frame of from 3 days to 9 days, even more preferably of from 4 days to 8 days, for example 4 days, 5 days, 6 days, 7 days, 8 days after the administration of the delivery system of step i).

In another preferred embodiment, in case of (e), the cell and the second adjuvant are administered only once in a time frame of from 0 h to 14 days, preferably in a time frame of from 48 h to 14 days after the administration of the delivery system of step i).

For example, the cell and the second adjuvant are administered only once 48 h, 72 h, 3 days, 4 days, 5 days, 6 days, 7 days, 8 days, 9 days, 10 days, 11 days, 12 days, 13 days or 14 days after the administration of the delivery system of step i).

In a further preferred embodiment, in case of (e), the cell and the second adjuvant are administered only once in a time frame of from 3 days to 9 days, even more preferably of from 4 days to 8 days, for example 4 days, 5 days, 6 days, 7 days, 8 days after the administration of the delivery system of step i).

In case of (d), complexed interleukin 2 (IL-2cx) is administered in a time frame of from 0 h to 14 days after the administration of the delivery system of step i).

In case of (d), complexed interleukin 2 (IL-2cx) is preferably administered repeatedly after the administration of the delivery system of step i) in a time frame of from 0 h to 14 days after the administration of the delivery system of step i). It is further possible, that further administration of complexed IL-2 takes place after 14 days after the administration of the delivery system of step i); however, at least one administration is in a time frame of from 0 h to 14 days.

In a further preferred embodiment, in case of (d), complexed interleukin 2 (IL-2cx) is preferably administered in a time frame of from 48 h to 9 days, even more preferably of from 3 days to 8 days, for example 3 days, 4 days, 5 days, 6 days, 7 days, 8 days after the administration of the delivery system of step i).

In a yet further preferred embodiment, in case of (d), complexed interleukin 2 (IL-2cx) is preferably administered repeatedly in a time frame of from 48 h to 9 days, even more preferably of from 3 days to 8 days, for example 3 days, 4 days, 5 days, 6 days, 7 days, 8 days after the administration of the delivery system of step i). Thus, complexed interleukin 2 (IL-2cx) is preferably administered 1, 2, 3, 4, 5, 6, 7, 8, 9 or 10 times in a time frame of from 48 h to 9 days, even more preferably of from 3 days to 8 days, for example 3 days, 4 days, 5 days, 6 days, 7 days, 8 days after the administration of the delivery system of step i). For example, complexed interleukin 2 (IL-2cx) may be administered daily or every two days. For example, complexed interleukin 2 (IL-2cx) may be administered 48 h, 3 days, 4 days, 5 days, 6 days, 7 days and 8 days after the administration of the delivery system of step i). In another example, complexed interleukin 2 (IL-2cx) may be administered 48 h, 4 days, 6 days, and 8 days after the administration of the delivery system of step i).

It is further possible, that further administration of complexed IL-2 takes place after the indicated time of, e.g. 14 days, preferably 9 or 8 days, after the administration of the delivery system of step i); however, at least one administration is in the indicated time frame.

In case of (f), a combination of complexed interleukin 2 (IL-2cx), and a peptide-loaded major histocompatibility complex class I (MHC-I) presenting cell and a second adjuvant is administered. In a preferred embodiment, the complexed interleukin 2 (IL-2cx) may be administered before, concomitantly or after administration of the peptide-loaded major histocompatibility complex class I (MHC-I) presenting cell and a second adjuvant. Preferably, the peptide-loaded major histocompatibility complex class I (MHC-I) presenting cell and a second adjuvant are only administered once, and the complexed interleukin 2 (IL-2cx) is administered repeatedly in a time frame of from 0 h to 14 days after the administration of the delivery system of step i). In such embodiment, complexed IL-2 may be administered both before, concomitantly and/or after administration of the peptide-loaded major histocompatibility complex class I (MHC-I) presenting cell and a second adjuvant.

For the alternative (f), the same preferred embodiments for administration of complexed IL-2 and peptide-loaded major histocompatibility complex class I (MHC-I) presenting cell and a second adjuvant, respectively, apply as for alternatives (e) and (f).

In one embodiment, in case of (f), the cell and the second adjuvant are administered only once in a time frame of from 0 h to 14 days after the administration of the delivery system of step i).

In a preferred embodiment, in case of (f), the cell and the second adjuvant are administered in a time frame of from 48 h to 14 days after the administration of the delivery system of step i).

For example, in case of (f), the cell and the second adjuvant are administered 48 h, 3 days, 4 days, 5 days, 6 days, 7 days, 8 days, 9 days, 10 days, 11 days, 12 days, 13 days or 14 days after the administration of the delivery system of step i).

In a more preferred embodiment, in case of (f), the cell and the second adjuvant are administered in a time frame of from 3 days to 9 days, even more preferably of from 4 days to 8 days, for example 4 days, 5 days, 6 days, 7 days, 8 days after the administration of the delivery system of step i).

In another preferred embodiment, in case of (f), the cell and the second adjuvant are administered only once in a time frame of from 0 h to 14 days after the administration of the delivery system of step i).

For example, the cell and the second adjuvant are administered only once 48 h, 3 days, 4 days, 5 days, 6 days, 7 days, 8 days, 9 days, 10 days, 11 days, 12 days, 13 days or 14 days after the administration of the delivery system of step i).

In a further preferred embodiment, in case of (f), the cell and the second adjuvant are administered only once in a time frame of from 3 days to 9 days, even more preferably of from 4 days to 8 days, for example 4 days, 5 days, 6 days, 7 days, 8 days after the administration of the delivery system of step i).

In case of (f), complexed interleukin 2 (IL-2cx) is preferably administered repeatedly after the administration of the delivery system of step i) in a time frame of from 0 h to 14 days after the administration of the delivery system of step i). It is further possible, that further administration of complexed IL-2 takes place after 14 days after the administration of the delivery system of step i); however, at least one administration is in a time frame of from 0 h to 14 days. In a further preferred embodiment, in case of (f), complexed interleukin 2 (IL-2cx) is preferably administered in a time frame of from 48 h to 9 days, even more preferably of from 3 days to 8 days, for example 3 days, 4 days, 5 days, 6 days, 7 days, 8 days after the administration of the delivery system of step i).

In a yet further preferred embodiment, in case of (f), complexed interleukin 2 (IL-2cx) is preferably administered repeatedly in a time frame of from 48 h to 9 days, even more preferably of from 3 days to 8 days, for example 3 days, 4 days, 5 days, 6 days, 7 days, 8 days after the administration of the delivery system of step i). Thus, complexed interleukin 2 (IL-2cx) is preferably administered 1, 2, 3, 4, 5, 6, 7, 8, 9 or 10 times in a time frame of from 48 h to 9 days, even more preferably of from 3 days to 8 days, for example 3 days, 4 days, 5 days, 6 days, 7 days, 8 days after the administration of the delivery system of step i). For example, complexed interleukin 2 (IL-2cx) may be administered daily or every two days. For example, complexed interleukin 2 (IL-2cx) may be administered 48 h, 3 days, 4 days, 5 days, 6 days, 7 days and 8 days after the administration of the delivery system of step i). In another example, complexed interleukin 2 (IL-2cx) may be administered 48 h, 4 days, 6 days, and 8 days after the administration of the delivery system of step i).

It is further possible, that further administration of complexed IL-2 takes place after the indicated time of, e.g. 14 days, preferably 9 or 8 days, after the administration of the delivery system of step i); however, at least one administration is in the indicated time frame.

Therefore, in a further preferred embodiment, in case of (f),
(A) the cell and the second adjuvant are administered in a time frame of from 0 h to 14 days, preferably 48 h to 14 days, more preferably in a time frame of from 3 days to 9 days, even more preferably of from 4 days to 8 days, for example 4 days, 5 days, 6 days, 7 days, 8 days after the administration of the delivery system of step i), even more preferably only once in a time frame of from 48 h to 14 days, more particularly only once in a time frame of from 3 days to 9 days, even more particularly only once in a time frame of from 4 days to 8 days, for example 4 days, 5 days, 6 days, 7 days, 8 days after the administration of the delivery system of step i), and
(B) complexed interleukin 2 (IL-2cx) is administered in a time frame of from 0 h to 14 days, more preferably 48 h to 9 days, even more preferably of from 3 days to 8 days, for example 3 days, 4 days, 5 days, 6 days, 7 days, 8 days after the administration of the delivery system of step i), most preferably administered repeatedly in a time frame of from 0 h to 14 days, more preferably 48 h to 9 days, even more preferably of from 3 days to 8 days, for example 3 days, 4 days, 5 days, 6 days, 7 days, 8 days after the administration of the delivery system of step i).

It is further possible, that further administration of complexed IL-2 takes place after 14 days after the administration of the delivery system of step i); however, at least one administration is in a time frame of from 0 h to 14 days.

In a yet further preferred embodiment, in case of (f), complexed interleukin 2 (IL-2cx) is preferably administered repeatedly in a time frame of from 48 h to 9 days, even more preferably of from 3 days to 8 days, for example 3 days, 4 days, 5 days, 6 days, 7 days, 8 days after the administration of the delivery system of step i). Thus, complexed interleukin 2 (IL-2cx) is preferably administered 1, 2, 3, 4, 5, 6, 7, 8, 9 or 10 times in a time frame of from 48 h to 9 days, even more preferably of from 3 days to 8 days, for example 3 days, 4 days, 5 days, 6 days, 7 days, 8 days after the administration of the delivery system of step i). For example, complexed interleukin 2 (IL-2cx) may be administered daily or every two days. For example, complexed interleukin 2 (IL-2cx) may be administered 48 h, 3 days, 4 days, 5 days, 6 days, 7 days and 8 days after the administration of the delivery system of step i). In another example, complexed interleukin 2 (IL-2cx) may be administered 48 h, 4 days, 6 days, and 8 days after the administration of the delivery system of step i).

It is further possible, that further administration of complexed IL-2 takes place after the indicated time of, e.g. 14 days, preferably 9 or 8 days, after the administration of the delivery system of step i); however, at least one administration is in the indicated time frame.

In another preferred embodiment, in case of (f), the cell and the second adjuvant are administered only once in a time frame of from 0 h to 14 days after the administration of the delivery system of step i).

The peptide-loaded major histocompatibility complex class I (MHC-I) presenting cell and the second adjuvant are preferably administered as a single pharmaceutical preparation. Such pharmaceutical preparation is preferably a liquid which may further contain pharmaceutical acceptable excipients like buffering compounds. Such pharmaceutical preparation is preferably sterilized.

In a preferred embodiment of the medicament for use,
(x) the complexed interleukin 2 (IL-2cx) is administered repeatedly, in particular 1, 2, 3, 4, 5, 6, 7, 8, 9, 10, 11, 12, 13 or 14 times, even more preferably wherein the complexed interleukin 2 (IL-2cx) is administered every 1 or 2 days, and/or is administered repeatedly during 5 days to 1 month, even more preferably 1 to 2 weeks, and/or
(xx) the peptide derived from the antigen-comprising protein has a length of 8, 9 or 10 amino acids and/or is a peptide presented by a MHC-I, preferably by allele HLA-A2, HLA-A1, HLA-A3, HLA-B7, HLA-B35, HLA-A24, or HLA-A30, more preferably by allele HLA-A2.

In a preferred embodiment, the complexed interleukin 2 (IL-2cx) is administered repeatedly, in particular 1, 2, 3, 4, 5, 6, 7, 8, 9, 10, 11, 12, 13 or 14 times, even more preferably wherein the complexed interleukin 2 (IL-2cx) is administered every 1 or 2 days, and/or is administered repeatedly during 5 days to 1 month. Therefore, it is possible, as described above, that further administration(s) of complexed IL-2 take place after the timeframe of 14 days, or 9 or 8 days.

As described above, a peptide-loaded major histocompatibility complex class I (MHC-I) presenting cell and a second adjuvant are preferably administered as reactivator in step ii) of the medicaments for use of the present invention. Moreover, the peptide is derived from the antigen-comprising protein as defined in step i).

In one embodiment, the loading can be achieved by in vitro loading of MHC-I molecules with peptides externally as described in the examples. Alternatively cells can be fed in vitro with whole antigen-comprising protein, allowing the cells to process the antigen and present the antigenic peptides in the context of MHC-I, or they are exposed in vitro to viral systems capable of infecting the cells resulting in the expression of high amounts of a peptide in the context of MHC-I, or the MHC-I bearing cells could be transfected with expression vectors coding for a given protein or peptide sequence, again resulting in an efficient presentation of peptides in the context of MHC-I.

Methods for determining a peptide for the loading of cells in the context of MHC-I are known in the art. For example, the methods described in Wu et al. (PNAS, 2011, 108(22): 9178-9183) may be used.

In case of applying defined peptides for loading, e.g. by externally loading cells in vitro, the peptide sequence may be chosen by methods known in the art.

Externally loading cells in vitro can be performed by methods known in the art, e.g. by providing an aqueous solution of the peptides, adding the solution to the cells, which are preferably in a buffered solution or medium, incubating the cells with the peptides as to achieve a high saturation of the MHC-I and/or MHC-II with the respective peptide, and optionally washing the cells, e.g. with an aqueous solution.

In one preferred embodiment, cells are loaded in vitro with one peptide which has a sequence which is a subsequence of the antigen-comprising protein. For example, an aqueous solution comprising one such peptide may be added in vitro to a cell population, which is preferably a cell population of the patient.

Alternatively, a mixture of 2, 3, 4, 5, 6, 7, 8, 9, 10 or more different peptide loaded-cell major histocompatibility complex class I (MHC-I) presenting cell populations may be used in step ii), wherein the cells are loaded with different peptides, and wherein the cells are preferably cells of the patient.

Such mixture of cells may be obtained by incubating a cell population, like PBMC cells, with a mixture of 2, 3, 4, 5, 6, 7, 8, 9, 10 or more different peptides, thereby obtaining cells loaded with different peptides in the context of MHC-I. Alternatively, separate cell populations, for example 2, 3, 4, 5, 6, 7, 8, 9, 10 or more cell populations, may be incubated in vitro with different peptides, for example 2, 3, 4, 5, 6, 7, 8, 9, 10 or more different peptides. Thereby, separate major histocompatibility complex class I (MHC-I) presenting cell populations each loaded with a different peptide are thereby obtained. The different peptide loaded-cell major histocompatibility complex class I (MHC-I) presenting cell populations may be administered separately in step ii), or a mixture of the different peptide loaded-cell major histocompatibility complex class I (MHC-I) presenting cell populations may be prepared, which may then be administered in step ii).

In case different peptides are employed, in particular if 2, 3, 4, 5, 6, 7, 8, 9, 10 or more different peptides are employed, such peptides may be derived from the same or a different antigen-comprising protein. In a preferred embodiment, 2, 3, 4, 5, 6, 7, 8, 9, 10 or more different peptides derived from one tumor antigen may be used. This means, that the sequence of each peptide is a subsequence of the tumor antigen. The sequences of such different peptides may be overlapping or non-overlapping. In a further embodiment, 2, 3, 4, 5, 6, 7, 8, 9, 10 or more different peptides derived from 2, 3, 4, 5, 6, 7, 8, 9, 10 or more different tumor antigen may be used. In such embodiment, the different tumor antigens are related to the same or different tumor, preferably to the same tumor.

Preferably, a peptide sequence of a length of 8, 9 or 10 amino acids is chosen, as peptides presented by MHC-I are typically of this length.

As further described in Wu et al., HLA alleles are extremely polymorphic. Therefore, the peptide loaded is preferably a peptide presented by a frequent HLA allele. Therefore, in humans, a peptide presented the most frequent allele HLA-A2 is particularly preferred. Alternatively, peptides presented by HLA-A1, -A3, -B7, -B35, which are the alleles relevant for individuals of Caucasian origin may be used. HLA-A24 may be used for Asian individuals and HLA-A30 for African individuals.

Several suitable tumor-related peptides are described in Speiser and Romero (Seminars in Immunology 22 (2010) 144-154) and references therein. Most of them are HLA-A2 restricted, for example peptides derived from Melan-A/MART-1, one of the gp100 epitopes and tyrosinase for the melanocyte differentiation antigens; prostate surface antigen and PSAP for prostate; carcinoembryonic antigen and MUC-1 for mucosal tumors; HER-2/neu for breast carcinoma; G250 for renal cell carcinoma; the PR1 shared by two myeloid leukemia associated antigens, PR3 and neutrophil elastase which are normally expressed in granulocytes and overexpressed in myeloid leukemia cells; the shared tumor-specific antigens MAGE-A and NY-ESO-1 for various tumor types; and the overexpressed proteins survivin and telomerase. Suitable Influenza A-derived peptides are described in Wu et al (supra).

Therefore, in a further embodiment, the peptide derived from the antigen-comprising protein is a peptide presented by a MHC-I, preferably by allele HLA-A2, HLA-A1, HLA-A3, HLA-B7, HLA-B35, HLA-A24, or HLA-A30, more preferably by allele HLA-A2. Methods for identifying such peptides are described and summarized in Wu et al. (supra). For example, the systematic identification approach of Wu et al. (supra) may be used, or suitable algorithms described therein.

Therefore, in a further embodiment, the peptide derived from the antigen-comprising protein has a length of 8, 9 or 10 amino acids and is a peptide presented by a MHC-I, preferably by allele HLA-A2, HLA-A1, HLA-A3, HLA-B7, HLA-B35, HLA-A24, or HLA-A30, more preferably by allele HLA-A2.

In a further preferred embodiment of the medicament for use, the receptor on the surface of a dendritic cell is a receptor on the surface of cross-presenting dendritic cells.

Cross-presenting dendritic cells are particularly suitable for presenting peptides in the context of MHC-I. A cross-presenting DC is capable to take up soluble or targeted protein, process it, and present it in the context of MHC-I. All conventional DC are capable of antigen cross-presentation. Quantitatively optimal antigen cross-presentation is done by XCR1$^+$ DC in the mouse and by XCR1$^+$ DC within the BDCA3$^+$ DC population in the human. Therefore, by XCR1$^+$ DC are preferred murine cross-presenting DC, and XCR1$^+$ DC within the BDCA3$^+$ DC population are preferred human cross-presenting DC.

In a further preferred embodiment of the medicament for use, the receptor on the surface of a dendritic cell is chemokine (C motif) receptor 1 (XCR1), nectin-like molecule 2, a c-type lectin (CLEC) such as CLEC9A.

C-type lectins are Ca$^{++}$-dependent glycan-binding proteins that share primary and secondary structural homology in their carbohydrate-recognition domains (CRDs).

These proteins have a C-type lectin fold, which is a fold with highly variable protein sequence that is also present in many proteins that do not bind carbohydrates.

The sequence of the human receptor CLEC9A is for example described in Caminschi et al., 2008, Blood 112, 3264-3273. A suitable molecule binding to CLEC9A is e.g. a specific monoclonal anti-CLEC9A antibody. The human receptor nectin-like molecule 2 is described in Takai et al., 2003, Cancer Sci 94, 655-667. A suitable molecule binding to nectin-like molecule 2 is e.g. a specific anti-nectin-like molecule 2 monoclonal antibody.

The delivery system is particularly suitable for influencing the Th1 response, and optionally also the Th2 response, in the immune system.

XCR1 is a chemokine receptor and is so far the only member of the "C" sub-family of chemokine receptors. It is also known as GPR5 or CCXCR1. GPR5, cloned previously as an orphan G-protein coupled receptor, has been recognized first in the human and then in the mouse as a monospecific receptor for XCL1 and was accordingly referred to as XCR1.

The natural ligand of XCR1 is XCL1, which is also known as ATAC, lymphotactin or SCM-1. It is the only member of the C family of chemokines. Activation-induced, T cell-derived, and chemokine-related cytokine (ATAC) was cloned in the human (Müller et al., 1995, Eur. J. Immunol. 25, 1744-48), and independently as lymphotactin (Kelner et al., 1994, Science 266, 1395-99) in the mouse and SCM-1 (Yoshida et al., 1995, FEBS Lett. 360, 155-9) in the human. According to the nomenclature on chemokines ATAC/lymphotactin/SCM-1 is now designated "XCL1". XCL1 is secreted mainly by activated CD8$^+$ T-cells, Th1 CD4$^+$ T cells and by NK cells. In the human, a variant of XCL1 designated XCL2 has been described in which the amino acids aspartate and lysine in position 28 and 29 of the full length protein are exchanged for histidine and arginine, respectively (Yoshida et al., 1996, FEBS Lett. 395, 82-8), which may also be used for the present invention. An exemplary method to produce XCL1 in biologically active form is described in Example 8 of WO 2009/065561. Analogous methods may be used in order to produce other biologically active forms of XCL1, e.g. those of other species.

In an even more preferred embodiment, the receptor on the surface of a dendritic cell is XCR1.

The amino acid sequence of human XCR1 is known (NCBI; accession NP_001019815):

```
                                          (SEQ ID NO: 12)
MESSGNPEST TFFYYDLQSQ PCENQAWVFA TLATTVLYCL

VFLLSLVGNS LVLWVLVKYE SLESLTNIFI LNLCLSDLVF

ACLLPVWISP YHWGWVLGDF LCKLLNMIFS ISLYSSIFFL

TIMTIHRYLS VVSPLSTLRV PTLRCRVLVT MAVWVASILS

SILDTIFHKV LSSGCDYSEL TWYLTSVYQH NLFFLLSLGI

ILFCYVEILR TLFRSRSKRR HRTVKLIFAI VVAYFLSWGP

YNFTLFLQTL FRTQIIRSCE AKQQLEYALL ICRNLAFSHC

CFNPVLYVFV GVKFRTHLKH VLRQFWFCRL QAPSPASIPH

SPGAFAYEGA SFY
```

In a further preferred embodiment of the medicament for use, the molecule of a) is a ligand to the receptor or an antibody or antibody fragment against the receptor. In an even more preferred embodiment, the receptor is chemokine (C motif) receptor 1 (XCR1) and the molecule of a) is anti-XCR1 antibody or fragment thereof or chemokine (C motif) ligand 1 (XCL1) or a functionally active variant thereof, particularly comprising or consisting of the sequence of any of SEQ ID NOs: 7 to 10, preferably, of SEQ ID NOs: 8 to 10, more preferably of SEQ ID NOs: 9 or 10, especially of SEQ ID NO: 10.

The amino acid sequences of XCL1 (ATAC) of several species (including human: SEQ ID NO: 1, GenBank accession P47992; mouse: SEQ ID NO: 2, GenBank accession P47993; and rat SEQ ID NO: 3, GenBank accession P51672) are known and are shown as SEQ ID NO: 1 to 3 (see below). Additionally, a specific XCLR1 agonist referred to as K4.1 HHV8 (SEQ ID NO: 4, GenBank accession AAB62672.1) (see below), which is a viral chemokine-like protein, is also known. Any of these naturally occurring XCR1 ligands or any other natural occurring XCR1 ligand may be used.

Alternatively, a functionally active variant of any naturally occurring XCL1 may be used. The term variant encompasses fragments, variants derived by one or more amino acid additions, deletions and/or substitutions and molecules, particularly proteins, comprising any naturally occurring XCL1 or part thereof, such as fusion proteins. The XCL1 portion of the fusion protein may be flanked by the amino acid residue(s) C-terminally, N-terminally, or C- and N-terminally.

The functionally active fragment is characterized by being derived from any natural occurring XCR1 ligand, particularly XCL1, especially those of SEQ ID NO:1 to 4, by one or more amino acid deletions. The deletion(s) may be C-terminally, N-terminally and/or internally. Preferably, the fragment is obtained by at most 1, 2, 3, 4, 5, 6, 7, 8, 9, 10, 20, 30, 40, 50 or 60, more preferably by at most 1, 2, 3, 4, 5, 6, 7, 8, 9, 10, 15, 20, 25 or 30, even more preferably at most 1, 2, 3, 4, 5, 6, 7, 8, 9, 10, 11, 12, 13, 14 or 15, still more preferably at most 1, 2, 3, 4, 5, 6, 7, 8, 9 or 10, most preferably 1, 2, 3, 4 or 5 amino acid deletion(s). The functionally active fragment of the invention is characterized by having a biological activity similar to that displayed by the ligand from which it is derived, including the ability to binding to XCR1 and mediate internalization of a protein of (b). The fragment of the naturally occurring XCR1 ligand, particularly XCL1, especially those of SEQ ID NO:1 to 4, is functionally active in the context of the present invention, if the activity (binding as well as internalization) of the fragment amounts to at least 10%, preferably at least 25%, more preferably at least 50%, even more preferably at least 70%, still more preferably at least 80%, especially at least 90%, particularly at least 95%, most preferably at least 99% of the activity of the XCL1 without sequence alteration. These fragments may be designed or obtained in any desired length, including as small as about 18 to 50 amino acids in length.

The functionally active fragment of the naturally occurring XCR1 ligand, particularly XCL1, especially those of SEQ ID NO:1 to 4, may be also characterized by other structural features. Accordingly, in one preferred embodiment of the invention the functionally active fragments consists of at least 60%, preferably at least 70%, more preferably at least 80%, still more preferably at least 90%, even more preferably at least 95%, most preferably 99% of the amino acids of the XCR1 ligand of any of the SEQ ID NOS: 1 to 4. The functional active fragment as defined above may be derived from the peptide by one or more amino acid deletions. The deletions may be C-terminally, N-terminally and/or internally. The above sequence alignment of SEQ ID NOs: 1 to 4 shows domains of the naturally occurring ligands which seem to be conserved. In a preferred embodiment of the invention, these domains should be maintained in the fragment.

Conserved domains include those amino acids of the processed N-terminus (the processed N-terminus starting with amino acid 22 of non processed N-terminus) for SEQ ID NOs: 1 to 3 and with amino acid 27 for SEQ ID NO 4) at positions 1-2 (V/S G), 13-27 (S/N L X T/S Q/A R L P V/P X K/R I/L K/I X T/G X Y, X=any or no amino acid; SEQ ID NO: 5), 35 to 51 (R/K A V I F I/V T K/H R/S G L/R K/R I/V C A/G D/S P; SEQ ID NO: 6) and a disulfide bridge between cysteine residues at positions 11 and 48 (see also above alignment). A consensus sequence for the sequences of SEQ ID NO: 1 to 4 is XGXXXXXXXXXXCXXX-LXXXRLPXXXXXXXXYXXXXXXXXXXAVI FXTXXGXX-XCXXP (SEQ ID NO: 7) if only identical amino acids are considered and (V/S)GX(E/A)(V/T) XXXXXXXC(V/E)X(S/N)LX(T/S)(Q/A)RLP(V/P)X(K/R) (I/L)(K/I)-X(T/G)XYX(I/T)X(E/T)(G/V)XXXX(R/K)AVIF (V/I)T(K/H)(R/S)G(L/R)(K/R)XC(A/G)-(D/S)P (SEQ ID NO: 8) if identical amino acids and majority amino acids (i.e. amino acids which are present in 3 of the 4 sequences, the alternative amino acid is listed after the slash) are considered. A consensus sequence for the sequences of SEQ ID NO: 1 to 3 is VGXEVXXXXXCVXLXTQRLPVXXIK-TYXIXEGXXRA-VIFXTKRGLXXCADPXAX-WVXXXXXXXDXXXXXXXXXXXTXPTXXQXSXX-TAXT-LTG (SEQ ID NO: 9) if only identical amino acids are considered and VG(T/S)EV-(L/S)X(E/K)(S/R)XCV-(S/N)LXTQRLPV(Q/S)(K/R)IKTY(T/I)IXEG(A/S)(M/L) RAVIF(V/I)TKRGL(K/R)(I/V)- CADP(Q/E)A(K/T)WV (K/R)X(A/V)(I/V)(K/R)(T/S)(V/M)D(G/R)(R/K)(A/S)(S/N)(T/A)-(R/S)(K/N)(N/S)(M/K)(A/I)(E/Q)TXPT(G/Q)(A/T)Q(R/Q)S(T/A)(S/N)TA(V/I)TLTG (SEQ ID NO: 10) if identical amino acids and majority amino acids (i.e. amino acids which are present in 2 of the 3 sequences, the alternative amino acid is listed after the slash) are considered.

Accordingly, in a preferred delivery system for use in the invention the functionally active variant, preferably the functionally active fragment, of XCL1 comprises or consists of the sequence of any of SEQ ID NOs: 7 to 10, preferably of SEQ ID NOs: 8 to 10, more preferably of SEQ ID NOs: 9 or 10, especially of SEQ ID NO: 10.

In a further preferred embodiment of the invention, a XCL1 variant as defined above, wherein the XCR1 ligand is a functionally active variant of an XCR1 ligand of any of the SEQ ID NOS: 1 to 4 and wherein the variant has at least 50% sequence identity to the XCR1 ligand of any of the SEQ ID NOS: 1 to 4 is used. In a more preferred embodiment the functionally active variant has a sequence identity of at least 60%, preferably at least 70%, more preferably at least 80%, still more preferably at least 90%, even more preferably at least 95%, most preferably 99% to the antigen of any of the SEQ ID NOS: 1 to 4.

The percentage of sequence identity can be determined e.g. by sequence alignment. Methods of alignment of sequences for comparison are well known in the art. Various programs and alignment algorithms have been described e.g. in Smith and Waterman, Adv. Appl. Math. 2: 482, 1981 or Pearson and Lipman, Proc. Natl. Acad. Sci. U.S.A. 85: 2444-2448, 1988.

The NCBI Basic Local Alignment Search Tool (BLAST) (Altschul et al., J. Mol. Biol. 215: 403-410, 1990) is available from several sources, including the National Center for Biotechnology Information (NCBI, Bethesda, Md.) and on the Internet, for use in connection with the sequence analysis programs blastp, blastn, blastx, tblastn and tblastx. Variants of an antigen of any of the sequences of SEQ ID NOS: 1 to 4 are typically characterized using the NCBI Blast 2.0, gapped blastp set to default parameters. For comparisons of amino acid sequences of at least 35 amino acids, the Blast 2 sequences function is employed using the default BLOSUM62 matrix set to default parameters, (gap existence cost of 11, and a per residue gap cost of 1). When aligning short peptides (fewer than around 35 amino acids), the alignment is performed using the Blast 2 sequences function, employing the PAM30 matrix set to default parameters (open gap 9, extension gap 1 penalties). Methods for determining sequence identity over such short windows such as 15 amino acids or less are described at the website that is maintained by the National Center for Biotechnology Information in Bethesda, Md. (http://www.ncbi.nlm.nih.gov/BLAST/).

Alternatively, the alignment of multiple sequences may be performed using the MegAlign Sofware from DNAStar (Madison, Wis., USA) employing the ClustalV alignment algorithm (Higgins et al., 1992, Comput. Appl. Biosci. 8, 189-91). In the above alignment this software was used and set to the following default parameters: gap penalty 10, gap length penalty 10. Because of the very low homology, manual adjustments were necessary for the inclusion of SEQ ID NO 4 into the alignment.

The functional active variant is obtained by sequence alterations in the naturally occurring XCR1 ligand, wherein the XCR1 ligand with the sequence alterations retains a function of the unaltered XCR1 ligand, e.g. having a biological activity similar to that displayed by the naturally occurring XCR1 ligand, including the ability to binding to XCR1 and mediate internalization of a protein of (b) in step i). Such sequence alterations can include, but are not limited to, conservative substitutions, deletions, mutations and insertions. These characteristics of the functional active variant can be assessed e.g. as detailed above.

In a still more preferred embodiment the functionally active variant of XCL1 for use is derived from the naturally occurring XCR1 ligand of any of the sequences of SEQ ID NOS: 1 to 4 by conservative substitutions. Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc. In one embodiment, one conservative substitution is included in the peptide. In another embodiment, two conservative substitutions or less are included in the peptide. In a further embodiment, three conservative substitutions or less are included in the peptide.

Examples of conservative amino acid substitutions include, but are not limited to, those listed below:

| Original Residue | Conservative Substitutions |
| --- | --- |
| Ala | Ser |
| Arg | Lys |
| Asn | Gln; His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Asn |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

A suitable monoclonal anti-XCR1 antibody for use according to the invention is for example mAb 6F8 disclosed in WO 2009/065561 or MARX10 (Bachem et al., 2012, Front Immunol 3, 214).

An anti-XCR1 antibody or functionally active fragment thereof may be used in one preferred embodiment as molecule binding to XCR1 as receptor in step i). An anti-XCR1 antibody or functionally active fragment thereof is capable of binding specifically to the XCR1. The functionally active fragment of the antibody is defined analogously to the functionally active fragment of XCL1 (see above), i.e. the functionally active fragment (a) is characterized by being derived from any anti-XCR1 antibody by one or more amino acid deletions, such as C-terminal, N-terminal and/or internal deletions and (b) is characterized by having a biological activity similar to that displayed by the anti-XCR1 antibody from which it is derived, including the ability to binding to XCL1. Naturally occurring antibodies are proteins used by the immune system to identify and neutralize foreign objects. Each naturally occurring antibody has two large heavy chains and two small light chains and can bind to a different antigen. The present invention includes, for example, monoclonal and polyclonal antibodies, chimeric, single chain, and humanized antibodies, as well as Fab fragments, Fab, Fab', F(ab')2', Fv, or the product of a Fab expression library. The antibody or antibody component can further be modified to prolong its biological half-life or in other ways to make them more suitable for targeting. Antibodies generated against XCR1 can be obtained by direct injection of XCR1 or a fragment thereof into an animal or by administering XCR1 or a fragment thereof to an animal, preferably a non-human. The antibody so obtained will then bind to XCR1. For preparation of monoclonal antibodies, any technique known in the art, which provides antibodies produced by continuous cell line cultures, e.g. a hybridoma cell line, can be used. The production of a suitable monoclonal antibody is also detailed in WO 2009/065561. Techniques described for the production of single chain antibodies (U.S. Pat. No. 4,946,778) can be adapted to produce single chain antibodies to XCR1. Also, transgenic mice or other organisms such as other mammals may be used to express humanized antibodies to XCR1.

In a further preferred embodiment of the medicament for use,
the antigen-comprising protein of (b) is in a fusion protein with the molecule of a); and/or
the antigen of the antigen-comprising protein of (b) is an immunogen, a pathogen-derived antigen, or a tumor antigen.

Thus, in one preferred embodiment, the antigen-comprising protein of (b) is in a fusion protein with the molecule of a). Such fusion proteins can be synthesized e.g. synthetically or recombinantly, preferably recombinantly. Such fusion proteins enable efficient targeting to the dendritic cells. For example, fusion proteins of antibody MARX10 with OVA and XCL1 with OVA were successfully used in the Examples.

An immunogen is an antigen that stimulates an immune response. Antigens are substances recognized by specific receptors on T cells (T-cell receptor) and B cells (B-cell receptor) within the immune system and are usually proteins or polysaccharides. This includes parts (coats, capsules, cell walls, flagella, fimbrae, and toxins) of bacteria, viruses, and other microorganisms. In general, lipids and nucleic acids are antigenic only when combined with proteins and polysaccharides. Non-microbial exogenous (non-self) antigens can include pollen, egg white, and proteins from transplanted tissues and organs or on the surface of transfused blood cells.

Antigens can be categorized as endogenous or exogenous. A preferred antigen of the present invention is an exogenous antigen.

In case a pathogen-derived antigen is used, preferably of a virus, bacterium and/or eukaryotic parasite, the medicament is preferably for use in inducing a cellular cytotoxic immune response to an infection with such pathogen.

In case a tumor antigen is used, the medicament is preferably for use in inducing a cellular cytotoxic immune response to such tumor.

Dendritic cells can present exogenous antigens via MHC class I molecules, a process known as "cross-presentation".

In a further preferred embodiment of the medicament for use, the first adjuvant of c) and second adjuvant are independently an adjuvant which supports a Th-1-mediated response, preferably they are independently selected from the group consisting of synthetic or recombinant TLR ligands, like poly ICLC and resiquimod (R848), Montanides, like ISA51, ISA720, saponins like Quil-A, ISCOM, QS-21, AS02 and AS01, polyinosinic:polycytidylic acid (poly I:C), a lipopolysaccharide (LPS), and a CpG oligodeoxynucleotide.

If both a first adjuvant of c) and a second adjuvant are used, they may be the same or they may be different from each other.

In a further preferred embodiment of the medicament for use, the re-activator is a peptide-loaded major histocompatibility complex class I (MHC-I) presenting cell and a second adjuvant, wherein the cell is a blood cell, especially a peripheral blood mononucleated cell (PBMC), preferably in combination with IL-2cx.

In a further preferred embodiment of the medicament for use, the T cell is a CD8+ T cell or a CD4+ T cell, preferably a CD8+ T cell.

In particular, the re-activation of CD8+ T cells is specifically advantageous for obtaining a strong and enhanced cytotoxic immune response.

In a further preferred embodiment of the medicament for use, the time frame is from 72 h to 9 days, particularly from 5 days to 8 days.

In one preferred embodiment, the method steps i) and ii) are performed only once.

However, it is possible to repeat the method steps with the same delivery system and the same reactivator when the immune system has settled again. This is typically the case after at least one month, preferably after at least two months after inducing a cellular cytotoxic immune response according to the invention as described above.

Therefore, in another preferred embodiment, the method steps with the same delivery system according to step i) and the same reactivator according to step ii) is repeated after at least 1, 2, or 3 months after performing the method steps of the invention.

Alternatively, the method steps may be repeated with a different delivery system according to step i), preferably wherein the different delivery system comprises a different antigen-comprising protein (b) and optionally a different molecule binding to a receptor on the surface of a dendritic cell (a). In such embodiment, it is not necessary to wait until the immune system has settled again. Therefore, the method may therefore be repeated with a different delivery system e.g. 7 or 14 days after performing the method steps of the invention for the first time with a first delivery system. In such embodiment, the same or a different reactivator may be used in step ii).

In another embodiment, the present invention relates to a medicament for use in a method of extending a cellular cytotoxic immune response against an antigen-comprising protein, the method comprising the step of:

i) administering to a patient having T cells activated against an antigen a peptide-loaded major histocompatibility complex class I (MHC-I) presenting cell and a second adjuvant, wherein the peptide is derived from the antigen-comprising protein, thereby re-activating the activated T cell, and optionally further administering complexed interleukin 2 (IL-2cx), wherein the re-activator of step i) is administered in a time frame of from 0 h to 14 days after the T cells were activated against an antigen.

For this embodiment, the same preferred embodiments apply, where applicable, as for above described medicaments for use of the present invention.

In an embodiment, the cell and the second adjuvant are administered in a time frame of from 0 h to 14 days after the T cells were activated against an antigen.

In one preferred embodiment, the cell and the second adjuvant are administered only once in a time frame of from 0 h to 14 days after the T cells were activated against an antigen.

In a further preferred embodiment, the cell and the second adjuvant are administered in a time frame of from 48 h to 14 days after the T cells were activated against an antigen.

For example, the cell and the second adjuvant are administered 48 h, 3 days, 4 days, 5 days, 6 days, 7 days, 8 days, 9 days, 10 days, 11 days, 12 days, 13 days or 14 days after the T cells were activated against an antigen.

In a more preferred embodiment, the cell and the second adjuvant are administered in a time frame of from 3 days to 9 days, even more preferably of from 4 days to 8 days, for example 4 days, 5 days, 6 days, 7 days, 8 days after the T cells were activated against an antigen.

In another preferred embodiment, the cell and the second adjuvant are administered only once in a time frame of from 0 h to 14 days after the T cells were activated against an antigen.

In a further preferred embodiment, the cell and the second adjuvant are administered only once in a time frame of from 48 h to 14 days after the T cells were activated against an antigen.

For example, the cell and the second adjuvant are administered only once 48 h, 3 days, 4 days, 5 days, 6 days, 7 days, 8 days, 9 days, 10 days, 11 days, 12 days, 13 days or 14 days after the T cells were activated against an antigen. In a further preferred embodiment, the cell and the second adjuvant are administered only once in a time frame of from 3 days to 9 days, even more preferably of from 4 days to 8 days, for example 4 days, 5 days, 6 days, 7 days, 8 days after the T cells were activated against an antigen.

In one preferred embodiment, a combination of complexed interleukin 2 (IL-2cx), and a peptide-loaded major histocompatibility complex class I (MHC-I) presenting cell and a second adjuvant is administered. In a more preferred embodiment, the complexed interleukin 2 (IL-2cx) may be administered before, concomitantly or after administration of the peptide-loaded major histocompatibility complex class I (MHC-I) presenting cell and a second adjuvant. Preferably, the peptide-loaded major histocompatibility complex class I (MHC-I) presenting cell and a second adjuvant are only administered once, and the complexed interleukin 2 (IL-2cx) is administered repeatedly in a time frame of from 0 h to 14 days after the T cells were activated against an antigen. In such embodiment, complexed IL-2 may be administered both before, concomitantly and/or after administration of the peptide-loaded major histocompatibility complex class I (MHC-I) presenting cell and a second adjuvant.

For of the combination, the same preferred embodiments for administration of peptide-loaded major histocompatibility complex class I (MHC-I) presenting cell and a second adjuvant, apply as for the administration of the cells only.

In one embodiment, in case of the combination, the cell and the second adjuvant are administered only once in a time frame of from 0 h to 14 days after the T cells were activated against an antigen.

In a preferred embodiment, in case of the combination, the cell and the second adjuvant are administered in a time frame of from 48 h to 14 days after the T cells were activated against an antigen. For example, in case of the combination, the cell and the second adjuvant are administered 48 h, 3 days, 4 days, 5 days, 6 days, 7 days, 8 days, 9 days, 10 days, 11 days, 12 days, 13 days or 14 days after the T cells were activated against an antigen.

In a more preferred embodiment, in case of the combination, the cell and the second adjuvant are administered in a time frame of from 3 days to 9 days, even more preferably of from 4 days to 8 days, for example 4 days, 5 days, 6 days, 7 days, 8 days after the T cells were activated against an antigen.

In another preferred embodiment, in case of the combination, the cell and the second adjuvant are administered only once in a time frame of from 0 h to 14 days after the T cells were activated against an antigen.

For example, the cell and the second adjuvant are administered only once 48 h, 3 days, 4 days, 5 days, 6 days, 7 days, 8 days, 9 days, 10 days, 11 days, 12 days, 13 days or 14 days after the T cells were activated against an antigen.

In a further preferred embodiment, in case of the combination, the cell and the second adjuvant are administered only once in a time frame of from 3 days to 9 days, even more preferably of from 4 days to 8 days, for example 4 days, 5 days, 6 days, 7 days, 8 days after the T cells were activated against an antigen.

In case of the combination, complexed interleukin 2 (IL-2cx) is preferably administered repeatedly after the T cells were activated against an antigen in a time frame of from 0 h to 14 days after the T cells were activated against an antigen. It is further possible, that further administration of complexed IL-2 takes place after 14 days after the T cells were activated against an antigen; however, at least one administration is in a time frame of from 0 h to 14 days.

In a further preferred embodiment, in case of the combination, complexed interleukin 2 (IL-2cx) is preferably administered in a time frame of from 48 h to 9 days, even more preferably of from 3 days to 8 days, for example 3 days, 4 days, 5 days, 6 days, 7 days, 8 days after the T cells were activated against an antigen.

In a yet further preferred embodiment, in case of the combination, complexed interleukin 2 (IL-2cx) is preferably administered repeatedly in a time frame of from 48 h to 9 days, even more preferably of from 3 days to 8 days, for example 3 days, 4 days, 5 days, 6 days, 7 days, 8 days after the T cells were activated against an antigen. Thus, complexed interleukin 2 (IL-2cx) is preferably administered 1, 2, 3, 4, 5, 6, 7, 8, 9 or 10 times in a time frame of from 48 h to 9 days, even more preferably of from 3 days to 8 days, for example 3 days, 4 days, 5 days, 6 days, 7 days, 8 days after the T cells were activated against an antigen. For example, complexed interleukin 2 (IL-2cx) may be administered daily or every two days. For example, complexed interleukin 2 (IL-2cx) may be administered 48 h, 3 days, 4 days, 5 days, 6 days, 7 days and 8 days after the T cells were activated against an antigen. In another example, complexed interleukin 2 (IL-2cx) may be administered 48 h, 4 days, 6 days, and 8 days after the T cells were activated against an antigen.

It is further possible, that further administration of complexed IL-2 takes place after the indicated time of, e.g. 14 days, preferably 9 or 8 days, after the administration of the delivery system of step i); however, at least one administration is in the indicated time frame.

Therefore, in a further preferred embodiment, in case of the combination, (A) the cell and the second adjuvant are administered in a time frame of from 0 h to 14 days, preferably 48 h to 14 days, more preferably in a time frame of from 3 days to 9 days, even more preferably of from 4 days to 8 days, for example 4 days, 5 days, 6 days, 7 days, 8 days after the T cells were activated against an antigen, even more preferably only once in a time frame of from 48 h to 14 days, more particularly only once in a time frame of from 3 days to 9 days, even more particularly only once in a time frame of from 4 days to 8 days, for example 4 days, 5 days, 6 days, 7 days, 8 days after the T cells were activated against an antigen, and (B) complexed interleukin 2 (IL-2cx) is administered in a time frame of from 0 h to 14 days, more preferably 48 h to 9 days, even more preferably of from 3 days to 8 days, for example 3 days, 4 days, 5 days, 6 days, 7 days, 8 days after the T cells were activated against an antigen, most preferably administered repeatedly in a time frame of from 0 h to 14 days, more preferably 48 h to 9 days, even more preferably of from 3 days to 8 days, for example 3 days, 4 days, 5 days, 6 days, 7 days, 8 days after the T cells were activated against an antigen.

It is further possible in case of the combination, that further administration of complexed IL-2 takes place after 14 days after the T cells were activated against an antigen; however, at least one administration is in a time frame of from 0 h to 14 days.

In a yet further preferred embodiment, in case of the combination, complexed interleukin 2 (IL-2cx) is preferably administered repeatedly in a time frame of from 48 h to 9 days, even more preferably of from 3 days to 8 days, for example 3 days, 4 days, 5 days, 6 days, 7 days, 8 days after the T cells were activated against an antigen. Thus, complexed interleukin 2 (IL-2cx) is preferably administered 1, 2, 3, 4, 5, 6, 7, 8, 9 or 10 times in a time frame of from 48 h to 9 days, even more preferably of from 3 days to 8 days, for example 3 days, 4 days, 5 days, 6 days, 7 days, 8 days after the T cells were activated against an antigen. For example, complexed interleukin 2 (IL-2cx) may be administered daily or every two days. For example, complexed interleukin 2 (IL-2cx) may be administered 48 h, 3 days, 4 days, 5 days, 6 days, 7 days and 8 days after the T cells were activated against an antigen. In another example, complexed interleukin 2 (IL-2cx) may be administered 0 h, 48 h, 4 days, 6 days, and 8 days after the T cells were activated against an antigen.

It is further possible, that further administration of complexed IL-2 takes place after the indicated time of, e.g. 14 days, preferably 9 or 8 days, after the T cells were activated against an antigen; however, at least one administration is in the indicated time frame.

In another preferred embodiment, in case of the combination, the cell and the second adjuvant are administered only once in a time frame of from 0 h to 14, preferably 48 h to 14 days after the T cells were activated against an antigen.

Although we tested the effect of ADAS after targeting of antigen into XCR1$^+$ DC, one can conclude from our results that any system leading to a significant initial activation ("priming") or re-activation of CD8$^+$ T cells and/or CD4$^+$ T cells by T cell receptor triggering in vivo can be amplified with the ADAS approach. The T cell population could also be initially activated in vitro and later adoptively transferred in vivo, so that ADAS could then be used to amplify the T cell effector response in vivo.

Therefore, in one embodiment, T cells activated against an antigen can be obtained by performing a method as described above in a medicament for use in step i) using a delivery system.

In another preferred embodiment, T cells activated against an antigen can be obtained in vitro. To this end, T cells, which are preferably obtained from the patient to be treated, are co-cultured with antigen or antigen-comprising protein and APC, and antigen-responsive T cells are selected, e.g. by an IFN-γ secretion assay, and expanded with growth factors. Alternatively, antigen-specific T cells are sorted using appropriate tetramers or analogues thereof, exposed to antigen in the presence of APC and expanded with growth factors.

In a preferred embodiment of the medicament for use, the MHC-I presenting cell is a blood cell, especially a peripheral blood mononucleated cell (PBMC).

The MHC-I presenting cell is preferably a cell obtained from the patient to be treated. Methods for obtaining such cells are known to the skilled person. For example, blood may be retrieved and PBMC cells may then be isolated.

In a further preferred embodiment of the medicament for use, the complexed interleukin 2 (IL-2cx) is administered, preferably administered repeatedly, in particular 1, 2, 3, 4, 5, 6, 7, 8, 9, 10, 11, 12, 13 or 14 times, even more preferably wherein the complexed interleukin 2 (IL-2cx) is administered every 1 or 2 days, and/or is administered repeatedly during 5 days to 1 month, even more preferably 1 to 2 weeks.

In a further preferred embodiment of the medicament for use, the peptide derived from the antigen-comprising protein has a length of 8, 9 or 10 amino acids and/or is a peptide presented by a MHC-I, preferably by allele HLA-A2, HLA-A1, HLA-A3, HLA-B7, HLA-B35, HLA-A24, or HLA-A30, more preferably by allele HLA-A2.

In a further preferred embodiment of the medicament for use, the patient is a mammal, in particular a human.

In a further preferred embodiment of the medicament for use, the method of inducing a cellular cytotoxic immune response is for prophylactically treating or treating a tumor and/or an infection.

The medicament for use can be provided to protect from infection ("prophylactically treating"). Alternatively, such a medicament could be used for therapeutic purposes. The infected individual, which may not be able to mount a sufficient Th1 immune response to the pathogen, could be administered a medicament designed to induce and/or extend a cellular cytotoxic response, and would thus become capable of containing or eradicating the infection ("treating"). Examples would be malaria, tuberculosis, *leishmania*, prion diseases, orthomyxoviruses and in particular influenza, hepatitis A, hepatitis B, chronic hepatitis C, HIV and other lentiviruses, cytomegalovirus, herpes viruses, papillomaviruses, bunyaviruses, caliciviruses, filoviruses, flaviviruses and in particular hepatitis C virus, papillomaviruses, paramyxoviruses, a variety of respiratory viruses and other viruses, or any other infection specified in the description.

The vaccine could also be used to protect healthy individuals from developing tumors with known antigenic components (e.g. melanoma, prostate carcinoma) ("prophylactically treating a tumor"). Alternatively, medicament for use could be used to cure patients who already have developed tumors. Examples of such tumors would be human virus-induced tumors, in particular papillomavirus-induced tumors, HCV-induced tumors, hepatitis B-virus induced tumors and others viruses which induce tumors upon chronic infection. Moreover, suitable tumors to be treated are spontaneously arising solid tumors (e.g. melanoma, prostate cancer, breast cancer, adenocarcinoma of the gut, lung cancer) and leukemias.

A pathogen or infectious agent is a biological agent, especially a living microorganism, which causes disease or illness to its host. Pathogen, according to this invention, means preferably a virus, bacterium and/or eukaryotic parasite. A pathogen-derived antigen is an antigen derived from a pathogen.

Cross-presentation of antigen is also of central importance for the eradication of tumors in the body. Tumor cells and tumor antigens have to be taken up, processed, and presented by DC to elicit an anti-tumor immune response. Since the elimination of most tumors requires an effective cytotoxic Th1 T cell response, cross-presentation of tumor antigens is essential. Thus, for an effective anti-tumor response, cross-presenting DC play a pre-eminent role. As shown in Example 5, the medicaments for use of the present invention exhibit a surprising beneficial effect in a tumor model.

In one embodiment, the medicament for use comprises, preferably consists of, (a) a molecule binding to a receptor on the surface of a dendritic cell, and (b) an antigen-comprising protein bound to molecule of (a).

In another embodiment, the medicament for use comprises, preferably consists of, (a) a molecule binding to a receptor on the surface of a dendritic cell, (b) an antigen-comprising protein bound to molecule of (a) and (c) a first adjuvant.

In yet another embodiment, the medicament for use comprises, preferably consists of (A) (a) a molecule binding to a receptor on the surface of a dendritic cell, (b) an antigen-comprising protein bound to molecule of (a) and (c) a first adjuvant and (B) (d) complexed interleukin 2 (IL-2cx), (e) a peptide-loaded major histocompatibility complex class I (MHC-I) presenting cell and a second adjuvant, or (f) a combination of (d) and (e), wherein the peptide is derived from the antigen-comprising protein as defined in (A).

In another embodiment, the present invention relates to a kit-of-parts comprising, preferably consisting of, a delivery system as defined above and a re-activator as defined above.

In yet another embodiment, the present invention relates to a kit-of-parts comprising, preferably consisting of (A) complexed interleukin 2 (IL-2cx), and (B) a peptide-loaded major histocompatibility complex class I (MHC-I) presenting cell and a second adjuvant.

In a yet further embodiment, the present invention relates to a method of extending a cellular cytotoxic immune response against an antigen-comprising protein, the method comprising the step of:

ii) administering to a patient having T cells activated against an antigen a peptide-loaded major histocompatibility complex class I (MHC-I) presenting cell and a second adjuvant, wherein the peptide is derived from the antigen-comprising protein, thereby re-activating the activated T cell, and optionally further administering complexed interleukin 2 (IL-2cx), wherein the re-activator of step i) is administered in a time frame of from 0 h to 14 days after the T cells were activated against an antigen.

In a yet further embodiment, the present invention relates to method of inducing a cellular cytotoxic immune response, the method comprising the steps of:

i) administering to a patient a delivery system comprising (a) a molecule binding to a receptor on the surface of a dendritic cell, (b) an antigen-comprising protein bound to molecule of (a) and (c) a first adjuvant, wherein upon binding of the molecule of (a) to the receptor, the protein of (b) is internalized and processed in the dendritic cell and the antigen comprised in the protein is presented on the surface of the dendritic cell, thereby activating a T cell in the patient; and ii) administering to the patient a re-activator selected from the group consisting of (d) complexed interleukin 2 (IL-2cx), (e) a peptide-loaded major histocompatibility complex class I (MHC-I) presenting cell and a second adjuvant, and (f) a combination of (d) and (e), wherein the peptide is derived from the antigen-comprising protein as defined in step i), thereby re-activating the T cell activated in step i), wherein the re-activator of step ii) is administered in a time frame of from 0 h to 14 days after the administration of the delivery system of step i). For the methods of the present invention and the kits-of-parts of the present invention, the same embodiments apply as for the medicaments for use of the present invention.

FIGURES

Figure 5:
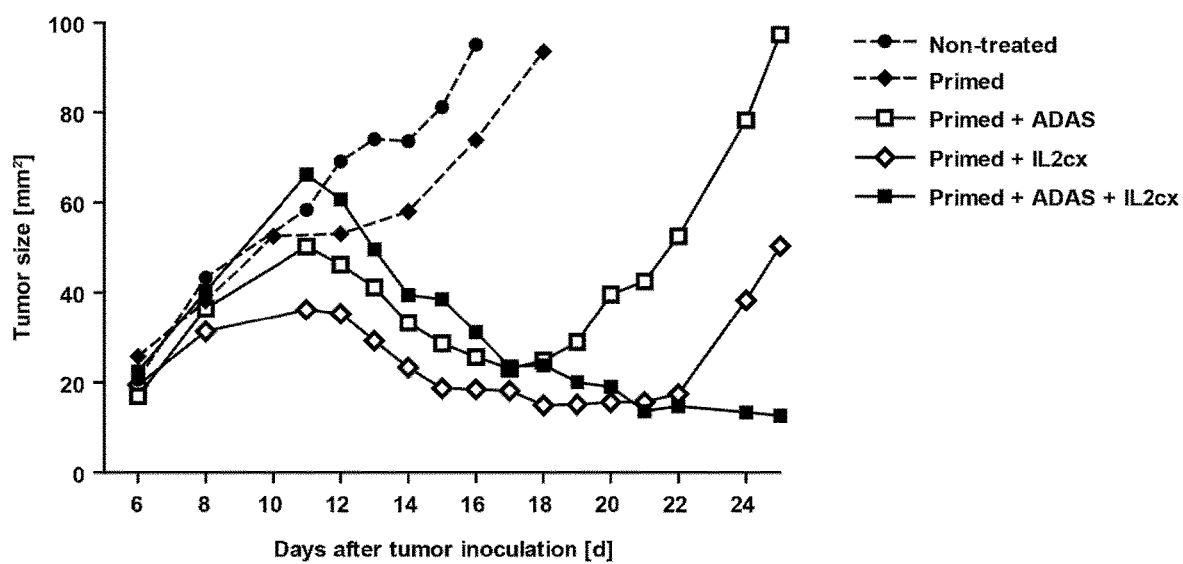
Figure 6:
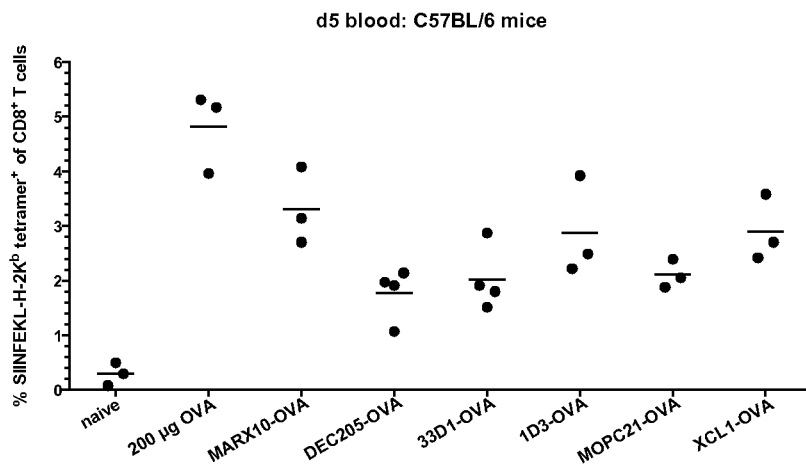
Figure 6:
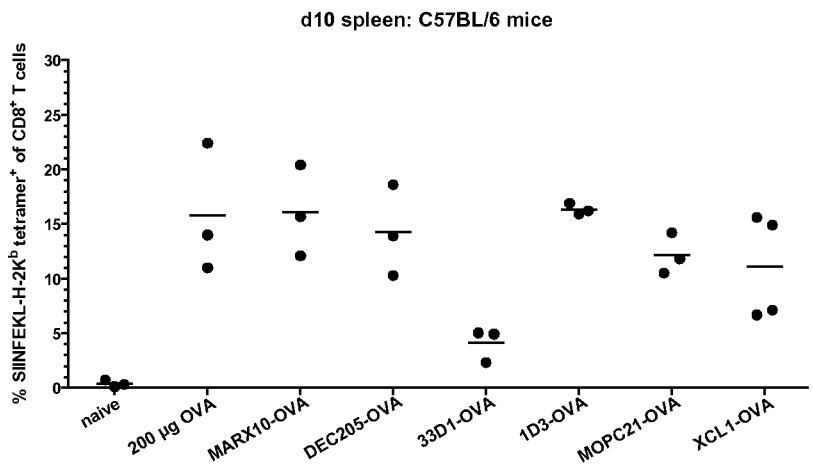
Figure 6:
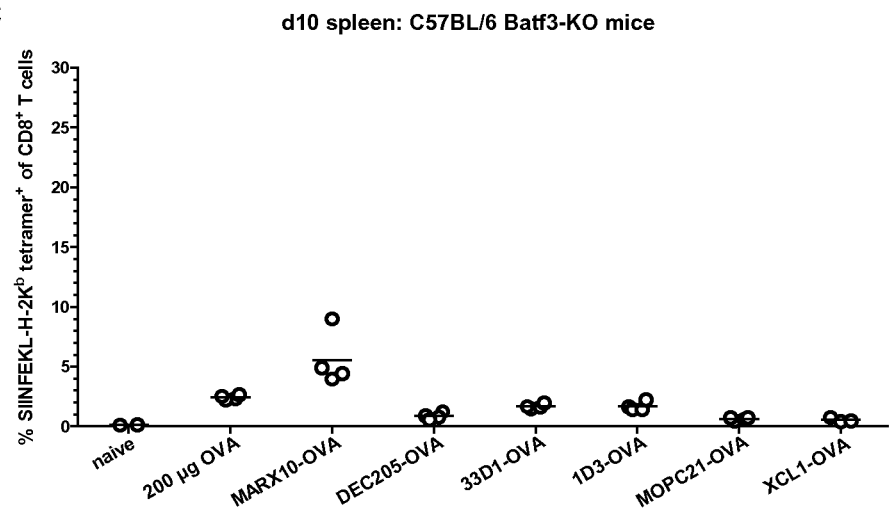

FIG. 5 shows synergistic effects of antigen targeting and co-application of peptide-loaded cells and complexed IL-2 in the treatment of established tumors FIG. 6 shows that the low frequency of cytotoxic CD8+ T cells after priming using various modes of vaccination can be strongly amplified with ADAS. (A) C57BL/6 animals were injected on day 0 with 200 µg of soluble, non-targeted ovalbumin (OVA), or with 5 µg of mAb MARX10-OVA, DEC-205-OVA, 33D1-OVA, MOPC21-OVA; in all cases, 10 µg poly I:C were co-injected as adjuvant. On day 5, blood samples were taken and the frequencies of SIINFEKL-specific CD8+ T cells determined by flow cytometry using a specific tetramer. (B) On day 5, the immune response to the OVA-derived peptide SIINFEKL was amplified with the ADAS procedure (injection of 10×10⁶ syngeneic splenocytes loaded with SIINFEKL together with 50 µg poly I:C as adjuvant). On day 10, the animals were sacrificed and the frequencies of SIINFEKL-specific CD8+ T cells were determined in the spleen using the tetramer. (C) C57BL/6 Batf3-KO animals were immunized as described in (A) and ADAS-treated, as described in (B), and the frequencies of SIINFEKL-specific CD8+ T cells determined in the spleen on day 10.

Figure 7:
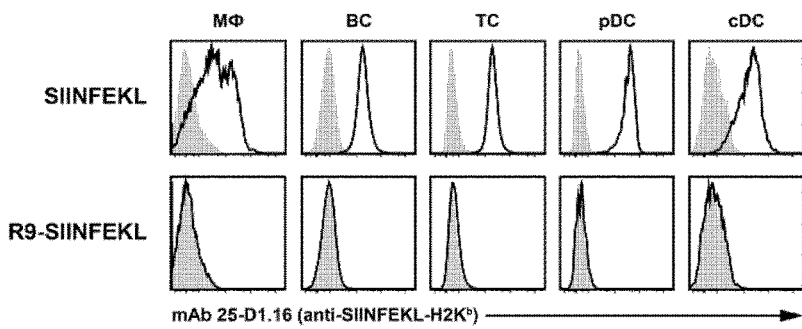
Figure 7:
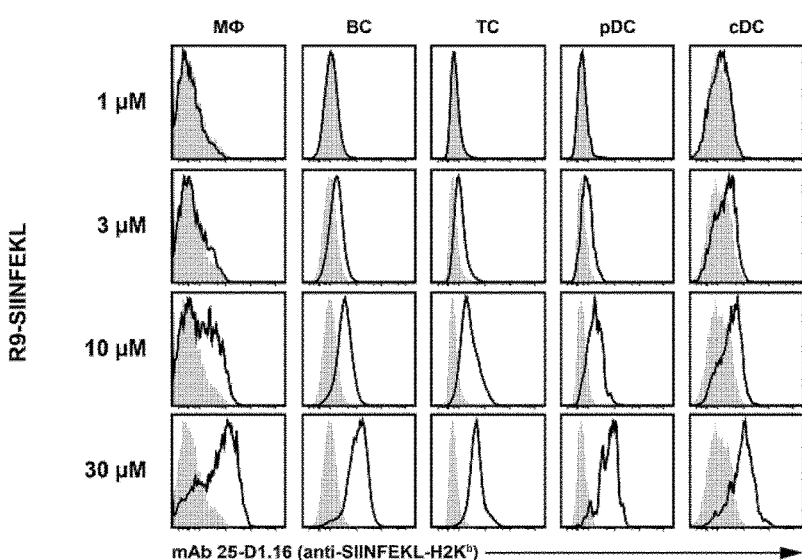
Figure 7:
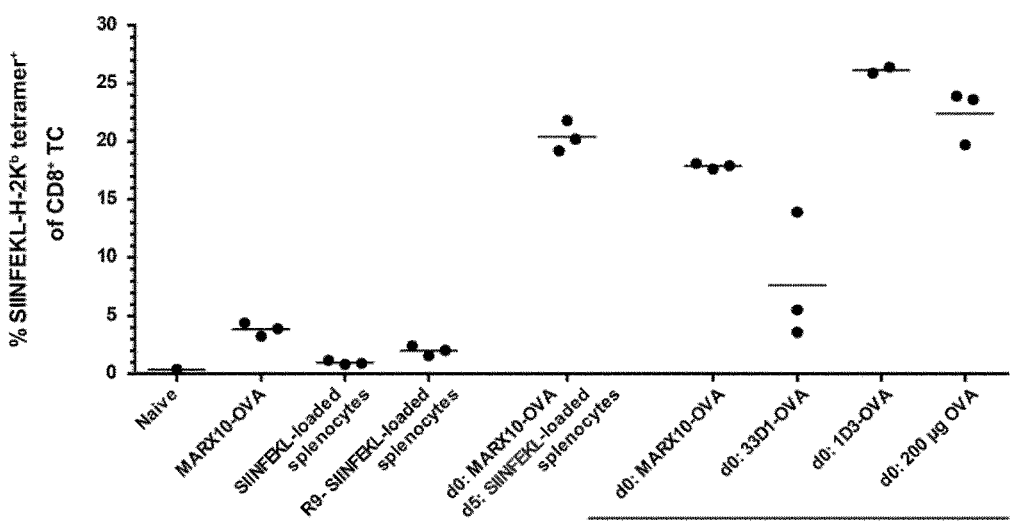

FIG. 7 (A) R9-SIINFEKL polypeptide does not externally bind to the MHC-I groove: C57BL/6 splenocytes were incubated at a density of 5×10⁶ cells/ml with SIINFEKL peptide at 1 µM for 2 h at 37° C., 5% $CO_2$ in complete RPMI1640 culture medium, or at a density of 2×10⁶ cells/ml with R9-SIINFEKL polypeptide at 1 µM for 4 h. Cells were washed twice, and stained with anti-SIINFEKL-H2K$^b$ mAb (clone 25-D1.16) to determine the efficiency of peptide loading to the MHC-I groove. In addition, cells were co-stained with various lineage markers to identify different splenic cell populations and analyzed by flow cytometry. (B) R9-SIINFEKL can be used to transport antigen into the cytoplasmic compartment of primary cells and thus allow loading of MHC-I with derived peptides: C57BL/6 splenocytes were incubated at a density of 2×10⁶ cells with R9-SIINFEKL polypeptide at various concentrations (1-µM) for 7 h as above. Thereafter, the cells were washed twice, stained with mAb 25-D1.16 to determine the efficiency of peptide loading to the MHC-I groove, co-stained with lineage markers, and analyzed by flow cytometry. With 30 µM polypeptide a significant cell death was observed (not shown). (C) R9-SIINFEKL loaded primary cells can be used for ADAS: C57BL/6 mice were injected i.v. on day 0 with 10×10⁶ R9-SIINFEKL loaded (5 µM for 7 h) splenocytes, or for comparison with 10×10⁶ SIINFEKL-loaded (2 µM for 2 h) splenocytes, or with 2 µg MARX10-OVA (all with 10 µg poly I:C) for priming, and the frequency and cytotoxic potential (granzyme B, KLRG1, not shown) of CD8+ T cells were determined on day 5. Alternatively, C57BL/6 mice were primed with 2 µg MARX10-OVA and 10 µg poly I:C, and subjected to ADAS on day 5 by injection i.v. with SIINFEKL-loaded (2 µM for 2 h) splenocytes and 50 µg poly I:C (positive control). In parallel, C57BL/6 mice were primed i.v. with 2 µg MARX10-OVA, or 2 µg 33D1-OVA, or 2 µg 1D3-OVA, or 200 µg untargeted OVA (all together with 10 µg poly I:C) on day 0, and subjected to ADAS by injection i.v. of R9-SIINFEKL-loaded (5 µM for 7 h) syngeneic splenocytes and 50 µg poly I:C. The ADAS-induced expansion of SIINFEKL-specific CD8+ T cells was determined on day 10 by flow cytometry using a specific tetramer. All CD8+ T cells exhibited markers indicative of cytotoxicity (granzyme B, KLRG1, not shown).

Figure 8:
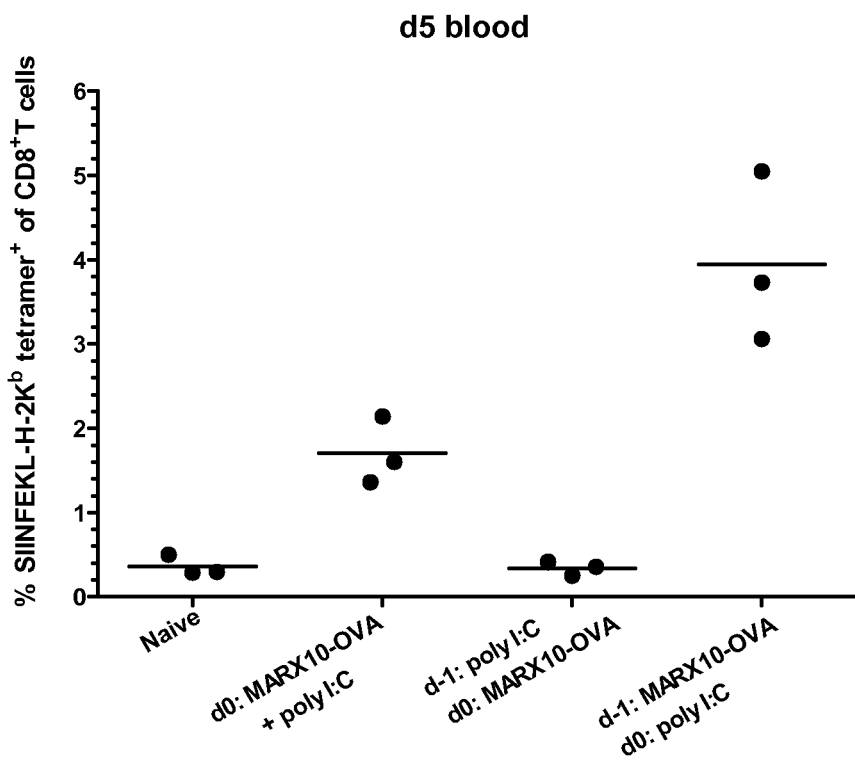
Figure 8:
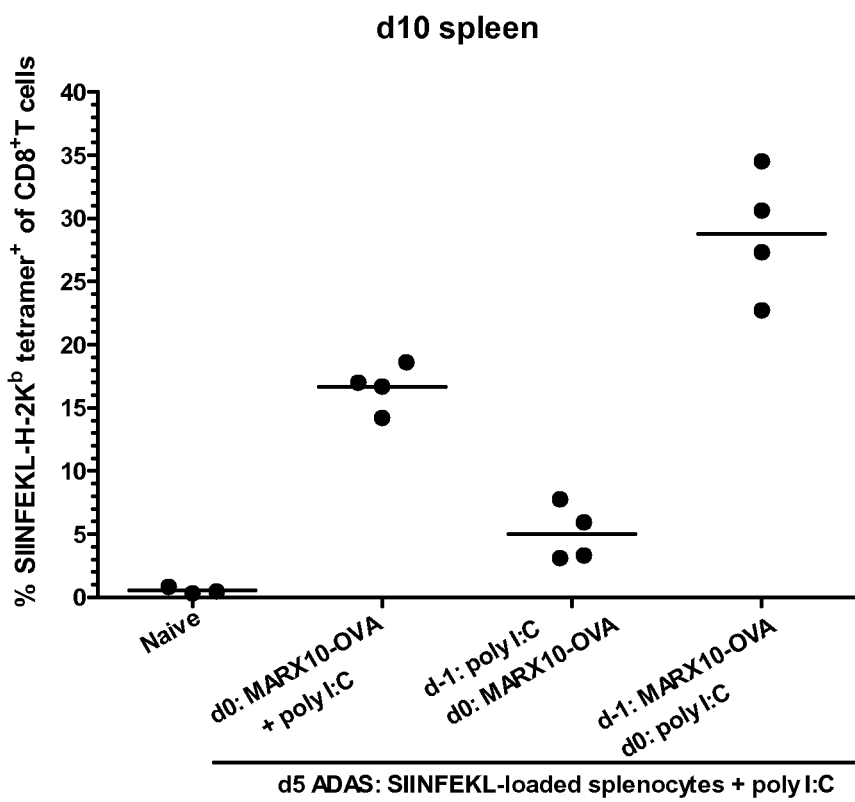

FIG. 8 Administration of antigen can be dissociated from application of adjuvant in the priming step: (A) C57BL/6 mice were injected i.v. on day 0 with 2 µg MARX10-OVA together with 10 µg poly I:C as adjuvant, mixed in one solution. Alternatively, mice were injected on day −1 with 10 µg of poly I:C and on day 0 with 2 µg MARX10-OVA. Alternatively, mice were injected on day 0 with 2 µg MARX10-OVA and on day 1 with 10 µg poly I:C. In each experimental group, blood samples were taken on day 5 and the frequencies of SIINFEKL-specific CD8+ T cells determined by flow cytometry using a specific tetramer. (B) The mice described in (A) were subjected to the ADAS amplification procedure (i.v. injection of splenocytes externally loaded with SIINFEKL together with 50 µg of poly I:C) and the frequencies of SIINFEKL-specific CD8+ T cells in the spleen were determined by flow cytometry. Administration of antigen can be dissociated from application of adjuvant in the ADAS procedure.

Figure 9:
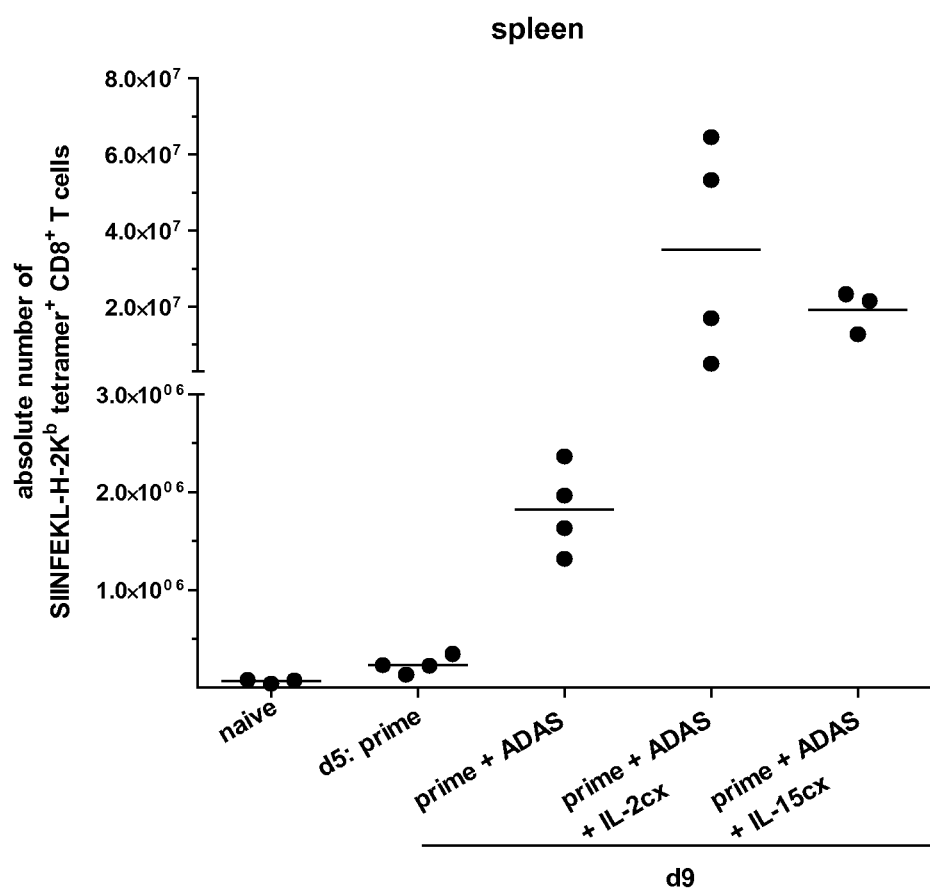

FIG. 9 Highly synergistic amplification of cytotoxic $CD8^+$ T cells by combining ADAS and administration of complexed IL-15: C57BL/6 animals were primed on day 0 with 2 µg MARX10-OVA and 10 µg poly I:C and analyzed for the total number of SIINFEKL-specific $CD8^+$ T cells in the spleen on day 5 (prime) using a specific tetramer and flow cytometry. Some of the primed animals were on day 5 subjected to ADAS only (injection of $10 \times 106$ SIINFEKL-loaded splenocytes together with 50 µg poly I:C), some received ADAS and were injected i.p. with IL-2cx (as described in Examples 4 and 5) on days 6, 7, and 8, other mice received ADAS on day 5 and were injected i.p. with complexed IL-15 (IL-15cx) on day 6, 7, and 8. In all ADAS-treated groups, the total number of SIINFEKL-specific cytotoxic $CD8^+$ T cells was determined on day 9. The dose of IL-15cx for 1 mouse was generated by incubating 2 µg IL-15 (Peprotech #210-15) with 9.3 µg sIL-15R-Fc (R&D, #551-MR-100) at 37° C. for 20 min, PBS was added to 500 µl and the solution injected i.p.

Figure 10:
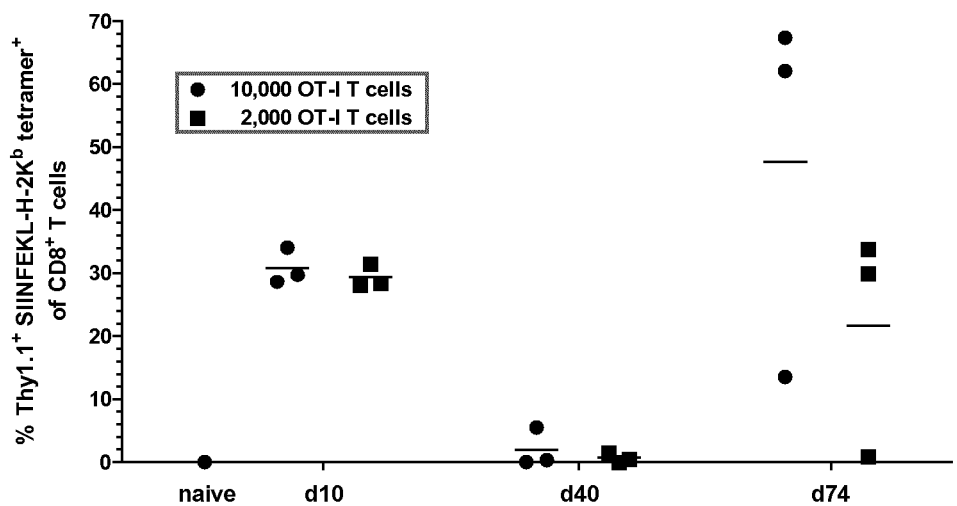
Figure 10:
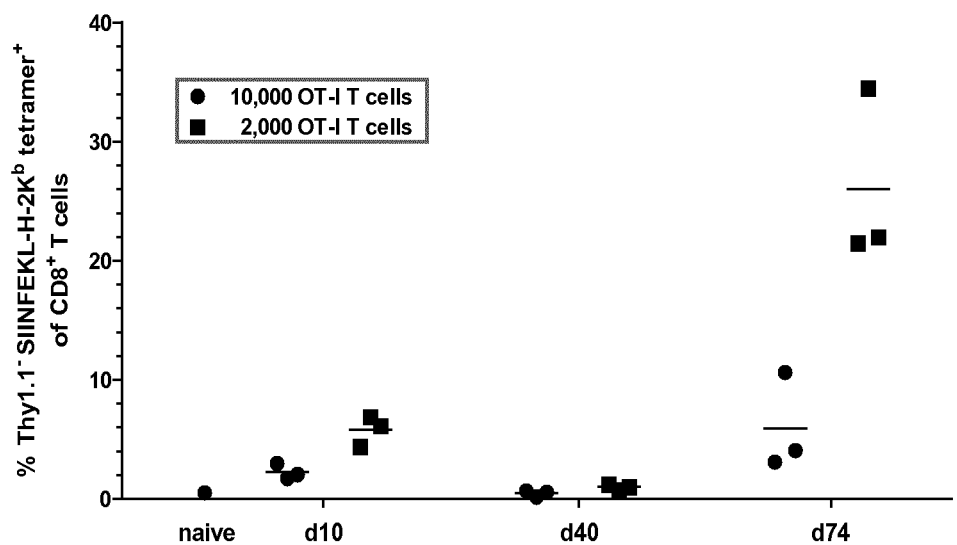

FIG. 10 ADAS can amplify resting memory $CD8^+$ T cells in an antigen-specific manner: C57BL/6 mice were on day −1 adoptively transferred 2,000 or 10,000 of OT-I T cells and primed on day 0 with MARX10-OVA and 10 µg poly I:C. ADAS (injection of $10 \times 10^6$ SIINFEKL-loaded splenocytes together with 50 µg poly I:C) was performed in all animals on day 5, and animals were analyzed for the frequency of (A) OT-I T cells and (B) endogenous, Thy 1.1-negative SIIFEKL-specific $CD8^+$ T cells on days and 40. Another group of mice was subjected to ADAS again on day 69, and analyzed for the frequency of (A) OT-I T cells and (B) endogenous SIINFEKL-specific $CD8^+$ T cells on day 74.

Figure 11:
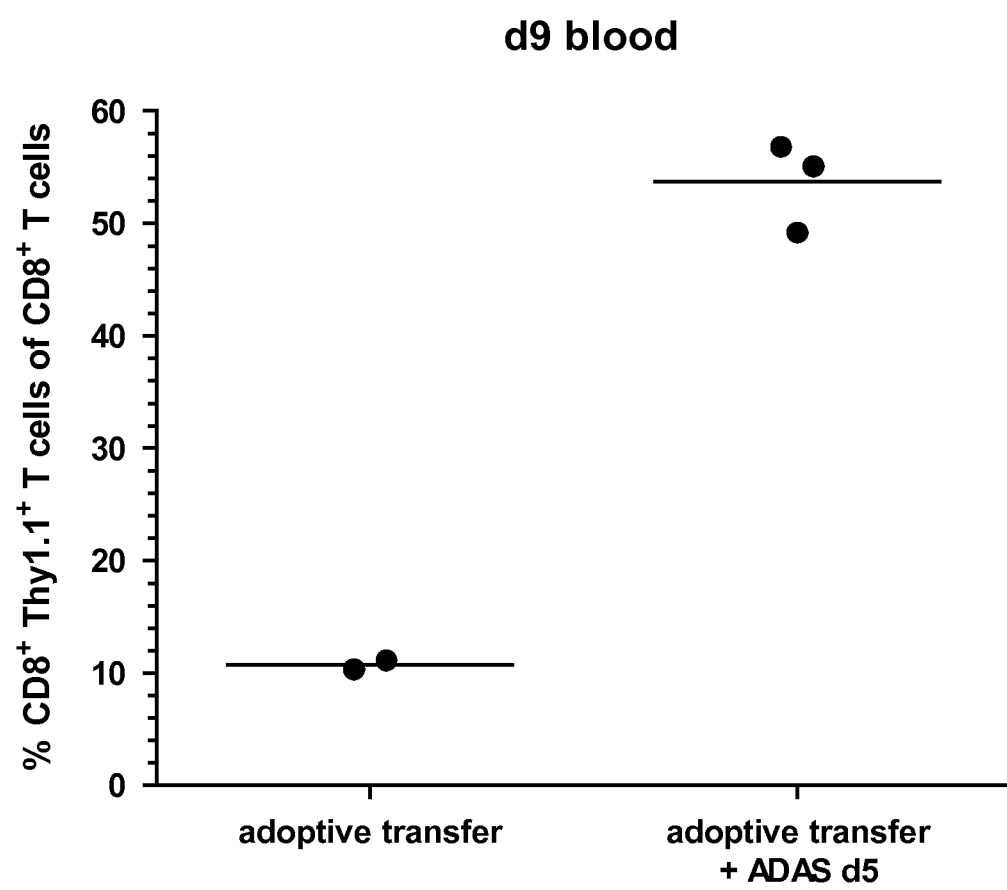

FIG. 11 In vivo amplification of in vitro-activated antigen-specific $CD8^+$ T cells by ADAS: Splenocytes were isolated from OT-I mice and cultured in complete medium with SIINFEKL peptide at 1.4 nM for 3 days. Thereafter, cells were washed with PBS and $5 \times 10^5$ OT-I T cells (as determined by flow cytometry) were adoptively transferred into naïve C57BL/6 mice and the animals were treated by ADAS at various time points after transfer. Shown is the effect on the frequency of transferred $CD8^+$ T cells when ADAS was performed on day 5 after adoptive transfer. The proportion of adoptively transferred $CD8^+$ T cells of all $CD8^+$ T cells was determined in the blood on day 9 using flow cytometry. The frequencies in the blood correspond in these experiments to the frequencies in the spleen of the animals.

EXAMPLES

Example 1

Figure 1:
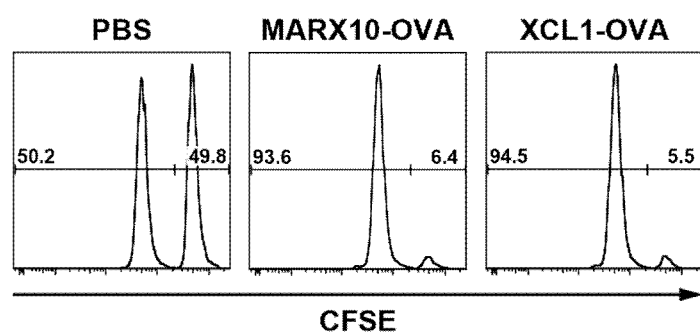
FIG. 1 shows induction of cytotoxic activity after targeting of antigen into XCR1+ DC
Figure 1:
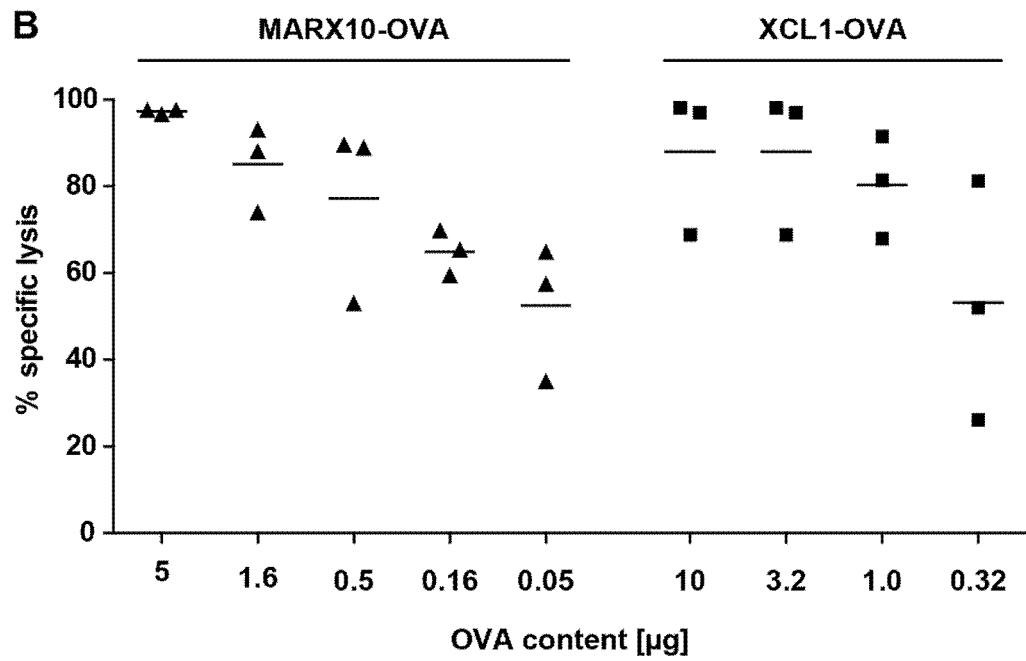

Induction of Cytotoxic Activity after Targeting of Antigen into $XCR1^+$ DC (FIG. 1)

The model antigen OVA was recombinantly fused to the XCR1-specific mAb MARX10 (Bachem et al. 2012) or recombinantly fused to the chemokine ligand XCL1, which specifically binds to the XCR1-receptor (Hartung et al. 2015). When MARX10-OVA or XCL1-OVA were injected i.v. into naïve C57BL/6 mice at low levels, the antigen was targeted into XCR1+DC. If this antigen priming occurred in the presence of an adjuvant (3 µg LPS, CpG, or 10 µg poly I:C), substantial cytotoxic activity was induced (shown are data with poly I:C as adjuvant). This cytotoxic activity was tested by injecting the primed animals on day 6 i.v. with target cells (splenic lymphocytes), which were previously loaded with SIINFEKL (SEQ ID NO: 11) in vitro, an OVA-derived peptide. The target cells were labeled after loading with the fluorophore CFSE to a high degree, while non-loaded control splenic lymphocytes were labeled with CFSE to a low degree. As shown in FIG. 1A, priming animals with OVA+adjuvant resulted in cytotoxic activity which eliminated almost all SIINFEKL-loaded target cells. FIG. 1B shows a dose-response curve obtained with various amounts of antigen targeted to $XCR1^+$ DC. Identical results were obtained after using MARX10-SIINFEKL or XCL1-SIINFEKL for targeting of the immunogenic peptide into XCR1+DC.

Example 2

Figure 2:
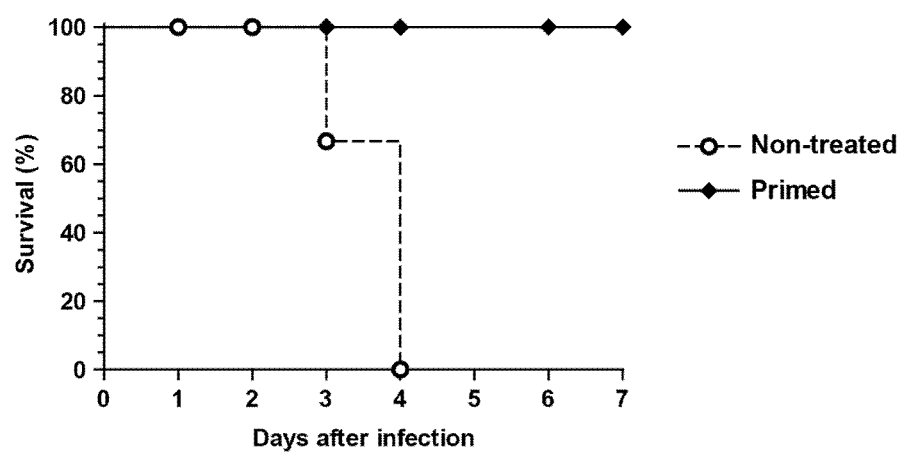
FIG. 2 shows protection from infection or from seeding of cancer cells by the induced cytotoxic activity
Figure 2:
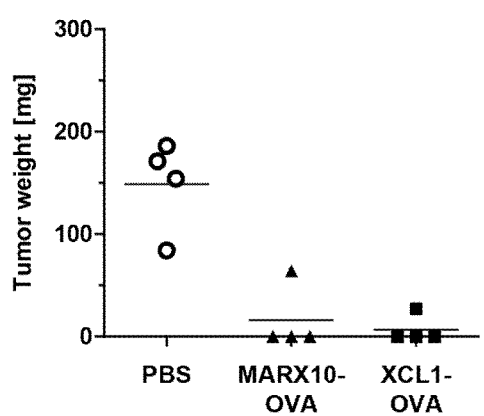

Protection from Infection or from Seeding of Cancer Cells by the Induced Cytotoxic Activity (FIG. 2)

C57BL/6 mice were primed with MARX10-OVA (containing 2 µg of OVA) and adjuvant (10 µg of poly I:C) or were left untreated. Five days later, all mice were infected with $1 \times 10^6$ CFU (=5×LD50) of a *L. monocytogenes* strain, into which the peptide sequence SIINFEKL (SEQ ID NO: 11) has been engineered recombinantly (Foulds et al., 2002, J. Immunol. 168, 1528-1532). While all untreated mice died within 3 to 4 days, the induced level of cytotoxicity by antigenic priming fully protected all animals from disease (FIG. 2A).

C57BL/6 mice were primed with MARX10-OVA or XCL1-OVA (each containing 0.16 µg of OVA) and adjuvant (3 µg LPS) i.v., control animals were injected with PBS. Seven days later, all animals were injected with $5 \times 10^5$ EG.7 cells, an aggressive syngeneic tumor line engineered to express OVA (Moore et al. 1988).

While PBS-treated animals all exhibited strong tumor growth after 14 days, none of the immunized animals had any tumor tissue at the site of injection or elsewhere, indicating that the induced level of cytotoxicity protected the animals from tumor seeding (FIG. 2B).

Example 3

Figure 3:
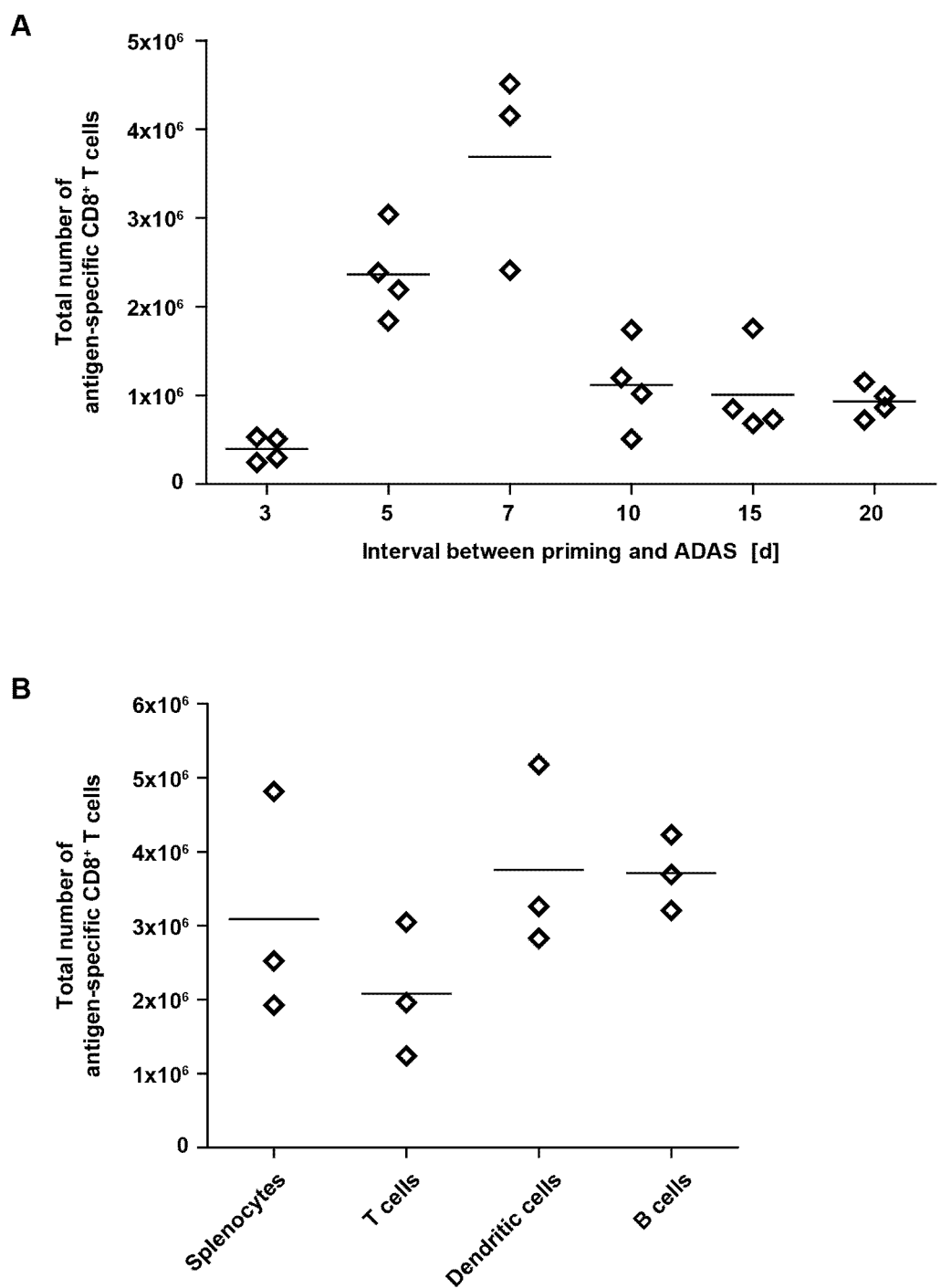
FIG. 3 shows amplification of CD8+ T cell cytotoxicity obtained by injection of syngeneic lymphocytes loaded with antigenic peptide SIINFEKL (SEQ ID NO: 11)

Amplification of $CD8^+$ T Cell Cytotoxicity Obtained by Injection of Syngeneic Lymphocytes Loaded with Antigenic Peptide SIINFEKL (SEQ ID NO: 11) (FIG. 3)

C57BL/6 mice were primed with MARX10-OVA (containing 2 µg OVA) and an adjuvant (poly I, CpG, or LPS, shown are the data with 10 µg poly I:C) on days −20, −15, −10, −7, −5, or −3. On day 0, the primed animals were injected i.v. with $10 \times 10^6$ splenocytes (FIG. 3A) which were loaded before injection with SIINFEKL (SEQ ID NO: 11) in vitro ("Antigen-Dependent Amplification System", ADAS). Together with the peptide-loaded cells an adjuvant was injected (various amounts of LPS or poly I:C), shown are data with 50 µg of poly I:C. On day 10 animals were sacrificed and the total number of SIINFEKL-specific $CD8^+$ T cells was determined in the spleen using SIINFEKL-specific tetramers and flow cytometry (FIG. 3A). The results demonstrated that the system used for amplification of antigen-specific $CD8^+$ T cells was effective in a narrow timeframe between days 5 and 9 after the initial antigenic stimulation (FIG. 3A).

C57BL/6 mice were primed with MARX10-OVA (containing 2 µg OVA) and an adjuvant (10 µg poly I:C). Five days later, 10×10⁶ splenic lymphocytes, or purified T cells, dendritic cells, or B cells which were loaded before injection with SIINFEKL (SEQ ID NO: 11) in vitro were injected i.v. into the primed animals. Together with the peptide-loaded cells an adjuvant was injected (50 µg poly I:C). On day 10 after priming with MARX10-OVA, the animals were sacrificed and the total number of SIINFEKL-specific CD8⁺ T cells was determined in the spleen using SIINFEKL-specific tetramers and flow cytometry. The results showed that the amplification of the cytotoxic CD8⁺ T cell response can be achieved with various cell populations expressing MHC-I on the cell surface. The amplified cells expressed high levels of effector molecules (TNF-α, IFN-γ, granzyme B).

Example 4

Figure 4:
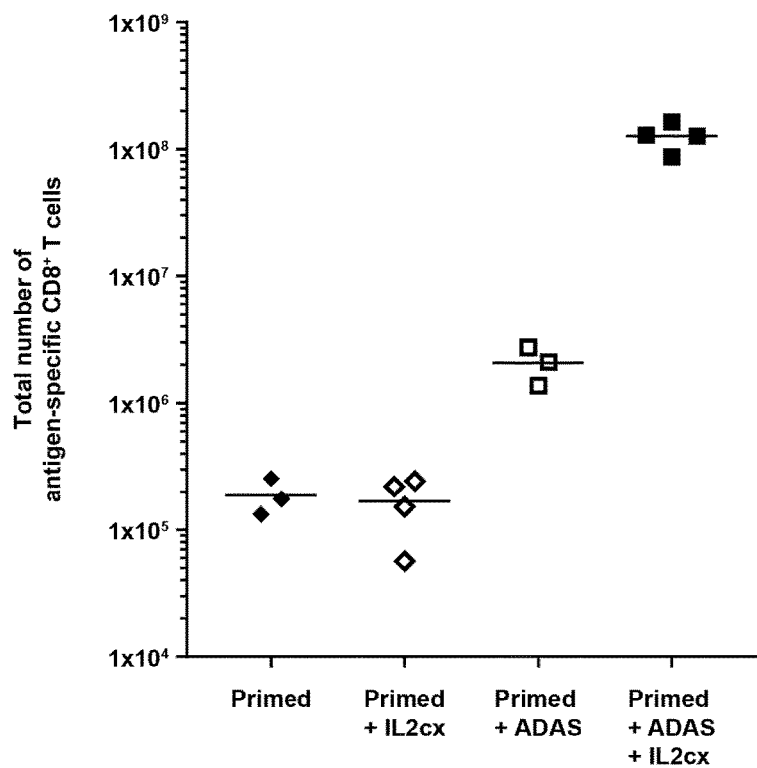
FIG. 4 shows highly synergistic amplification of cytotoxic CD8+ T cells by co-application of peptide-loaded cells and complexed IL-2

Highly Synergistic Amplification of Cytotoxic CD8⁺ T Cells by Co-Application of Peptide-Loaded Cells and Complexed IL-2 (FIG. 4)

C57BL/6 mice were primed with MARX10-OVA (containing 2 µg OVA) and an adjuvant (10 µg poly I:C). One group of primed animals was injected on days 1, 2, and 3 after priming with complexed IL-2 (IL-2cx) obtained by incubating IL-2 (2 µg) and the anti-IL-2 mAb JES6-5H4 (10 µg, Sander et al. 1993) overnight at 4° C., and sacrificed on day 6 ("Primed+IL-2cx"). Another group of mice was injected on day with SIINFEKL-loaded splenocytes (10×10⁶) and adjuvant (50 µg poly I:C) and sacrificed on day 10 ("Primed+ADAS"). Another group of mice was injected on day with SIINFEKL-loaded splenocytes (10×10⁶) and adjuvant (50 µg poly I:C), and with IL-2cx on days 6, 7, 8, and 9, and sacrificed on day 10 ("Primed+ADAS+IL-2cx"). At the end of each experiment, the total number of SIINFEKL-specific CD8⁺ T cells was determined in the spleen using SIINFEKL-specific tetramers and flow cytometry. The experiment determined a highly synergistic effect of ADAS and IL-2cx in the amplification of antigen-specific cytotoxic CD8⁺ T cells.

Example 5

Synergistic Effects of Antigen Targeting and Co-Application of Peptide-Loaded Cells and Complexed IL-2 in the Treatment of Established Tumors (FIG. 5)

C57BL/6 mice were injected s.c. with 5×10⁵ EG.7 cells, an aggressive syngeneic tumor line engineered to express OVA (Moore et al. 1988). On day 6 after tumor injection mice were primed with MARX10-OVA (containing 2 µg OVA) and adjuvant (10 µg poly I:C), one group was left untreated. Six days after priming (day 11), one group of mice was injected with SIINFEKL-loaded splenocytes (10×10⁶) and adjuvant (50 µg poly I:C) ("Primed+ADAS"). Another primed group of mice was injected on days 12, 13, 14, 15, 16, 17, 18, 19, 21, and 23 with IL-2cx only ("Primed+IL-2cx"). Another primed group of mice was injected on day 11 with SIINFEKL-loaded splenocytes (10×10⁶) and adjuvant (50 µg poly I:C), and with IL-2cx on days 12, 13, 14, 15, 16, 17, 18, 19, 21, and 23 ("Primed+ADAS+IL-2cx"). On day 25 all mice were sacrificed (some control animals had to be sacrificed earlier, because the tumor became >1 cm in diameter). All data represent the mean average size of tumors (in mm²) in each treatment group (n=6). The results demonstrate that priming of the tumor-injected mice alone with targeted OVA was not effective. In contrast, either IL-2cx or ADAS alone were effective by strongly reducing the tumor mass for approximately 7-10 days in primed mice, but could not prevent the outgrowth of the tumor thereafter. When a combination of ADAS and IL-2cx was applied to primed animals, the tumor mass was strongly reduced and the tumor was fully controlled until the end of the experiment (some mice had fully rejected the tumor tissue).

Example 6

Various Modes of Immunization, Result in a Low-Frequency of Primed Antigen-Specific CD8+ T Cells. These can be Generally Strongly Expanded and Differentiated to Killer CD8+ T Cells with the ADAS Procedure MAb MARX10 (Bachem et al., Front Immunol 2012, EP2641915A1) recognizes XCR1, the lineage marker for XCR1⁺ DC, Mab DEC-205 (NLDC-145, Kraal et al., 1986, obtained from Biolegend) recognizes the CD205 molecule expressed on murine XCR1⁺ DC, mAb 33D1 (Nussenzweig et al., 1982, obtained from ATCC) recognizes the DCIR2 molecule on SIRP$^a$ DC, mAb 1D3 recognizes CD19 on B cells (Krop et al., 1996, obtained from ATCC), mAb MOPC-21 (Potter et al., J Natl Cancer Inst 1961, obtained from Biolegend) does not recognize any molecule in the mouse and is therefore used as an IgG1 isotype control. XCL1 is the chemokine ligand for XCR1 and can be used for targeting of antigen to XCR1+DC in the mouse and in the human (Hartung et al., 2015).

The antigen-binding regions of the heavy and light chains of mAb DEC-205, 33D1, 1D3, MOPC-21 were identified by mass spectrometry and grafted onto the backbone of mAb DEC-205 by standard recombinant techniques, as described previously for mAb MARX10 (Hartung et al., 2015). This backbone has been modified previously to minimize binding to Fc-receptors. All constructs were then modified in such a way as to accommodate OVA as a C-terminal fusion protein to each of the antibodies, as described previously for mAb MARX10 (Hartung et al., 2015). XCL1-OVA was generated as described previously (Hartung et al., 2015). C57BL/6 animals were injected on day 0 with a high amount (200 µg) of soluble, non-targeted OVA, or with 5 µg of mAb MARX10-OVA, DEC-205-OVA, 33D1-OVA, MOPC21-OVA; in all cases, 10 µg poly I:C were co-injected as an adjuvant. On day 5, blood samples were taken and the frequencies of OVA-specific CD8 T cells determined by flow cytometry using a H-2K$^b$ tetramer loaded with SIINFEKL and capable to bind to SIINFEKL-specific CD8⁺ T cells. As shown in FIG. 6A, all modes of antigen application, either non-targeted, or targeted to XCR1 DC, to SIRPα⁺ DC, or to B cells induced an initial expansion of SIINFEKL-specific CD8⁺ T cells ("priming"), resulting in a frequency of approximately 2-3% of all CD8⁺ T cells in the blood. On day 5, the immune response to the OVA-derived peptide SIINFEKL was amplified with the ADAS procedure (injection of 10×10⁶ SIINFEKL-loaded syngeneic splenocytes together with 50 µg poly I:C). On day 10, the animals were sacrificed and the frequency of SIINFEKL-specific CD8⁺ T cells determined in the spleen. In addition, several markers indicative of cytotoxicity were determined (KLRG1, perforin, granzyme B, data not shown). In all cases, the ADAS procedure amplified the initial frequency of SIINFEKL-specific CD8+ T cells approximately tenfold (FIG. 6B) and induced a phenotype indicative of cytotoxic T cells (not shown).

In parallel, Batf3-KO animals on the C57BL/6 background (animals which lack XCR1+ DC, Hildner et al., 2008) were primed with the non-targeted or targeted OVA reagents, as above. On day 5 the Batf3-KO animals were also treated by the ADAS procedure, as above. On day 10, all animal were sacrificed and the frequencies of SIINFEKL-specific CD8+ T cells were determined in the spleen. While priming, followed by ADAS gave high frequencies of SIINFEKL-specific CD8+ T cells in all C57BL/6 animals (FIG. 6B), no substantial SIINFEKL-specific response could be observed after ADAS in any of the Batf3-KO animals (FIG. 6C).

Several conclusions can be drawn from these experiments. Immunization using high levels of non-targeted protein, when applied together with a Th1 adjuvant, will result in an initial frequency of antigen-specific cytotoxic CD8+ T cells, as demonstrated by us and others previously (Hartung et al., 2015). Targeting of antigen into DC makes this primary immunization much more effective, since only low amounts of antigen are required to achieve the same effect (Hartung et al, 2015, Caminschi et al., 2012). Surprisingly, even targeting of antigen to B cells (in this case via CD19, a surface molecule specifically expressed on B cells) was similarly effective to targeting of antigen to DC. This effect can either be explained by transfer of antigen from B cells to DC (Allan et al., 2006), or by "unspecific" binding of the targeting anybody to Fc-receptors on DC. The latter effect is most likely responsible for the efficiency of priming when using MOPC-21, an isotype control antibody which does not recognize any antigen in the mouse immune system. These results are fully compatible with earlier results, in which targeting of antigen to marginal metallophilic macrophages via the surface receptor Siglec-1 also led to the generation of low-frequency cytotoxic CD8+ T cells, but not in Batf3-KO animals (Backer et al., 2010). Our experiments with Baf3-KO animals are in line with the general assumption that priming of naïve T cells has to occur by DC. In particular, these experiments indicate that XCR1+ DC are required for this initial CD8+ T cell priming. Thus, targeting of antigen into XCR1+ DC promises to be the most effective way of targeting protein antigens, nucleic acids coding for antigens, or viral systems coding for antigens in order to achieve a good primary CD8+ T cell response ("priming").

Together, these results indicate that targeting of antigen using antibodies or targeting using receptor ligands (e.g. XCL1-OVA) to conventional DC, skin DC or other DC, such as monocyte-derived DC, pDC, to macrophages or other cells is far more efficient for induction of an initial cytotoxic response compared to the application of non-targeted antigen. It can be anticipated that all kinds of priming with protein antigens (for example, but no limited to, by employing liposomes, nanoparticles, and other systems as antigen carriers (Saroja et al., 2011) will give similar results, as long as the protein is applied in the context of a Th1 adjuvant. It is also well documented in the literature that a similarly low initial frequency of cytotoxic CD8+ T cells can be induced by non-protein immunization, such as, but not limited to, application or injection of DNA or DNA-based vaccines, or RNA or RNA-based vaccines, into the body using a variety of systems, either targeted or non-targeted (Saroja et al., 2011, Koup et al., 2011, Ulmer et al., 2012, Kramps et al., 2013) Similar priming of CD8+ T cells can be achieved with viral systems or attenuated viruses (Draper et al., 2010). Injection or application of RNA or DNA-based preparations or non-replicating viral systems or attenuated viruses does not necessarily require an additional Th1 adjuvant, since these agents are in many cases self-adjuvanted; i.e. these agents also represent Th1 adjuvants themselves.

It is clear that in essentially all ways of vaccine delivery into the body, the initial CD8+ cytotoxic response will be relatively weak. Such a weak response will in many cases be insufficient to prevent infection, to treat an infection, or to eradicate cancerous tissue. Therefore, there is a need for a system which can strongly amplify the initial priming.

In our experiments, we demonstrate that in all cases in which the initial CD8 cytotoxic response (priming) is insufficient to clear the infection or the tumor, it can be amplified using the ADAS procedure.

Also immunization of patients with tumor tissue or dead cells will lead to a priming of the CD8+ T cell compartment (de Gruijl et al., 2008) and thus will make these cells susceptible to the ADAS procedure.

Alternatively, primary CD8+ T cell activation can be achieved by isolating pre-existing tumor or pathogen-specific CD8+ T cells from a patient, activating and expanding them in vitro, and injecting them back into the patient. These adoptively transferred (re-injected) CD8+ T cells will be re-activated and further expanded and differentiated to cytotoxic T cells by the ADAS procedure.

The ADAS amplification can be in all cases be further augmented synergistically by subsequent injections of complexed IL-2 (Examples 4, 5) or complexed IL-15 (see Example 9).

In our experiments we used poly I:C as adjuvant. Similar results will be achieved with all type of Th1 adjuvants, such as, but not limited to, poly I:C, RIG-I agonists, and TLR8 agonists.

Example 7

Delivery of Antigen into the Cytoplasmic Compartment of Primary Cells for ADAS Leads to an Effective Loading of MHC-I with Antigen-Derived Peptides We have demonstrated that external loading of the MHC-I of a variety of primary cells (e.g. B cells, T cells, DC, splenocytes) with antigen-derived peptide (e.g. SIINFEKL) can be used for ADAS. We have anticipated that the same procedure will also work with a variety of methods introducing whole protein into primary cells or expressing a protein inside the cell, as described above.

To further illustrate this concept we have used a stretch of 9 arginine residues as a cell-penetrating peptide (CPP, Milletti 2012, Bechara et al., 2013) to transport an antigen-comprising protein (polypeptide) into primary cells. The entire sequence of this 37 aa-polypeptide (termed R9-SIINFEKL) is RRRRRRRRRGYPYDVPDYALEQLESIINFEKLTEWTS (SEQ ID No. 13).

R9-SIINFNEKL needs intracellular processing by the proteasome before a derived antigenic peptide (SIINFEKL) is presented on the cell surface in the context of MHC-I. Thus, the system can serve as a model for introducing a whole protein into a primary cell which is then processed by the proteasome into fragments, some of which are then presented on the cell surface in the context of MHC-I.

This polypeptide cannot bind directly, externally, into the groove of the MHC-I. To prove this point, we incubated splenocytes of C57BL/6 mice with the polypeptide R9-SIINFEKL at 1 µM for 4 h 37° C. in complete medium. In parallel, splenocytes were incubated with the peptide SIIN- FEKL, which can directly bind to MHC-I externally, at 1 µM for only 2 h. After incubation, the cells were washed and analyzed by flow cytometry using mAb 25-D1.16, which recognizes SIINFEKL in the context of MHC-I H2K$^b$ (Porgador et al., 1997). While incubation of splenocytes with SIINFEKL gave a strong signal with macrophages, B cells, T cells, pDC, and DC, as expected (since SIINFEKL externally binds to MHC-I), no signal was obtained with the R9-SIINFEKL polypeptide (FIG. 7A). This experiment directly demonstrated that the R9-polypeptide cannot directly fit into the MHC-I groove and serve as antigen.

In the next step, splenocytes were incubated for 7 h at increasing concentrations (1-30 µM) of the R9-SIINFEKL polypeptide. After incubation and washing, the amount of SIINFEKL-loaded MHC-I was determined by staining with mAb 25-D1.16. As shown in FIG. 7B, all examined primary splenic cells exhibited a dose-dependent signal. Although not directly measured, it can be assumed that also the MHC-II was loaded in a similar manner. This experiment demonstrated that a polypeptide, once transported into a cytoplasmic compartment of a primary cell by a CPP, will be processed and presented in the context of the MHC-I (and MHC-II).

From this experiment, it can be deduced that the same procedure will also work with a whole protein, which has also to be processed before being presented in the context of the MHC-I (and MHC-II). In fact, a similar loading of the MHC-I with SIINFEKL has been demonstrated with whole OVA, to which a stretch of 9 arginine residues has been fused N-terminally fused using standard recombinant techniques. In that experiment, OVA was correctly processed and presented in the context of MHC-I, as determined by staining with mAb 25-D1.16 (Mitsui et al. 2006). Thus, our experiment, which is in line with the literature, demonstrates that the introduction of non-processed polypeptides or proteins into the cell using a CPP will effectively load the MHC-I (and MHC-II) of this cell.

From this experiment, one can deduce that any type of internal loading of primary cells with proteins and unprocessed peptides will lead to it an effective MHC-I presentation of peptides derived from this material.

Such an internal loading of primary cells could similarly be achieved with other methods introducing peptides or proteins into cells, for example by, but not limited to, electroporation, or by introducing nucleic acids coding for a peptides and proteins by a variety of methods such as, but not limited to, transfection, lipofection, transduction, injection, ballistic injection, infection.

We then tested the biological potency of primary cells internally loaded using R9-SIINFEKL. To this end, splenocytes from C57BL/6 mice were incubated with R9-SIINFEKL at 5 µM for 7 hours, and washed. They were then injected on day 0 i.v. into naïve C57BL/6 animals and were compared to i.v. injection of SIINFEKL-loaded splenocytes, or to the i.v. injection of MARX10-OVA. All preparation were applied together with poly I:C as adjuvant. As can be seen in FIG. 7C, all methods of antigenic delivery induced a low frequency of SIINFEKL-specific cytotoxic CD8 T cells, as assessed with a specific tetramer and by phenotypic analysis (expression of granzyme B, KLRG1), MARX10-OVA being the most efficient method of antigen delivery.

In the next step, the R9-SIINFEKL loaded splenocytes were assessed for their capacity in the ADAS procedure. In this experiment, priming by MARX10-OVA and ADAS with SIINFEKL-loaded splenocytes served as the positive control and gave around 20% of SIINFEKL-specific cytotoxic CD8$^+$ T cells (FIG. 7C). R9-SIINFEKL-loaded splenocytes were similarly effective in the ADAS procedure after priming with MARX10-OVA, 33D1-OVA, 1D3-OVA or high amounts of non-targeted OVA as SIIFEKL-loaded splenocytes (compare also FIG. 7A). This experiment demonstrated that any type of effective internal loading of primary cells with antigen will be efficient for ADAS. This loading could be with unprocessed polypeptides, whole proteins, or with nucleic acids coding for peptides or proteins, or using infectious agents, or viral or bacterial vector systems recombinantly modified to encode a desired polypeptide or protein.

Example 8

Application of Th1 Adjuvant can be Dissociated in Time from Application of Antigen Both in the Priming Step and in the ADAS Procedure It is currently generally assumed that antigen has to be applied together with an antigen in order to achieve immunization of the host (Cohn et al. 2014). Therefore, antigen is usually mixed with the adjuvant and applied together. It is currently generally assumed that the adjuvant should ideally be even physically linked to the antigen to achieve optimal results. Therefore, it was very surprising for us to realize that a dissociation of antigen administration from adjuvant delivery in the priming and ADAS procedures leads to good and even better immune responses.

C57BL/6 mice were injected i.v. on day 0 with 2 µg MARX10-OVA together with 10 µg poly I:C as adjuvant, mixed in one solution. Alternatively, mice were injected on day −1 with 10 µg of poly I:C and on day 0 with 2 µg MARX10-OVA. Alternatively, mice were injected on day 0 with 2 µg MARX10-OVA and on day 1 with 10 µg poly I:C. In each experimental group, blood samples were taken on day 5 and the frequency of SIINFEKL-specific CD8$^+$ T cells determined by flow cytometry. As can be seen in FIG. 8A, joint administration of antigen and adjuvant on day 0 gave a priming frequency of around 2% of all CD8$^+$ T cells. In contrast, application of adjuvant one day before antigen appeared ineffective. Very surprisingly, administration of antigen on day 0 and application of adjuvant on day 1 was most effective, giving a frequency of around 4% of all CD8$^+$ T cells on day 5.

When all experimental groups were treated by the ADAS procedure (i.v. injection of splenocytes externally loaded with SIINFEKL and 50 µg of poly I:C), the group with the joint application of antigen and adjuvant had around 15% SIINFEKL-specific cytotoxic CD8$^+$ T cells. Clearly the best result was achieved with the group in which adjuvant was applied 1 day after antigen (around 30% SIINFEKL-specific CD8$^+$ T cells). Interestingly, even in the group in which poly I:C was applied 1 day before antigen, there was a low level of SIINFEKL-specific T cells (around 5%), indicating that a certain priming has been achieved even in this group (which then became measurable through the amplification achieved in the ADAS procedure).

These experiments clearly demonstrate that application of antigen and adjuvant can be dissociated in time in the priming procedure. In fact, the results indicate that application of adjuvant some time after administration of antigen is advantageous over a joint application of the components. Our results indicate that application of adjuvant even several days after application of antigen will be effective. The exact time frame cannot be determined in the human and has to be estimated also as 1-2, possibly up to 3 days.

Example 9

Highly Synergistic Amplification of Cytotoxic CD8+ T Cells by Combining ADAS and Administration of Complexed IL-15

We have demonstrated that injection of complexed IL-2 (IL-2cx=murine IL-2 complexed with an antibody blocking the binding of IL-2 to its high affinity receptor CD25) on days 1, 2, and 3 after priming with MARX10-OVA (2 µg) and poly I:C (10 µg) on day 0, did not substantially raise the number of primed CD8+ T cells on day 6. However, when the animals were primed with MARX10-OVA (2 µg) and poly I:C (10 µg) on day 0 and subjected to ADAS (injection of 10×10$^6$ splenocytes loaded with SIINFEKL together with 50 µg poly I:C) on day 5, injection of IL-2cx on days 6, 7, 8, and 9 dramatically raised the number of SIINFEKL-specific CD8+ T cells in the spleen on day 10 (Example 4 and FIG. 4).

Without ADAS, injection of IL-2cx on days 6, 7, 8, and 9 did not substantially raise the number of SIINFEKL-specific CD8+ T cells in the spleen (not shown), but was effective in reducing a tumor burden. Obviously, the ADAS procedure reactivates the primed CD8+ T cells in such a manner that they become highly sensitive to the action of IL-2cx and this results in a strong expansion of cytotoxic CD8+ T cells. However, the exact molecular mechanism leading to this highly heightened sensitivity to IL-2cx remains undetermined.

C57BL/6 animals were primed on day 0 with 2 µg MARX10-OVA and 10 µg poly I:C and subjected to ADAS (injection of 10×10$^6$ SIINFEKL-loaded splenocytes together with 50 µg poly I:C) on day 5. As described earlier, the ADAS procedure raised the level of SIINFEKL-specific CD8+ T cells from around 200,000 on day 5 to around 2×10$^6$ cells after ADAS on day 10 (FIG. 9). ADAS-treated animals were then injected on days 6, 7, and 8 with complexed IL-15 (IL-15cx), or for comparison with IL-2cx (as described above). On day 9, the total number of SIINFEKL-specific CD8+ T cells was determined in the spleen using flow cytometry. As can be seen in FIG. 9, repeated injection of IL-15cx was similarly effective to the repeated injection of IL-2cx in strongly amplifying the number of SIINFEKL-specific CD8+ T cells after the ADAS procedure. IL-15cx could be injected, like IL-2cx, i.v., s.c., i.p., or into a tumor to achieve this effect. Injection of IL-15cx also increased the cellular levels of granzyme B and expression of KLRG1, indicating augmented cytotoxicity (not shown). The dose of IL-15cx for 1 mouse was generated by incubating 2 µg IL 15 (Peprotech #210-15) with 9.3 µg sIL-15R-Fc (R&D, #551-MR-100) at 37° C. for 20 min, PBS was added to 500 µl and the solution injected i.p.

Surprisingly, this experiment thus revealed that IL-15cx could strongly amplify the levels of ADAS-reactivated antigen-specific CD8+ T cells, similar to the action of IL-2cx. From this experiment it can be deduced that in all cases in which injection of IL-2cx was beneficial for the augmentation of the cytotoxic immune response (as described above) also IL-15cx will be effective.

Example 10

The ADAS Procedure can be Used to Re-Activate and Expand Memory CD8+ T Cells in an Antigen-Specific Manner With naïve animals, which were primed with 2 µg MARX10-OVA and 10 µg poly I:C on day 0, we could demonstrate that ADAS is rather ineffective for an amplification of the response when performed on day 3, but becomes effective thereafter, and continues to be effective to a certain extent at least until day 20 (Example 3 and FIG. 3), and is most effective between days 4 and 9 in mice.

In these experiments, ADAS was used to amplify freshly activated naïve antigen-specific CD8+ T cells. The fact that ADAS only optimally works in a certain time window following primary activation of CD8+ T cells indicated that these T cells must be in a particular activation stage in order to be sensitive for the ADAS amplification.

We therefore wondered whether ADAS could also be performed on resting memory CD8+ T cells, which have a clearly different activation status compared to freshly activated CD8+ T cells. To this end, C57BL/6 mice were on day −1 adoptively transferred with 2,000 or 10,000 of OT-I CD8+ T cells, which bear a T cell receptor specific for SIINFEKL presented in the context of H-2K$^b$. These transferred OT-I T cells bore the genetic marker Thy1.1 (CD90.1), which made it possible to discriminate them from endogenous T cells (compare Dorner et al., 2009). On day 0, the animals were primed with MARX10-OVA together with 10 µg poly I:C. ADAS (injection of 10×10$^6$ SIINFEKL-loaded splenocytes together with 50 µg poly I:C) was performed on day 5, resulting in a frequency of 30% of OT-I T cells of all CD8+ T cells in the spleen on day 10 for both groups of adoptively transferred animals (FIG. 10A). When animals from the same experimental groups were analyzed on day 40, the frequency of their OT-I CD8+ T cells had declined to 1-2%, as expected (FIG. 10A). On day 69, another ADAS amplification was performed (injection of 10×10$^6$ splenocytes loaded with SIINFEKL together with 50 µg poly I:C) and the frequency of OT-I T cells was determined in the spleen 5 days later (day 74). Through the ADAS amplification, the frequency of OT-I T cells again rose to 30-60% of all CD8+ T cells in the spleen.

In all animals adoptively transferred with OT-I T cells, we also analyzed the response of endogenous CD8+ T cells, since these could be identified as CD8 T cells negative for the Thy 1.1 marker, but staining with the SIINFEKL-tetramer. As can be seen in FIG. 10B, the endogenous, SIINFEKL-reactive CD8+ T cells showed a behavior similar to the OT-I T cells. In particular, the ADAS procedure could highly amplify endogenous SIINFEKL-specific memory T cells and these T cells bore all phenotypic markers typical of cytotoxic CD8+ T cells (granzyme B positivity, KLRG1-expression, data not shown).

These experiments determined that the ADAS procedure can reactivate and massively expand resting memory CD8+ T cells in an antigen-specific manner, so that they again become CD8+ cytotoxic effectors. Since the ADAS procedure generates a state of T cells in which they are responsive to IL-2cx and IL-15cx, both cytokine preparations will further strongly augment the response of memory CD8+ T cells to ADAS.

In summary, ADAS can not only can amplify freshly activated naïve CD8+ T cells in an antigen-specific manner in a certain time window after activation, but also resting memory CD8+ T cells, i.e. CD8+ T cells in memory state.

Example 11

ADAS is Also Effective with In Vitro Activated, Adoptively Transferred CD8+ T Cells Splenocytes of OT-I mice were in vitro activated with the peptide SIINFEKL for 3 days, without adjuvant. This activation of CD8+ T cells could, however, also be done in the presence of a Th1 adjuvant. After culture, the cells (at this time composed of 97% OT-I CD8+ T cells) were transferred into syngeneic C57BL/6 mice on day 0. ADAS (injection of $10 \times 10^6$ SIIFEKL-loaded splenocytes and 50 μg poly I:C i.v.) was applied on either day 0, 1, 2, 3, 4, 5, or 6. ADAS on days 1, 2 or 3 did not have any significant effect on the frequency of the adoptively transferred CD8+ T cells in the host animals. Clear amplification of the transferred CD8 T cells could, however, be observed with ADAS applied on day 4, and optimal amplification was seen with ADAS on day 5 (FIG. 11). At the same time, the expression of the surface marker KLRG1, indicative of maturation of the transferred CD8+ T cells to effector cells, rose from 30-40% with ADAS on day 1 to 80-90% on days 5 and 6. These data allow to conclude that the ADAS procedure is capable to strongly amplify a population of in vitro-activated and adoptively transferred antigen-specific CD8+ T cells. At the same time, ADAS induces a further differentiation of these CD8+ T cells to cytotoxic effector cells. The optimal time point for ADAS may differ in the human, since experiments in the mouse do not allow a precise prediction in the human. Thus, the period for optimal ADAS effects on the adoptively transferred CD8+ T cells may be more extended. It can also be anticipated that ADAS is not only effective within the short time frame after adoptive transfer of from 0 h to 14 days, but also when the adoptively transferred CD8+ T cells have returned to the memory state after a prolonged period of time.

REFERENCES

Allan, R. S. et al. *Immunity* 25 (2006) 153-162.
Bachem, A. et al. *Front Immunol* 3 (2012) 214.
Backer, R. et al. *Proc Natl Acad Sci USA* 107 (2010) 216-221.
Barnes, E. et al. *Sci Transl Med* 4 (2012) 115ra111.
Bechara, C. et al. *FEBS Lett* 587 (2013) 1693-1702.
Boyman, O. et al. *Science* 311 (2006) 1924-1927.
Caminschi, I. et al. *Front Immunol* 3 (2012) 13.
Carmenate, T. et al. *J Immunol* 190 (2013) 6230-6238.
Cohn, L. et al. *Front Immunol* 5 (2014) 255.
De Gruijl, T. D. et al. *Cancer Immunol Immunother* 57 (2008) 1569-1577.
Draper, S. J. et al. *Nat Rev Microbiol* 8 (2010) 62-73.
Dubensky, T. W., Jr. et al. *Semin Immunol* 22 (2010) 155-161.
Gurka, S. et al. *Front Immunol* 6 (2015) 35.
Hartung, E. et al. *J Immunol* 194 (2015) 1069-1079.
Hildner, K. et al. *Science* 322 (2008) 1097-1100.
Kastenmuiller, W. et al. *Nat Rev Immunol* 14 (2014) 705-711.
Klein, C. S. J *ImmunoTherapy of Cancer* 2 (2014) 18.
Koup, R. A. et al. *Cold Spring Harb Perspect Med* 1 (2011) a007252.
Kraal, G. et al. *J Exp Med* 163 (1986) 981-997.
Kramps, T. et al. *Wiley Interdiscip Rev RNA* 4 (2013) 737-749.
Krop, I. et al. *Eur J Immunol* 26 (1996) 238-242.
Lischke, T. et al. *J Immunol* 189 (2012) 234-244.
Merad, M. et al. *Annu Rev Immunol* 31 (2013) 563-604.
Mitsui, H. et al. *J Invest Dermatol* 126 (2006) 1804-1812.
Moore, M. W. et al. *Cell* 54 (1988) 777-785.
Nussenzweig, M. C. et al. *Proc Natl Acad Sci USA* 79 (1982) 161-165.
Palucka, K., et al. *Immunity* 39 (2013) 38-48.
Paul, W. E. (ed.) Fundamental Immunology, Lippincott Williams & Wilki, 7th edition, ISBN: 978-1451117837.
Porgador, A. et al. *Immunity* 6 (1997) 715-726.
Potter, M. et al. *J Natl Cancer Inst* 26 (1961) 1109-1137.
Probst, H. C. et al. *Nat Immunol* 6 (2005) 280-286.
Ring, A. M. et al. *Nat Immunol* 13 (2012) 1187-1195.
Robert-Guroff, M. *Curr Opin Biotechnol* 18 (2007) 546-556.
Sander, B. *J Immunol Methods* 166 (1993) 201-214.
Saroja, C. et al. *Int J Pharm Investig* 1 (2011) 64-74.
Tacken, P. J. et al. *Semin Immunol* 23 (2011) 12-20.
Ulmer, J. B. et al. *Vaccine* 30 (2012) 4414-4418.
Van Montfoort, N. et al. *Front Immunol* 5 (2014) 182.

The invention claimed is:

1. A method of inducing and amplifying antigen-specific CD8+ T cells in a patient, the method comprising the steps of (A) and (B), wherein step (A) is selected from (A)(i), (A)(ii), or (A)(iii), and step (A) is followed by step (B):
   (A) (i)
      (1) administering to said patient a delivery system comprising:
         (a) a molecule that binds to a receptor on the surface of an antigen-presenting cell, and
         (b) an antigen-comprising protein bound to the molecule of (a) and wherein upon binding of the molecule of (a) to the receptor, the protein of (b) is internalized and processed in the antigen-presenting cell and the antigen comprised in the protein is presented on the surface of the antigen-presenting cell, thereby activating CD8+ T cells in the patient, and
      (2) administering a further adjuvant which supports a Th-1-mediated response, or
   (ii)
      (1) activating one or more CD8+ T cells obtained from said patient in vitro with an antigen-comprising protein or a fragment thereof comprising the antigen,
      (2) re-transferring one or more CD8+ T cells obtained in step (1) to said patient, and
      (3) optionally administering a further adjuvant which supports a Th-1-mediated response,
   or
   (iii)
      (1) administering to said patient an antigen-comprising protein or a fragment thereof comprising the antigen, or
         a nucleic acid comprising a nucleic acid sequence encoding an antigen-comprising protein or a fragment thereof comprising the antigen, which is capable of expressing the antigen-comprising protein or a fragment thereof comprising the antigen in said patient,
         thereby activating CD8+ T cells,
      and
      (2) administering a further adjuvant which supports a Th-1-mediated response, and
   (B) administering to the patient a reactivator comprising:
      (1) primary peptide-loaded major histocompatibility complex class I (MHC I) presenting cells, wherein the MHC I presenting cells do not comprise monocyte-derived dendritic cells, and wherein the peptide is derived from the antigen-comprising protein of step (A), and
      (2) an adjuvant which supports a Th-1-mediated response,
   thereby re-activating the activated CD8+ T cells of step (A), and wherein the reactivator
      is administered in a time frame of from 5 to 12 days after the CD8+ T cells were activated against the antigen in step (A), and
      is administered only once to said patient during the time frame, and
      is administered intravenously to said patient, and
      wherein the MHC I presenting cells are obtained from said patient and peptide-loaded in vitro between 2 h and 3 days prior to administration to the patient.

2. The method of claim 1, wherein said reactivator is administered in a time frame of from 5 to 9 days after the T cells were activated against the antigen.

3. The method of claim 1, wherein the delivery system (A)(i) is administered.

4. The method of claim 1, wherein said molecule that binds to said receptor on the surface of said antigen-presenting cell of (A)(i) is a ligand to the receptor or an antibody or antibody fragment against the receptor.

5. The method of claim 1, wherein said method further comprises administering complexed interleukin 2 (IL-2cx), complexed interleukin 15 (IL-15cx), complexed interleukin 4 (IL-4cx), complexed interleukin 7 (IL-7cx), or a IL-2 mutein.

6. The method of claim 3, wherein said MHC I presenting cells are lymphocytes.

7. The method of claim 6, wherein said lymphocytes are B cells or T cells.

8. The method of claim 1, wherein the receptor on the surface of said antigen-presenting cell of (A)(i) is a receptor on the surface of cross-presenting dendritic cells.

9. The method of claim 8, wherein said receptor on the surface of said cross-presenting dendritic cells is chemokine (C motif) receptor 1 (XCR1), nectin-like molecule 2, CD205, or a c-type lectin (CLEC).

10. The method of claim 5, wherein administering of said complexed interleukin 2 (IL-2cx), complexed interleukin 15 (IL-15cx), complexed interleukin 4 (IL-4cx), complexed interleukin 7 (IL-7cx), or a IL-2 mutein is performed after administering to said patient said MHC I presenting cells coll.

11. The method of claim 1, wherein the antigen of said antigen-comprising protein is an immunogen, a pathogen-derived antigen, or a tumor antigen.

12. The method of claim 9, wherein said receptor on the surface of a dendritic cell is a c-type lectin (CLEC).

13. The method of claim 12, wherein said c-type lectin (CLEC) is CLEC9A.

14. The method of claim 9, wherein said receptor is XCR1.

15. The method of claim 4, wherein said receptor is XCR1 and wherein said molecule is an anti-XCR1 antibody or antigen-binding fragment thereof or chemokine (C motif) ligand 1 (XCL1) or a functionally active variant thereof.

16. The method of claim 1, wherein the MHC I presenting cells comprise at least $1 \times 10^6$ cells.

17. The method of claim 16, wherein the MHC I presenting cells comprise at least $8 \times 10^7$ cells.

* * * * *

UNITED STATES PATENT AND TRADEMARK OFFICE
CERTIFICATE OF CORRECTION

PATENT NO. : 10,688,165 B2
APPLICATION NO. : 15/126487
DATED : June 23, 2020
INVENTOR(S) : Richard Kroczek Page 1 of 1

It is certified that error appears in the above-identified patent and that said Letters Patent is hereby corrected as shown below:

In the Claims

Column 94, Line 61-62, in Claim 10, replace "presenting cells coll." with --presenting cells.--.

Signed and Sealed this
Third Day of August, 2021

Drew Hirshfeld
*Performing the Functions and Duties of the*
*Under Secretary of Commerce for Intellectual Property and*
*Director of the United States Patent and Trademark Office*